United States Patent [19]

Hayashi et al.

[11] Patent Number: 5,397,539
[45] Date of Patent: Mar. 14, 1995

[54] AUTOMATIC ANALYZING APPARATUS

[75] Inventors: Mutsumi Hayashi; Tatsuo Ogasawara; Yayoi Mizutani, all of Otsu; Nobuyuki Kuriyama, Takehanajizoujiminamimachi, all of Japan

[73] Assignee: Toray Industries, Inc., Tokyo, Japan

[21] Appl. No.: 48,204

[22] Filed: Apr. 20, 1993

[30] Foreign Application Priority Data

Apr. 23, 1992 [JP] Japan .................. 4-131894

[51] Int. Cl.[6] ........................ C12M 1/34; G01N 21/11
[52] U.S. Cl. ........................... 422/65; 422/63; 422/67; 422/82.05; 422/100; 435/291
[58] Field of Search ............. 422/63, 65, 67, 82.05, 422/82.08, 82.09, 100; 436/47, 180, 526, 809; 435/287, 291

[56] References Cited

U.S. PATENT DOCUMENTS

| Re. 31,150 | 2/1983 | Ginsberg et al. | 422/64 |
|---|---|---|---|
| 4,323,537 | 4/1982 | Mody | 422/63 |
| 4,606,631 | 8/1986 | Anno et al. | 422/67 X |
| 4,710,355 | 12/1987 | Ushikubo | 422/63 X |
| 4,753,775 | 6/1988 | Ebersole et al. | 422/81 |
| 4,767,716 | 8/1988 | Sakamaki et al. | 422/65 X |
| 4,772,453 | 10/1988 | Lisenbee | 436/809 X |
| 4,812,392 | 3/1989 | Miyake et al. | 422/65 |
| 4,861,554 | 8/1989 | Sakuma | 422/65 |
| 4,895,650 | 1/1990 | Wang | 436/809 X |
| 4,931,256 | 6/1990 | Mack et al. | 436/809 X |
| 4,988,618 | 1/1991 | Li et al. | 436/809 X |
| 5,055,263 | 10/1991 | Meltzer | 436/809 X |
| 5,100,557 | 3/1992 | Nogami et al. | 210/656 |
| 5,104,621 | 4/1992 | Pfost et al. | 422/65 X |
| 5,158,895 | 10/1992 | Ashihara et al. | 436/526 |

FOREIGN PATENT DOCUMENTS

| 53-6094 | 1/1978 | Japan . |
|---|---|---|
| 53-54088 | 5/1978 | Japan . |
| 55-104760 | 8/1980 | Japan . |
| 57-74662 | 5/1982 | Japan . |
| 62-148858 | 7/1987 | Japan . |

*Primary Examiner*—Robert J. Warden
*Assistant Examiner*—Robert Carpenter
*Attorney, Agent, or Firm*—Nikaido Marmelstein Murray & Oram

[57] ABSTRACT

A plurality of cartridges are set to a cartridge standby section. Each cartridge has a specimen tub, a dilution tub and three reaction tubs, and a specimen is placed in the specimen tub in advance. A specimen dispensing unit first distributes the specimen from the specimen tub to three reaction tubs of the same cartridge. Thereafter the cartridges are successively transported to a first reagent dispensing section, a first reaction path, a second dispensing section, a second reaction path, an unreacted component removing section, a luminescent reagent dispensing section and a hydrogen peroxide dispensing section in the stated order. Examination processes including reagent dispensing and unreacted component removal are carried out simultaneously for the three reaction tubs of each cartridge. Finally, reaction mixtures are subjected to photometry in a photometric section. The cartridges are transported by a plurality of transport mechanisms provided for the respective sections and driven independently of one another. Where analytical curve corrections are effected, a specimen dispensing unit and each of sample cartridges holding sample specimens are moved relative to each other. At this time, different specimens are placed in the reaction tubs of the same cartridge to carry out the above examination processes. A new analytical curve is obtained from the results of examination thereof for use in subsequent examination processes.

6 Claims, 30 Drawing Sheets

FIG.6A
FIG.6B
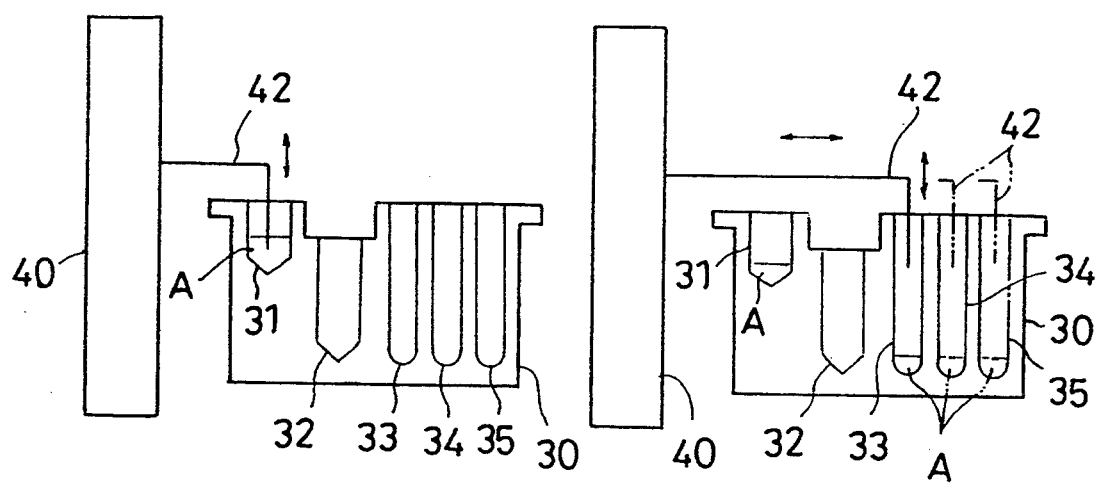
FIG.11
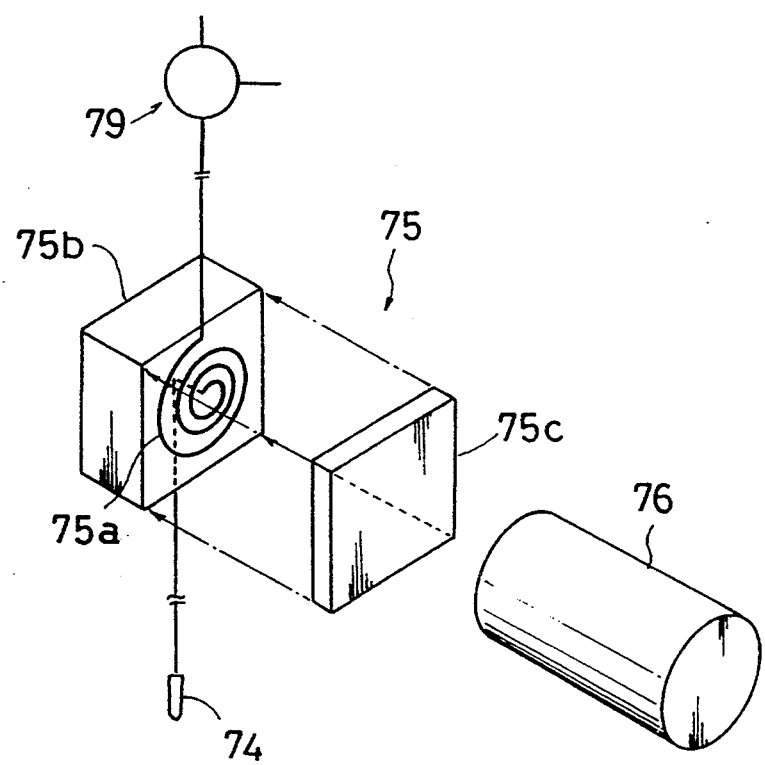

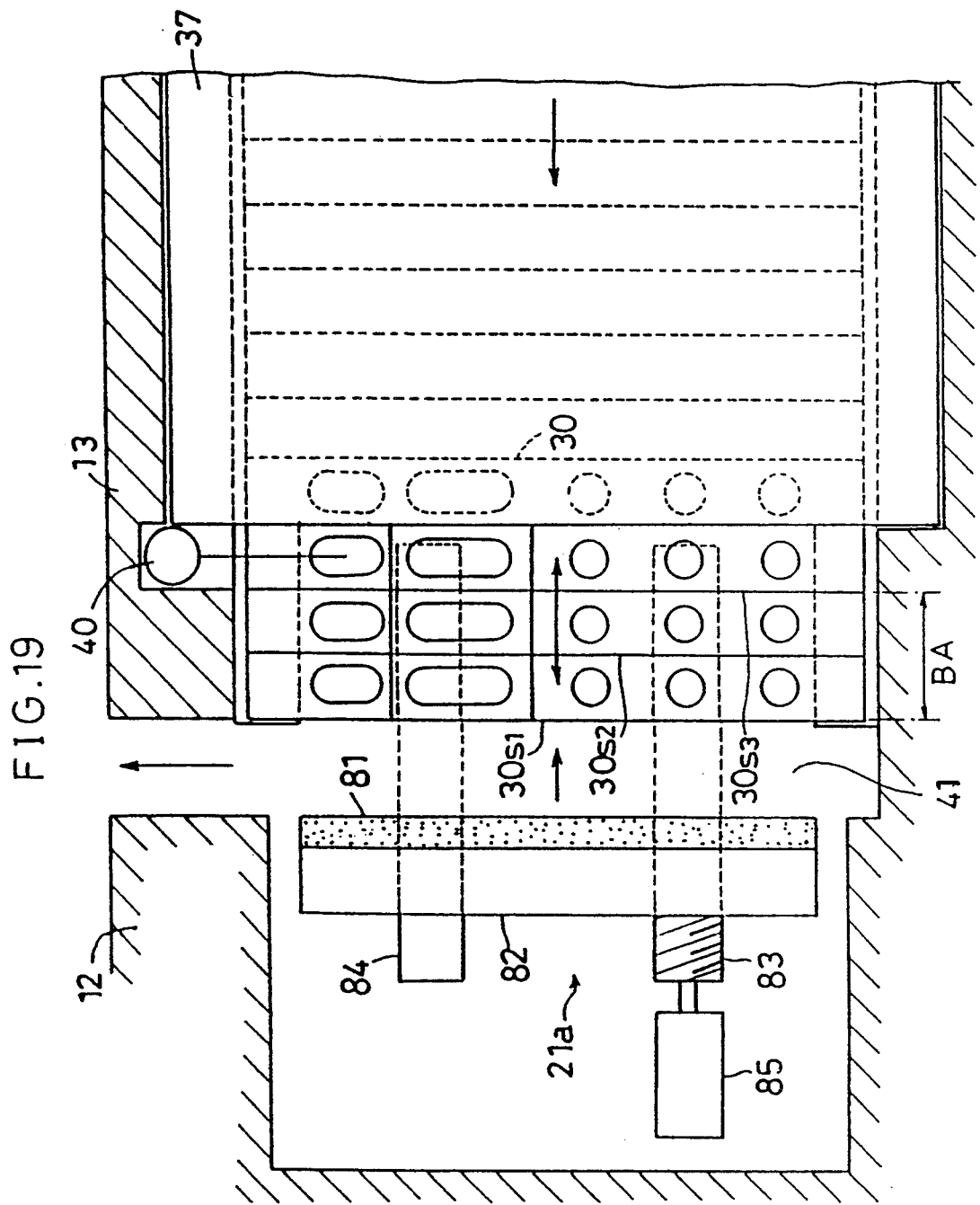

| A | B | C |
|---|---|---|
| A | B | D |
| A | B | E |
| A | B | F |
| A | C | D |
| A | C | E |
| A | C | F |
| A | D | E |
| A | D | F |
| A | E | F |
| B | C | D |
| B | C | E |
| B | C | F |
| B | D | E |
| B | D | F |
| B | E | F |
| C | D | E |
| C | D | F |
| C | E | F |
| D | E | F |

AUTOMATIC ANALYZING APPARATUS

BACKGROUND OF THE INVENTION (1) Field of the Invention

This invention relates to automatic analyzing apparatus for dispensing reagents selected according to examination items of specimens to cause reactions, and measuring and analyzing reaction mixtures resulting from a plurality of analytic processes. More particularly, the invention relates to an automatic analyzing apparatus for conducting examination on a plurality of items in parallel.

(2) Description of the Related Art

Conventional automatic analyzing apparatus have a construction based on a rotary disk system as disclosed in Japanese Patent Publications (Unexamined) Nos. 3-48161, 3-233362 and 3-186763, for example. Specifically, such an apparatus includes a specimen table, varied reagent tables, and an optical unit such as a photometric unit, absorptiometric unit or fluorophotometric unit, arranged according to analytic processes around a disk-shaped reaction table. The reaction table is rotated intermittently by predetermined amounts to transport reaction vessels placed peripherally of the reaction table to positions opposed to the respective units. In these positions specimens and reagents are placed in the vessels, and reaction mixtures are measured.

An exemplary case of analyzing 20 specimens with respect to three items (KK1, KK2 and KK3) will particularly be described with reference to FIG. 1. In this example, three reagents are successively dispensed for one analysis.

A reaction vessel supply mechanism, not shown, successively supplies reaction vessels P to peripheral positions on an upper surface of a disk-shaped reaction table 1. With intermittent rotation by predetermined amounts of the reaction table 1, the reaction vessels P placed thereon move successively through positions opposed to a specimen table 2 and reagent tables 3, 4 and 5 to a position opposed to a photometric unit 6.

The rotatable specimen table 2 supports 20 specimen vessels R1–R20 holding specimens S1–S20 to be analyzed, and specimen vessels RS1–RS3 holding sample specimens SS1–SS3 for use in an analytical curve correction to be described later. A movable nozzle 72 successively dispenses the specimens S1–S20 (when analyzing these specimens) or SS1–SS2 (when correcting analytical curves) into the respective reaction vessels P transported to the position opposed thereto.

Each of the rotatable reagent tables 3, 4 and 5 supports three reagent vessels Q31–Q33 holding reagents X31–X33, reagent vessels Q41–Q43 holding reagents X41–X43, or reagent vessels Q51–Q53 holding reagents X51–X53, for the respective analytic items KK1, KK2 and KK3. A movable nozzle 73, 74 or 75 successively dispenses the reagents X31–X33, X41–X43 or X51–X53 into the respective reaction vessels P transported to the position opposed thereto.

When analyzing the specimens, for example, the first reaction vessel P1 (for analytic item KK1) supplied to the reaction table 1 receives specimen S1 from the specimen table 2, reagent X31 from the reagent table 3, reagent X41 from the reagent table 4, and reagent X51 from the reagent table 5. The second reaction vessel P2 (for analytic item KK2) supplied to the reaction table 1 receives specimen S1 and reagents X32, X42 and X52. The third reaction vessel P3 (for analytic item KK3) receives specimen S1 and reagents X33, X43 and X53. The fourth reaction vessel P4 (for analytic item KK1) receives specimen S2 and reagents X31, X41 and X51. Thus, each of the specimens S1–S20 is placed in three of the reaction vessels P1–P60. Three reaction vessels (e.g. P1–P3) holding the same specimen (e.g. S1) are used in the analysis with respect to the three items (KK1, KK2 and KK3). Each of these reaction vessels (P1–P3) successively receives reagents for use in one analysis (for example, the reaction vessel P1 receives reagents X31, X41 and X51, the reaction vessel P2 receives reagents X32, X42 and X52, and the reaction vessel P3 receives reagents X33, X43 and X53.

The photometric unit 6 takes measurement, through each reaction vessel P, of a reaction mixture having completed a reaction therein. Based on a quantity of light (i.e. light emission from the reaction mixture) measured, the specimen is analyzed by determining the concentration of an objective component of the specimen.

The reaction vessels P having completed photometry are removed from the reaction table 1 by a discharge mechanism not shown. These vessels are cleaned for repeated use.

The reagent tables 3, 4 and 5 and photometric unit 6 are arranged and the intermittent rotation of the reaction table 1 is controlled to secure appropriate reaction periods. Consequently, a period of reaction between specimens S1–S20 and reagent X31 (X32 or X33) corresponds to a period of time from the dispensation of reagent X31 (or X32 or X33) in the position opposed to the reagent table 3 to the dispensation of reagent X41 (X42 or X43) in the position opposed to the reagent table 4, with rotation of the reaction table 1 occurring therebetween. Similarly, a period of reaction between specimen and reagent corresponds to a period of time from reagent table 4 to reagent table 5, or from reagent table 5 to photometric unit 6.

A way in which analytical curves are corrected with the analyzing apparatus having the above construction will be described next. The analytical curve refers to a relationship between a quantity of light emission determined through photometry from the reaction mixture resulting from dispensation of a predetermined reagent to a specimen and concentration of an objective component of the specimen. Correction of the analytical curve means correction of such a relationship.

Specifically, the analytical curve is the relationship between a quantity of light emission and concentration of an objective component of a specimen as represented by the solid line in FIG. 2. The analytical curve is used to derive concentration (e.g. x%) of an objective component of the specimen from a quantity of light emission (e.g. Lx) measured by the photometric unit 6.

However, the analytical curve can be inaccurate depending on the examination environment. To obtain a proper analytical curve, it is necessary to analyze a sample specimen prior to analyzing the objective specimen and correct a known analytical curve based on results of the analysis.

For example, the known analytical curve (solid line in FIG. 2) shows that a specimen of 50% concentration gives light emission L50. Assume that a sample specimen (50% concentration) gives light emission L'50. In this case, a new analytical curve is obtained by multiplying the light emission of the known analytical curve by L'50/L50. The new analytical curve obtained in this way is represented by the dotted line in FIG. 2. To carry out an accurate correction of the analytical curve, it is recommendable to use many sample specimens.

The case of conducting analysis on three items (KK1, KK2 and KK3) will now be considered.

As shown in FIG. 1, three reaction vessels P (PS1, PS2 and PS3) are successively supplied to the reaction table 1 prior to analyzing the objective specimens. When the reaction vessels PS1, PS2 and PS3 reach the specimen table 2, sample specimens SS1 (for analytic item KK1), SS2 (for analytic item KK2) and SS3 (for analytic item KK3) are dispensed into the reaction vessels PS1, PS2 and PS3, respectively. The reaction vessels PS1, PS2 and PS3 holding the sample specimens SS1, SS2 and SS3 then receive reagents corresponding to the respective analytic items from each of the reagent tables 3, 4 and 5. Thereafter the photometric unit 6 measures each of the sample specimens SS1, SS2 and SS3. Finally, as described hereinbefore, an analytical curve is corrected for each analytic item based on the result of photometry.

As noted hereinbefore, it is desirable to use many sample specimens in order to assure an accurate correction of the analytical curve. If, for example, two sample specimens are used for each analytic item, six reaction vessels P are used and each of the sample specimens SS1–SS3 is placed in two of each of the reaction vessels P. If three sample specimens are used for each analytic item, nine reaction vessels P are used.

However, the conventional automatic analyzing apparatus described above has the following drawbacks.

The drawbacks of the entirety of the apparatus will be cited first. Firstly, the conventional apparatus requires the specimen table 2, varied reagent tables 3, 4 and 5 and photometric unit 6 to be arranged around the reaction table 1. Thus, the apparatus has the disadvantage of being large (i.e. occupying a large floor area). With an increase in the number of reagents or in the number of items on which analysis is carried out, the reaction table 1 must be enlarged correspondingly, thereby occupying a still larger amount of floor space.

Secondly, the arrangement of specimen table 2, varied reagent tables 3, 4 and 5 and photometric unit 6 is designed, and the rotation of the reaction table 1 is controlled, according to the analytic items. To carry out analytic processes involving different reaction periods, for example, the arrangement of tables 2, 3, 4 and 5 and photometric unit 6 must be altered or the reaction table 1 must be rotated in different intermittent amounts. Further, where it is desired to change some of the reaction periods, the reagent tables or other components must be rearranged since a change in the intermittent rotation of the reaction table 1 would affect other reaction periods. Thus, the apparatus tends to perform only a single function, and lacks in versatility with respect to analyzing items and analyzing process conditions.

Thirdly, when a plurality of specimens are analyzed in parallel, it is difficult for the following reason to insert a specimen requiring an urgent treatment between the specimens being processed. Inserting a specimen requiring an urgent treatment between the specimens to which reagents have already been added is impossible since it would seriously affect the specimens being processed such as delaying the reaction time of the specimens to which the reagents have been added. If a specimen requiring an urgent treatment were inserted between other specimens before adding reagents thereto, the specimens and results of analysis could not be matched since the specimens are identified according to the order of treatment. A shift may be made in identification of the specimens to accommodate a specimen requiring an urgent treatment. However, each of the specimens following the inserted specimen must be shifted on the reaction table 1, for example, since otherwise these subsequent specimens could not be identified correctly. Such an insertion would necessitate a troublesome rearranging operation. Thus, it is simplest to put the specimen requiring an urgent treatment at the end of the specimens subjected to the analytic processes. This results in no urgent treatment.

Fourthly, in analyzing a plurality of specimens with respect to a plurality of items in parallel, the conventional apparatus carries out the analytic processes independently of one another, using the reaction vessels corresponding in number to the number of specimens multiplied by the number of items. It is difficult to reduce the processing time required to analyze all of the specimens.

The conventional apparatus has the following drawbacks relating to the dispensing units for dispensing reagents. Firstly, it is inevitable in the conventional apparatus to disperse the reagent vessels holding reagents, and movable nozzles are used for this reason. With an increase in the number of reagents, the number of movable nozzles must also be increased. Then the apparatus must be equipped with a plurality of nozzle drive mechanisms. This results in a complicated construction of the apparatus.

Secondly, certain reagents must be preserved in cold storage, and it is inefficient and uneconomical to keep such reagents in cold storage in a dispersed way as practiced heretofore since one apparatus must include a plurality of refrigerating mechanisms. Further, with the conventional movable nozzle system in which the nozzles make direct access to the reagent vessels, it is difficult to refrigerate the reagents in one place.

Thirdly, the movable nozzles make direct contact with the reagents in the reagent vessels, and covers of the reagent vessels must be kept open to allow access. As a result, the reagents could easily be contaminated or lost through evaporation.

Furthermore, the conventional apparatus has the following drawbacks relating to the optical unit. Firstly, the conventional optical unit carries out measurement of the reaction mixtures remaining in the reaction vessels. Even a slight stain on a surface of a reaction vessel would vary transmittance, thereby rendering accurate measurement impossible.

Secondly, the conventional optical unit takes measurement with a reaction vessel placed opposite a photodetecting element thereof. A slight deviation occurring when the reaction vessel is transported to the optical unit could result in a relative displacement between the vessel and photodetecting element. This makes uniform photometry impossible.

Thirdly, in the conventional apparatus, the reaction table 1 transports one reaction vessel after another to the photometric unit for measurement. Where, for example, a plurality of reaction vessels are subjected to photometry in parallel in order to reduce the processing time, it is difficult to maintain the photometric independence of each reaction vessel.

Fourthly, the conventional optical unit must have an inlet and an outlet for the reaction vessels to move into and out of the optical unit. Accurate photometry is impossible since it is difficult to seal off ambient light entering through the inlet and outlet.

There is a further drawback relating to the correction of an analytical curve. In order to correct the analytical curve accurately, it is necessary to use many sample specimens, which requires a correspondingly large number of reaction vessels. A processing time spent for the analytical curve correction corresponds to a period from the time at which the first reaction vessel for use in the analytical curve correction is delivered to the reaction table to the time at which the last reaction vessel used in the analytical curve correction is removed from the reaction table. Thus, an extended processing time is required to correct the analytical curve accurately.

SUMMARY OF THE INVENTION

The present invention has been made having regard to the state of the art noted above. The present invention has the following objects:

(1) To provide an automatic analyzing apparatus which is small in construction, consumes a reduced processing time for specimen analysis, is versatile with respect to analytic items, and readily allows insertion of an urgent treatment.

(2) To provide an automatic analyzing apparatus which allows reagents to be arranged collectively, carries out dispensing operations by means of a simple mechanism, and has dispensing units effective to diminish possibilities of reagent contamination and evaporation.

(3) To provide an automatic analyzing apparatus having an optical unit capable of accurate and uniform photometry free from the influences of reaction vessels, exhibiting a sufficient light shielding performance with ease, and assuring photometric independence of each reaction vessel when a plurality of reaction vessels are simultaneously subjected to photometry.

(4) To provide an automatic analyzing apparatus capable of correcting analytical curves accurately and quickly.

The above objects are fulfilled, according to the present invention, by an automatic analyzing apparatus for dispensing reagents according to examination items to specimens to cause reactions, and measuring and analyzing reaction mixtures finally obtained through a plurality of analytic processes, the apparatus comprising:

a plurality of cartridges each including, as integral parts thereof, at least one specimen tub for holding a specimen, and a plurality of reaction tubs for allowing analysis on a plurality of items to be conducted separately;

a transport device for transporting the cartridges in rectangular coordinate directions according to the analytic processes; and a multiple structural device including at least dispensing units and an optical unit for carrying out the analytic processes for the respective reaction tubs of the cartridges, the dispensing units and the optical unit being arranged in a multiple structure corresponding to the number of the reaction tubs for carrying out the analytic processes in parallel.

According to this apparatus, analysis may be carried out on a plurality of items for each cartridge, thereby reducing the time required for the analysis. The cartridges are transported in rectangular coordinate directions, which allows the apparatus to be designed compact and enables efficient use of a floor area. Further, since analysis is carried out cartridge by cartridge, any specimen requiring an urgent treatment may be cut in by accepting a cartridge for the urgent treatment before cartridges waiting for analytic processes. The cartridge cutting in for the urgent treatment and subsequent cartridges may readily be identified since the cartridges are treated separately.

The transport device may include a plurality of transport mechanisms for transporting the cartridges in selected directions within a three-dimensional space for the respective analytic processes, and for independently transporting the cartridges for the respective analytic processes. Then, a particular transport period (e.g. a transport period following dispensation of a certain reagent, which corresponds to a reaction period for this reagent) may be adjusted without affecting other transport periods (e.g. a transport period following dispensation of a different reagent, which corresponds to a reaction period for this different reagent). This feature provides the apparatus with versatility with respect to analyztic items and analytic process conditions.

Each dispensing unit may include a syringe, a cleaning buffer container, a reagent container, a first three-way valve, a second three-way valve and a dispensing nozzle. The syringe, the cleaning buffer container and the second three-way valve are connected to one another by piping through the first three-way valve to have a common port communicating with the syringe. The reagent container, the dispensing nozzle and the first three-way valve are connected to one another by piping through the second three-way valve to have a common port communicating with the first three-way valve. Each dispensing unit may further include a dispensation controller for causing the syringe to suck in a reagent from the reagent container, switching the first three-way valve and the second three-way valve, and causing the dispensing nozzle to dispense the reagent that was sucked in.

With this construction, the reagent container, the cleaning buffer container, the syringe controlled by the dispensation controller, and the respective three-way valves may be arranged freely by adjusting the piping interconnecting the syringe, cleaning buffer container, reagent container, first three-way valve, second three-way valve and dispensing nozzle. Consequently, the reagents may be disposed in one place, and reagent maintenance such as refrigeration of the reagents may be carried out in one place. Further, mechanisms for controlling reagent dispensation may be arranged in one place for localized control, which allows the apparatus to have a simplified construction. In addition, the dispensing nozzle is adapted to make no direct access to the reagent, thereby avoiding contamination of the reagent. The reagent is sucked from the reagent container through the fixed piping. Thus, the reagent container may be closed with a lid to avoid evaporation of the reagent.

Each dispensing unit may include a syringe, a cleaning buffer container, a plurality (n) of first to (n)th reagent containers, a first three-way valve and a plurality of (i) three-way valves, wherein (i) is a natural number from 2 to (n+1), and a dispensing nozzle. The syringe, the cleaning buffer container and the second three-way valve are connected to one another by piping through the first three-way valve to have a common port communicating with the syringe. The first reagent container, the third three-way valve and the first three-way valve are connected to one another by piping through the second three-way valve to have a common port communicating with the first three-way valve. The second reagent container, the fourth three-way valve and the second three-way valve are connected to one another by piping through the third three-way valve to have a common port communicating with the second three-way valve. The (n)th reagent container, the dispensing nozzle and the (n)th three-way valve are connected to one another by piping through the (n+1)th three-way valve to have a common port communicating with the (n)th three-way valve. Each dispensing unit may further include a dispensation controller for causing the syringe to suck a reagent from each of the reagent containers, switching the first to (n)th three-way valves, and causing the dispensing nozzle to dispense the reagent sucked. With this construction, a plural types of reagents may be dispensed through the single dispensing nozzle, besides the advantages of the foregoing dispensing unit. This feature provides the apparatus with versatility in that the single apparatus can perform analysis for plural types of combinations.

The optical unit may include a reaction mixture takeout device having a syringe, a cleaning buffer container and a nozzle connected to one another by piping through a three-way valve to have a common port communicating with the syringe, and a flow cell connected to an intermediate position of piping between the three-way valve and the nozzle, the flow cell being penetrable by light emitted from a reaction mixture sucked from each reaction tub of each cartridge and detained in the flow cell; a photodetecting device for detecting the light emitted from the reaction mixture detained in the flow cell; and a light shielding device for shutting off the flow cell and the photodetecting device from ambient light.

This construction carries out photometry accurately and uniformly without being influenced by transmittance of a reaction mixture passage and the like since the reaction mixture is drawn into the flow cell for photometry, and with the flow cell and photodetecting device fixed relative to each other and given a sufficient light shielding quality. Where a plurality of reaction mixtures are simultaneously subjected to photometry, reaction mixture takeout devices may be light-shielded individually to assure photometric independence of each reaction mixture.

The above apparatus may further comprise a specimen dispensing device for distributing the specimen placed in the specimen tub of each cartridge to predetermined reaction tubs of the cartridge; a moving device for moving the specimen dispensing device and the cartridge relative to each other in a direction of a next analytic process and in a direction opposite thereto; a specimen dispensation controller for controlling dispensation of sample specimens to the plurality (n which is a natural number 2 or more) cartridges such that the specimen dispensing device and each of the first to (n)th cartridges are moved relative to each other to distribute a first sample specimen placed in the specimen tub of the first cartridge to a first reaction tub of each of the first to (n)th cartridges, the specimen dispensing device and each of the cartridges are moved relative to each other to distribute a second sample specimen placed in the specimen tub of the second cartridge to a second reaction tub of each of the first to (n)th cartridges, and the first to (s)th (s being a natural number 2 or more and less than the number of reaction tubs) sample specimens placed in the specimen tubs of the first to (s)th cartridges are distributed to the first to (s)th reaction tubs of the first to (n)th cartridges; and an analytical curve correcting device for effecting an analytical curve correction based on results of measurement obtained from the predetermined analytic processes for the reaction tubs to which the sample specimens have been distributed.

With this construction, the first to (s)th sample specimens are distributed to the first to (s)th reaction tubs of a plurality (n) of cartridges. Each analytic process is carried out in parallel for the respective cartridges. The analytical curve correction is effected based on results of measurement obtained from the predetermined analytic processes for the reaction tubs to which the sample specimens have been distributed. The analytical curve correction for a plurality (s) of analytic items may be effected accurately by using the plurality (n) of sample specimens. The processing time is reduced compared with the apparatus which transports one reaction vessel after another for the analytical curve correction.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

FIGS. 6A and 6B are views showing operation of a specimen dispensing unit.

FIG. 11 is a view showing a construction of a flow cell in the photometric units.

FIG. 19 is a view showing a construction adjacent the specimen dispensing unit when carrying out the analytical curve correction.

DESCRIPTION OF THE PREFERRED EMBODIMENTS

Preferred embodiments of the present invention will be described in detail hereinafter with reference to the drawings.

FIRST EMBODIMENT

This and subsequent embodiments will be described in relation to an apparatus for use in immunoassay which is one example of an analyzing apparatus. It is to be understood, however, that the invention is equally applicable to other types of analyzing apparatus.

An immunoassay procedure may be outlined as follows:

(1) Dispense a specimen into a reaction vessel.
(2) Dispense a first reagent to this specimen. The first reagent is a magnetic microbead dispersion having antibodies reactive to antigens to be measured.
(3) Allow the antibodies to react to the antigens in the specimen for a predetermined period of time.
(4) Dispense a second reagent after removing unreacted components through bind/free (B/F) separation from a reaction mixture resulting from step (3) above. The second reagent is a dispersion of label antibodies reactive only to the antigens having reacted with the first reagent. The label antibodies act as a catalyst on a luminescent reagent described later.
(5) Allow the label antibodies to react to the antigens having reacted with the first reagent for a predetermined period of time.
(6) Again remove unreacted components through B/F separation from the reaction mixture. This B/F separation is repeated several times.
(7) Dispense the luminescent reagent to the reaction mixture resulting from step (6) above. Luminol is used as the luminescent reagent.
(8) Dispense hydrogen peroxide ($H_2O_2$).
(9) Analyze the specimen by photometry after a predetermined period of time.

Figure 3:
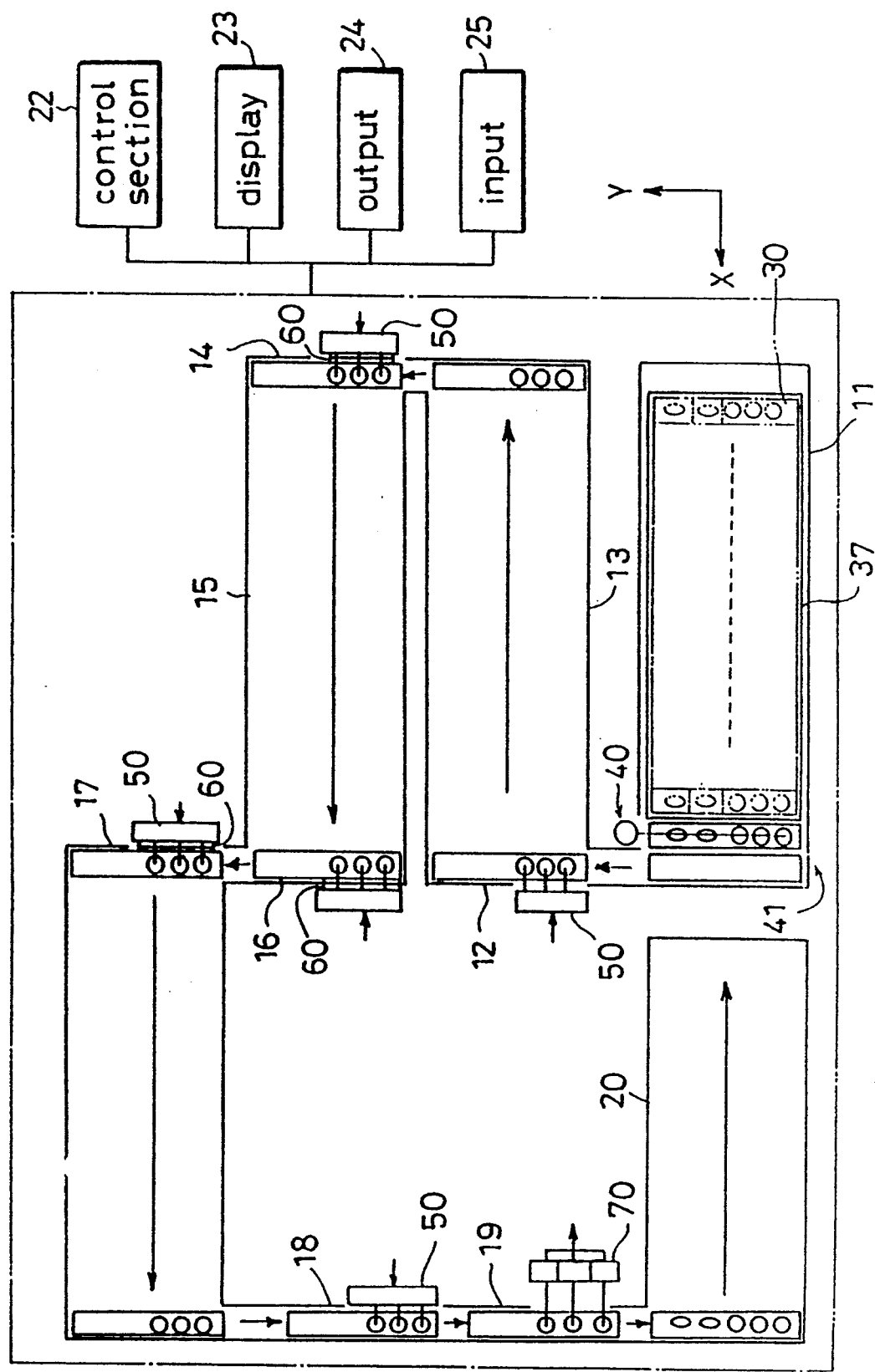
FIG. 3 is an overall plan view of an automatic analyzing apparatus in a first embodiment of the present invention.

An overall construction of an apparatus in a first embodiment of the invention will now be described with reference to FIG. 3. FIG. 3 is an overall plan view showing an outline of the apparatus in the first embodiment.

Broadly, this apparatus includes a cartridge standby section 11, a first reagent dispensing section 12, a first reaction path 13, a second reagent dispensing section 14, a second reaction path 15, an unreacted component removing section 16, a luminescent reagent dispensing section 17, a hydrogen peroxide dispensing section 18, a photometric section 19, a cartridge discharge section 20, a control section 22, a display device 23, an output device 24 and an input device 25.

Each of these sections and components will be particularly described hereinafter.

The cartridge standby section 11 includes a plurality of (e.g. 23) cartridges 30 containing specimens and standing by in a rack 37. A specimen dispensing unit 40 and an urgent cartridge receiver 41 are disposed adjacent a leading end of the cartridges 30 standing by. The cartridge standby section 11 further includes a heater, not shown, for preheating standby specimens to a predetermined temperature. The cartridges 30 are transported through the cartridge standby section 11 and subsequent sections by transport mechanisms to be described hereinafter.

Figure 4:
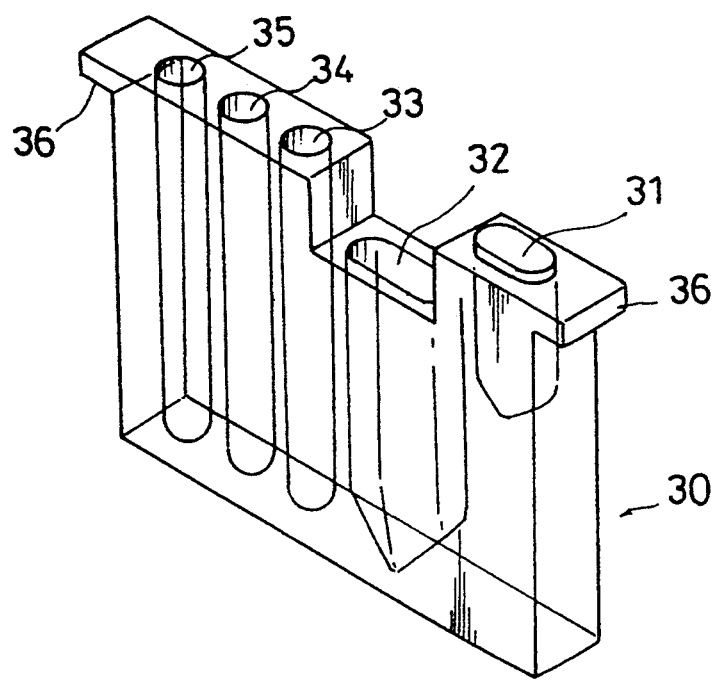
FIG. 4 is a perspective view of a cartridge.

A construction of cartridges 30 used in this embodiment will be described next with reference to FIG. 4. FIG. 4 is a perspective view of one cartridge 30.

Each cartridge 30 is formed of transparent polystyrene, and defines a specimen tub 31, a dilution tub 32 and three reaction tubs 33, 34 and 35 which are integral with one another. The specimen tub 31 receives a specimen such as serum. The dilution tub 32 is where the specimen is diluted. Each of the reaction tubs 33, 34 and 35 is where a reaction according to an examination item takes place. The cartridge 30 further defines flanges 36 at opposite upper ends thereof to be held during transport and to act as means to prevent the cartridge 30 from turning over. The specimen tub 31 has a larger width than the reaction tubs 33, 34 and 35 to facilitate entry of the specimen, and is formed shallow to facilitate visual observation of the presence or absence or the quantity of the specimen placed therein. Further, the specimen tub 31 has a projecting upper peripheral edge to prevent other specimens from mixing in from adjacent specimen tubs 31 when a plurality of cartridges 30 are arranged side by side and specimens are successively placed in the respective specimen tubs 31. The dilution tub 32 has an upper end thereof located at a lower level than those of the specimen tub 31 and reaction tubs 33, 34 and 35. This recess prevents missetting when the cartridge 30 is mounted in the rack 37 as described hereinafter. The recess also provides a reference for positioning the specimen tub 31 when a plurality of cartridges 30 are arranged side by side and specimens are successively placed in the respective specimen tubs 31, thereby to prevent the specimens from inadvertently being placed in the reaction tubs 35.

Figure 5:
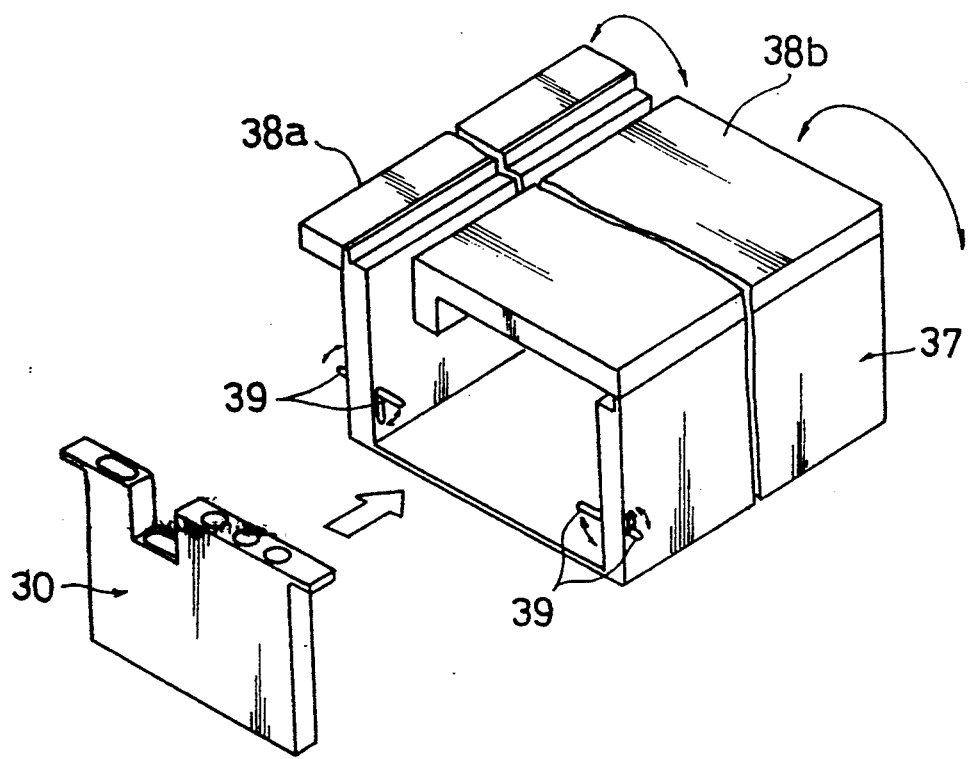
FIG. 5 is a perspective view of a rack for holding cartridges.

A construction of the rack 37 will be described next with reference to FIG. 5. FIG. 5 is a perspective view of the rack for holding the cartridges.

As shown in FIG. 5, the rack 37 includes openable upper lids 38a and 38b. The lid 38a acts to prevent evaporation of the specimens. The lid 38b seals the reaction tubs 33, 34 and 35 against entry of the specimens during an operation to place the specimens in the specimen tubs 31 after mounting the cartridges 30 in the rack 37. The upper lid 38b is bent inward at a forward end thereof to extend into the recess at the upper end of the dilution tub 32 of each cartridge 30 to prevent missetting of the cartridge 30 to the rack 37. Further, retainers 39 are provided adjacent opposite ends of the rack 37 to prevent the cartridges 30 from slipping off the rack 37 during transport. Each retainer 39 projects outwardly and inwardly of the rack 37, as shown in FIG. 5, when the rack 37 is not set to the cartridge standby section 11. The inwardly projecting portion of each retainer 39 contacts a cartridge 30 to hold the latter in place. When the rack 37 is set to the cartridge standby section 11, the outwardly projecting portion of each retainer 39 is pushed up by a contact element, not shown, provided in the cartridge standby section 11. At the same time, the inwardly projecting portion swings downward to release the cartridges 30. When the rack 37 is removed from the cartridge standby section 11, a spring mounted inside causes the retainer 37 to project outwardly and inwardly of the rack 37 again.

As shown in FIGS. 6A and 6B, the specimen dispensing unit 40 includes a movable nozzle 42 for sucking specimen A from the specimen tub 31 (FIG. 6A) and dispensing the specimen A sucked to certain of the reaction tubs 33, 34 and 35 (FIG. 6B). When the specimen A in the specimen tub 31 is to be diluted before dispensation to the reaction tubs 33, 34 and 35, the specimen A is dispensed to the dilution tub 32 first to be diluted with a diluent, and is thereafter dispensed to the reaction tubs 33, 34 and 35. The nozzle 42 is cleaned by a cleaning buffer, not shown, after a specimen dispensing operation for each cartridge 30.

The urgent cartridge receiver 41 is disposed between the specimen dispensing unit 40 and first reagent dispensing section 12 to provide an entrance for accepting a cartridge 30 containing a specimen requiring an urgent examination. This cartridge 30 is given priority over the cartridges 30 mounted in the rack 37 set to the cartridge standby section 11. When a cartridge for an urgent examination is to cut in, an emergency interrupt command is given from the input device 25 which will be described hereinafter. With this command, the other cartridges 30 are pushed backward, counter to a direction of transport, by a push-back mechanism described hereinafter, to allow the cartridge for an urgent examination to be accepted to the receiver 41. When the cartridge for the urgent examination enters the receiver 41, this cartridge also is pushed back by the push-back mechanism to a position opposed to the specimen dispensing unit 40. Then, the specimen is distributed from the specimen tub 31 to the reaction tubs 33, 34 and 35 as described above, which is followed by the same examination processes.

The first reagent dispensing section 12 includes a reagent dispensing unit 50. The reagent dispensing unit 50 dispenses the first reagent according to an examination item to each of the reaction tubs 33, 34 and 35 of the cartridges 30 transported from the cartridge standby section 11.

Figure 7B:
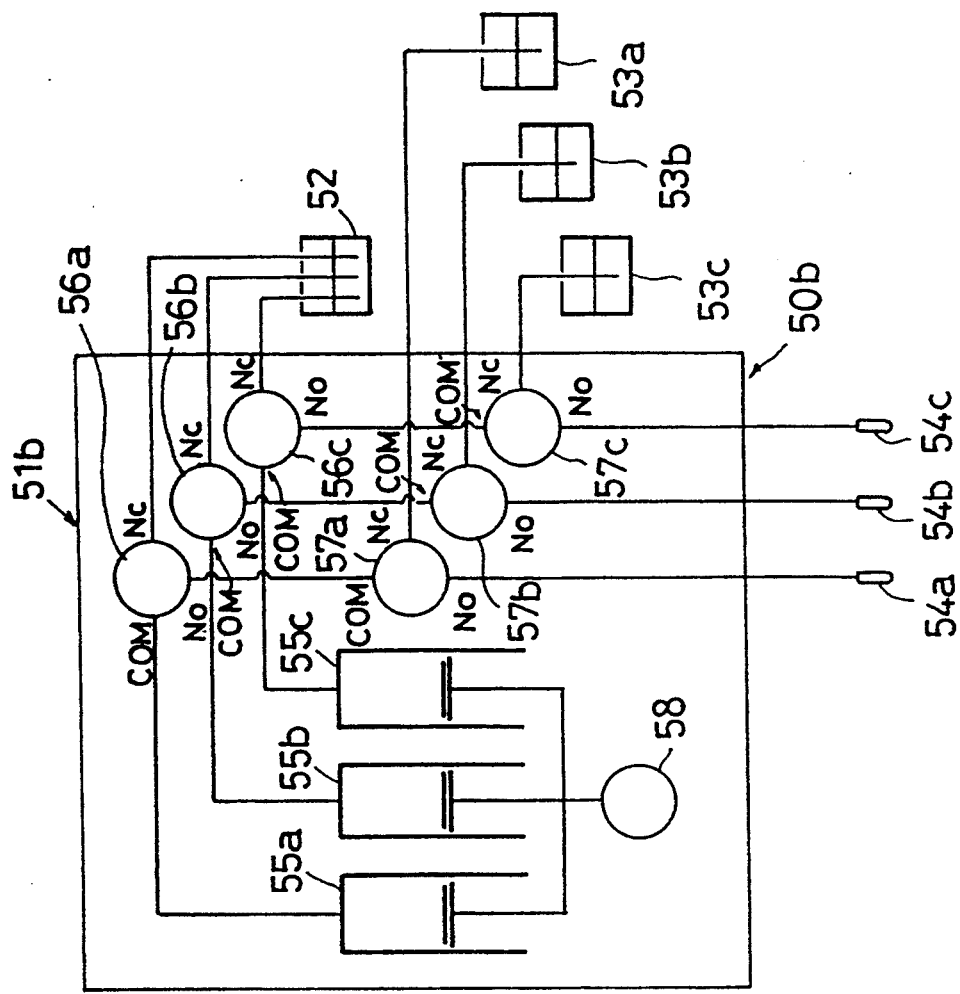
FIGS. 7A and 7B are views showing constructions of reagent dispensing units.
Figure 7A:
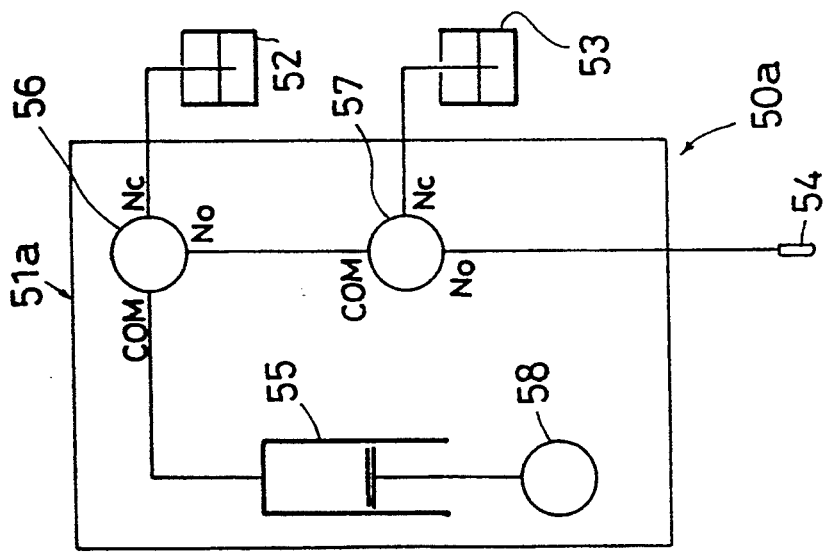

Constructions of the reagent dispensing unit 50 will be described with reference to FIGS. 7A and 7B. FIG. 7A schematically shows a reagent dispensing unit 50a having a simple structure. FIG. 7B schematically shows a reagent dispensing unit 50b having a multiple structure.

The reagent dispensing unit 50a having a simple structure will be described first.

The reagent dispensing unit 50a having a simple structure includes a dispensation controller 51a, a cleaning buffer container 52, a reagent container 53 and a dispensing nozzle 54. The dispensation controller 51a includes a syringe 55, a pulse motor 58 and three-way valves 56 and 57.

In the reagent dispensing unit 50a, the syringe 55, cleaning buffer container 52 and three-way valve 57 are connected to one another by piping through the three-way valve 56 to have a common port COM communicating with the syringe 55. Further, the reagent container 53, dispensing nozzle 54 and three-way valve 56 are connected to one another by piping through the three-way valve 57 to have a common port COM communicating with the three-way valve 56. The syringe 55 is operable by the pulse motor 58. Preferably, the three-way valves 56 and 57 comprise pinch valves which are electromagnetically switchable. Each common port COM is connected to a normally open port NO when the valve is de-energized, and to a normally closed port NC when the valve is energized.

A quantity of reagent transmitted through the piping by operation of the syringe 55 (i.e. operation of the pulse motor 58) is proportional to a capacity of the piping. Thus, lengths of the piping interconnecting adjacent components are determined based on the capacity. If, for example, the piping between the three-way valve 57 and reagent container 53 of a certain reagent dispensing unit 50 has a sectional area M1 (cm$^2$), its length L1 is determined so that L1 multiplied by M1 equals a predetermined reference value. As described hereinafter, this apparatus employs a plurality of reagent dispensing units 50. By determining lengths of piping in the respective reagent dispensing units 50 based on its capacity as above, operating amounts of the syringes 55 may be made uniform, thereby simplifying control of the apparatus. Besides, when a plurality of apparatus are manufactured, operating amounts of the syringes 55 of the respective apparatus may be uniformed. The apparatus may then use a unified program of operating sequence of the control section 22 for controlling dispensing operations as described hereinafter. This aspect contributes toward improved productivity of the apparatus. The piping between the three-way valve 57 and reagent container 53 may advantageously be spiraled to prevent the reagent from settling in this piping.

A first reagent dispensing sequence of the reagent dispensing unit 50a having the simple structure as noted above will be described hereinafter. This dispensing operation is controlled by the control section 22 described later.

(1) Prior to dispensation, the piping from the reagent container 53 to the three-way valve 57 is filled with the reagent, while other piping including the syringe 55 is filled with the cleaning buffer.

(2) The pulse motor 58 is driven to pull the syringe 55 and suck air from a tip end of the dispensing nozzle 54. The pulse motor 58 is stopped when the air has advanced a predetermined amount past the common port COM of the three-way valve 57.

(3) The three-way valve 57 is switched to communicate the common port COM with the reagent container 53.

(4) The pulse motor 58 is driven to pull the syringe 55 and suck toward the common port COM a quantity of the reagent to be dispensed.

(5) The three-way valve 57 is switched to communicate the common port COM with the dispensing nozzle 54.

(6) The pulse motor 58 is driven to push the syringe 55 and dispense the reagent sucked.

After the predetermined quantity of reagent is dispensed to a reaction tub and the cartridge 30 is transported to the next examination process, the pulse motor 58 is driven to push the syringe 55 and dispense the cleaning buffer through the dispensing nozzle 54 to clean the latter.

The air is sucked to a point of a predetermined amount past the common port COM of the three-way valve 57 at step (2) above, in order to prevent the reagent sucked at step (4) from mixing with the cleaning buffer.

A second reagent dispensing sequence will be described next.

In the second sequence, after steps (1) through (3) of the first sequence, step (4) is taken to suck the reagent in a predetermined quantity plus the quantity to be dispensed. After step (5) and before step (6), part of the excess reagent sucked is dispensed through the dispensing nozzle 54 to be discarded, then the desired quantity of reagent is dispensed to a reaction tub, and finally the remainder of the excess reagent is dispensed through the dispensing nozzle 54 to be discarded. This dispensing operation is controlled by the control section 22 described later.

In this way, the parts of the reagent preceding and succeeding the part actually dispensed to a specimen are discarded. Even if the cleaning buffer remains in the piping, the buffer will mix with the parts of reagent to be discarded, without lowering the concentration of the part of reagent dispensed to the specimen.

Also in the multiple structure described hereinafter for simultaneously dispensing different reagents to the three reaction tubs 33, 34 and 35, the parts of reagent preceding and succeeding the part actually dispensed to each specimen are discarded. This discarding operation absorbs influences of any variations in the reagents sucked to be dispensed to the respective reaction tubs 33, 34 and 35, and any variations in the time taken for the reagents to reach tip ends of dispensing nozzles 54 due to variations in the capacity of piping from three-way valves 57 to the dispensing nozzles 54. This always enables a simultaneous dispensation of desired quantities of reagents to the respective specimens.

The piping may be adjusted when incorporating the reagent dispensing unit 50a into the apparatus, whereby, for example, a plurality of dispensing nozzles 54 may be arranged in selected positions, and the dispensation controller 51a, cleaning buffer container 52 and reagent container 53 may be arranged freely. This realizes a space-saving arrangement and allows the apparatus to be compact. It is also possible to have reagent containers 53 arranged close together to enable a localized refrigeration, for example, thereby to achieve efficient running of the apparatus.

In the first embodiment, each cartridge 30 has three reaction tubs 33, 34 and 35. Thus, three of the above reagent dispensing unit 50a having a simple structure may be provided for use as a multiple structure.

When incorporating such reagent dispensing units 50 into the first reagent dispensing section 12, a plurality of dispensing nozzles 54 are arranged in positions suited to dispense reagents into the respective reaction tubs 33, 34 and 35 of the cartridges 30 transported thereto.

The reagent dispensing unit 50b having a multiple structure will be described next with reference to FIG. 7B.

The reagent dispensing unit 50b having a multiple structure includes a dispensation controller 51b, a cleaning buffer container 52, reagent containers 53a, 53b and 53c, and dispensing nozzles 54a, 54b and 54c. The dispensation controller 51b includes syringes 55a, 55b and 55c, a pulse motor 58 and three-way valves 56a, 57a, 56b, 57b, 56c and 57c.

In this reagent dispensing unit 50b, the respective reagent containers 53a, 53b and 53c are connected to the associated dispensing nozzles 54a, 54b and 54c, cleaning buffer container 52 and syringes 55a, 55b and 55c through the three-way valves 56a, 57a, 56b, 57b, 56c and 57c, as in the reagent dispensing unit 50a having a simple structure. The cleaning buffer container 52 and pulse motor 58 are shared. The three-way valves 56a, 57a, 56b, 57b, 56c and 57c have the same construction as in the reagent dispensing unit 50a having a simple structure. Piping lengths are determined based on the pipe capacity as in the reagent dispensing unit 50a. This contributes toward simplification and improved productivity of the apparatus, and besides allows the reagents to be dispensed in a uniform and accurate quantity by means of the single pulse motor 58.

In the above reagent dispensing unit 50b having a multiple structure, the reagents are dispensed in the same way as in the reagent dispensing unit 50a having a simple structure described earlier. That is, the three-way valves 56a, 57a, 56b, 57b, 56c and 57c are switched for the respective reagent containers 53a, 53b and 53c.

The reagent dispensing unit 50b may be arranged in a way similar to the preceding reagent dispensing unit 50a having a simple structure, which allows the apparatus to be compact. The reagent dispensing unit 50b is incorporated into the first reagent dispensing section 12, with the dispensing nozzles 54a, 54b and 54c arranged in positions suited to dispense the reagents into the respective reaction tubs 33, 34 and 35 of the cartridges 30.

The construction including a plurality of reagent dispensing units 50a having a simple structure to correspond to the number of reaction tubs, and the reagent dispensing unit 50b having a multiple structure corresponding to the number of reaction tubs, both correspond to the multiple structure of the device (dispensing unit) according to the present invention.

Next, the first reaction path 13 is a line for allowing the first reagent dispensed to the respective reaction tubs 33, 34 and 35 in the first reagent dispensing section 12 to undergo a reaction for a predetermined period of time. The cartridges 30 entering the first reaction path 13 are successively transported toward the second reagent dispensing section 14. After the predetermined reaction period, the cartridges 30 are successively transported to the second reagent dispensing section 14.

The second reagent dispensing section 14 includes an unreacted component removing unit 60 and a reagent dispensing unit 50. The unreacted component removing unit 60 removes components not having reacted to the first reagent through B/F separation from the reaction mixture in each of the reaction tubs 33, 34 and 35 of the cartridges 30 transported from the first reaction path 13. The reagent dispensing unit 50 dispenses the second reagent according to an examination item to the reaction mixture in each of the reaction tubs 33, 34 and 35 from which the unreacted components have been removed by the unreacted component removing unit 60.

The unreacted component removing unit 60 includes a magnet and a reaction mixture suction unit.

Figure 8A:
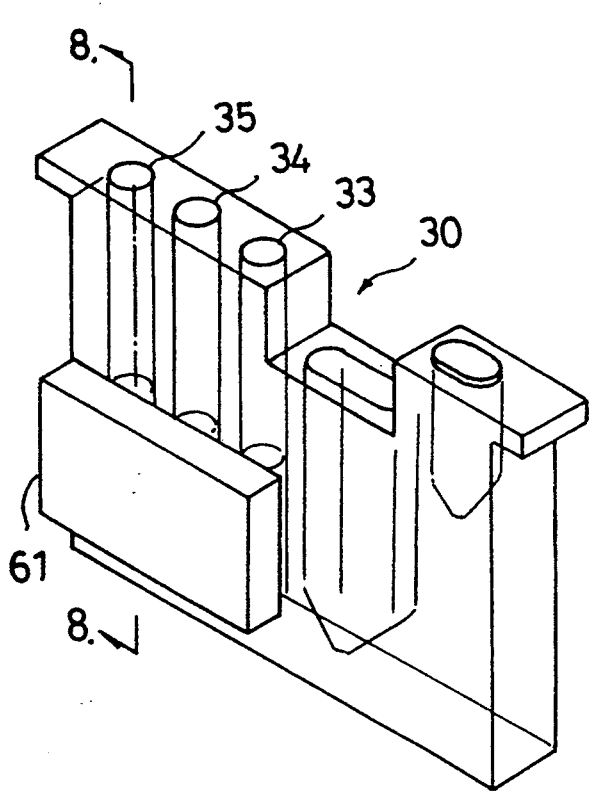
FIGS. 8A, 8B and 8C are views showing a sequence of B/F separation.
Figure 8B:
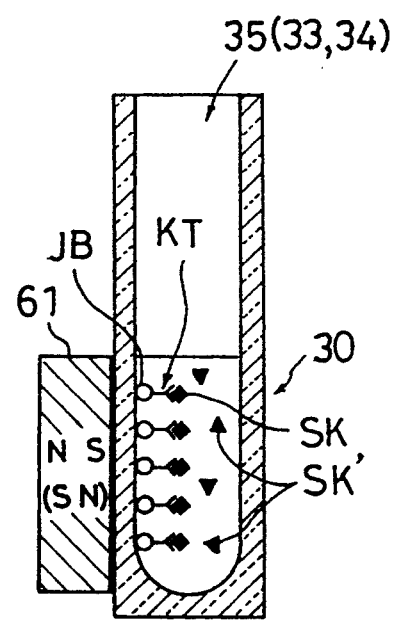
Figure 8C:
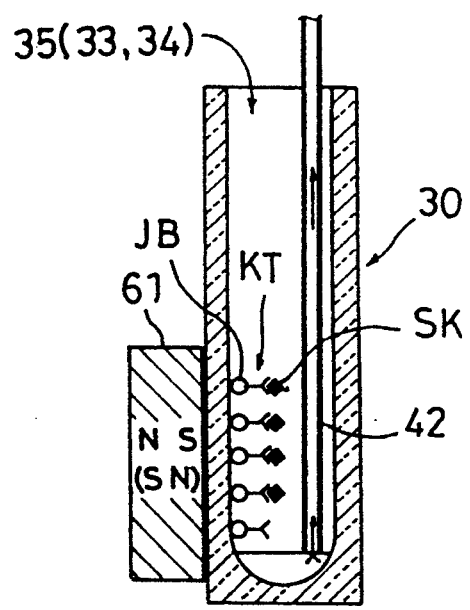

As shown in FIG. 8A, a magnet 61 contacts outer walls of the reaction tubs 33, 34 and 35 of the cartridge 30. As shown in FIG. 8B (a section taken on line 8—8 of FIG. 8A), the magnet 61 is polarized to N and S or S and N to attract magnetic microbeads in the first reagent dispensed to each reaction tub 35 (33, 34). The reaction mixture suction unit has the same construction as the specimen dispensing unit 40 described hereinbefore. As shown in FIG. 8C, the suction unit sucks the reaction mixture through a nozzle 42 extending into each reaction tub 35 (33, 34). At this time, antigens SK having reacted to the first reagent (antibodies KT included in the magnetic microbeads) are retained in each reaction tub 35 (33, 34), while magnetic portions JB attracted to the magnet 61, and other antigens SK' are removed with the reaction mixture.

Figure 9A:
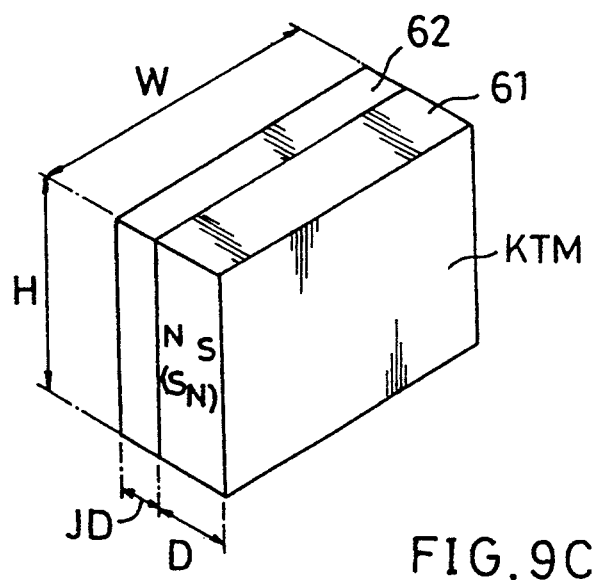
FIGS. 9A, 9B and 9C are views showing constructions of a magnet used in an unreacted component removing unit.
Figures 9B, 9C:
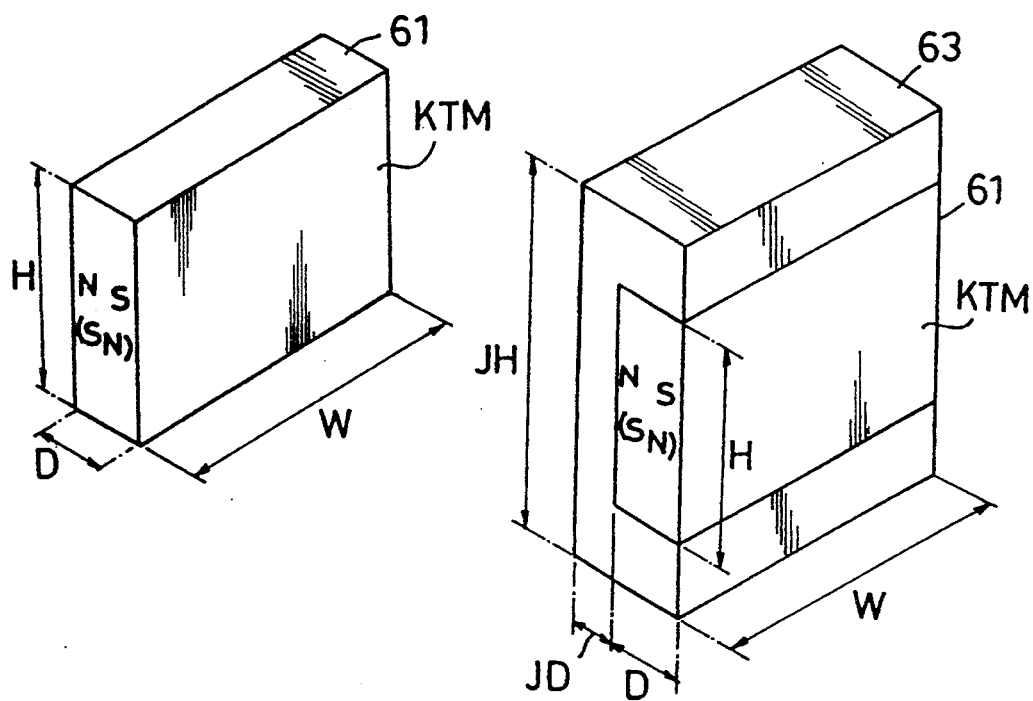

The magnet 61 used in the unreacted component removing unit 60 has a surface KTM opposed to the reaction tubs 33, 34 and 35 (see FIGS. 8B and 8C). As shown in FIG. 9A, a magnetic substance 62 such as iron, permalloy or the like may be applied, for example, to a back surface of the magnet 61 with respect to the surface KTM. This construction increases the magnetic force applied from the surface KTM opposed to the reaction tubs 33, 34 and 35. Where, as shown in FIG. 9B, for example, the magnet 61 has a height H of 15 mm, a depth D of 5 mm and a width of 21 mm, the magnet 61 produces a magnetic force of 2.2kGauss from the surface KTM opposed to the reaction tubs 33, 34 and 35. Where the magnetic substance 62 which has a depth JD of 3 mm is applied to the same magnet 61 (see FIG. 9A), the magnet 61 produces a magnetic force of 3.2kGauss from the surface KTM opposed to the reaction tubs 33, 34 and 35.

That is, to obtain the same magnetic force (e.g. 2.2kGauss), the magnet 61 (with the magnetic substance 62) may be reduced in size, which allows the apparatus to be compact. With the magnet 61 of the same size, the magnetic force may be increased, Then, the magnetic microbeads JB having reacted to the antigens KS to be measured are attracted at an increased rate to expedite the analytic processes. Further, the precision of B/F separation may be enhanced since the magnetic microbeads JB having reacted to the antigens KS to be measured are attracted with increased precision.

As shown in FIG. 9C, a channel-shaped magnetic substance 63 (e.g. iron, permalloy or the like) may be fitted on the magnet 61 to surround three surfaces thereof, i.e. two lateral surfaces on opposite sides of the surface KTM opposed to the reaction tubs 33, 34 and 35, and the back surface remote from the surface KTM opposed to the reaction tubs 33, 34 and 35. This construction increases still further the magnetic force applied from the surface KTM opposed to the reaction tubs 33, 34 and 35. Where, for example, the magnet 61 has a height H of 15 mm, a depth D of 5 mm and a width of 21 mm, which is covered by the magnetic substance 63 having a height JH of 25 mm and a depth JD of 3 mm, the magnet 61 produces a magnetic force of 4.3kGauss from the surface KTM opposed to the reaction tubs 33, 34 and 35.

Thus, the apparatus may be further reduced in size, while expediting the analytic processes and enhancing the precision of B/F separation. The three surfaces of the magnet 61 may contact the magnetic substance 62, or may be slightly spaced therefrom. However, it is preferable that the back surface remote from the surface KTM opposed to the reaction tubs 33, 34 and 35 is in contact with the magnetic substance 62.

The reagent dispensing unit 50 is the same as in the first reagent dispensing section 12 and will not be described again.

The second reaction path 15 is a line for allowing the second reagent dispensed to the respective reaction tubs 33, 34 and 35 in the second reagent dispensing section 14 to undergo a reaction for a predetermined period of time. The second reaction path 15 is the same in construction as the first reaction path 13, and will not particularly be described here.

The unreacted component removing section 16 includes an unreacted component removing unit 60. The unreacted component removing unit 60 removes components not having reacted to the second reagent through B/F separation from the reaction mixture in each of the reaction tubs 33, 34 and 35 of the cartridges 30 transported from the second reaction path 15. The unreacted component removing unit 60 is the same as in the second reagent dispensing section 14, and will not be described again.

The luminescent reagent dispensing section 17 includes an unreacted component removing unit 60 and a reagent dispensing unit 50. The reagent dispensing unit 50 dispenses the luminescent reagent to the reaction mixture in each of the reaction tubs 33, 34 and 35 from which the unreacted components have been removed in the unreacted component removing section 16 and further unreacted components have been removed by the unreacted component removing unit 60. The unreacted component removing unit 60 is the same as in the second reagent dispensing section 14, and the reagent dispensing unit 50 is the same as in the first reagent dispensing section 12. Thus, these units 60 and 50 are not described here.

The hydrogen peroxide dispensing section 18 includes a reagent dispensing unit 50. This reagent dispensing unit 50 dispenses hydrogen peroxide to the reaction mixture in each of the reaction tubs 33, 34 and 35 of the cartridges 30 to which the luminescent reagent has been dispensed in the luminescent reagent dispensing section 17. The reagent dispensing unit 50 is the same as in the first reagent dispensing section 12 and will not be described again.

The photometric section 19 includes a photometric unit 70. The photometric unit 70 measures light emitted from the reaction mixture in each of the reaction tubs 33, 34 and 35 of the cartridges 30 having undergone the examination processes up to the hydrogen peroxide dispensing section 18.

Figure 10B:
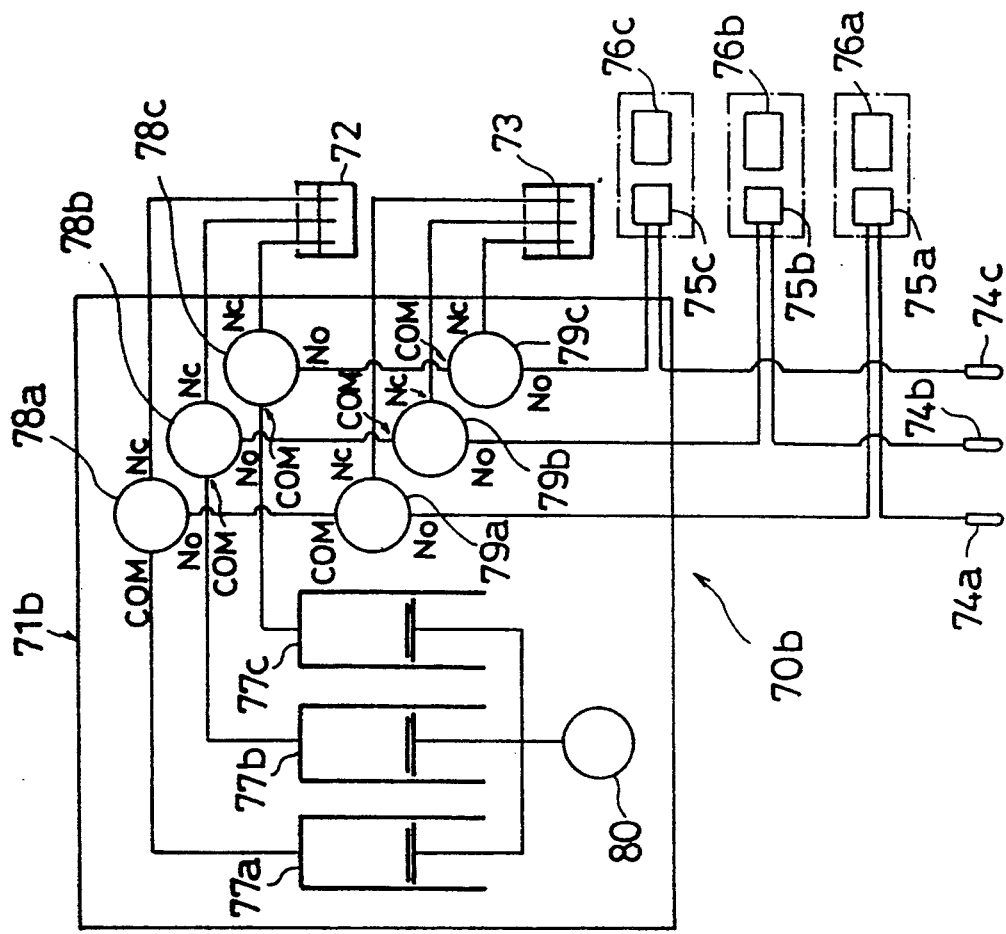
FIGS. 10A and 10B are views showing constructions of photometric units.
Figure 10A:
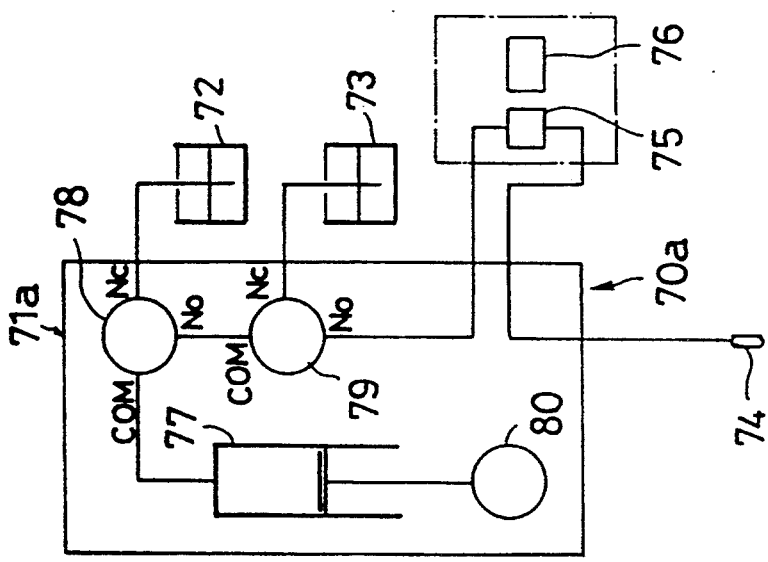

Constructions of the photometric unit 70 will be described with reference to FIGS. 10A and 10B. FIG. 10A schematically shows a photometric unit 70a having a simple structure. FIG. 10B schematically shows a photometric unit 70b having a multiple structure.

The photometric unit 70a having a simple structure will be described first.

The photometric unit 70a having a simple structure includes a photometry controller 71a, cleaning buffer containers 72 and 73, a nozzle 74, a flow cell 75 and a photodetecting element 76. The photometry controller 71a includes a syringe 77, a pulse motor 80 and three-way valves 78 and 79.

In the photometric unit 70a, the syringe 77, cleaning buffer container 72 and three-way valve 79 are connected to one another by piping through the three-way valve 78 to have a common port COM communicating with the syringe 77. Further, the cleaning buffer container 73, flow cell 75 and three-way valve 78 are connected to one another by piping through the three-way valve 79 to have a common port COM communicating with the three-way valve 78. The nozzle 74 is connected by piping to an end of the flow cell 75 not connected to the three-way valve 79. The photodetecting element 76 is disposed opposite the flow cell 75. The flow cell 75 and photodetecting element 76 are sealed by a light shielding material. The syringe 77 is operable by the pulse motor 80. Preferably, the three-way valves 78 and 79 comprise pinch valves which are electromagnetically switchable. Each common port COM is connected to a normally open port NO when the valve is de-energized, and to a normally closed port NC when the valve is energized. A quantity of reagent transmitted through the piping by operation of the syringe 77 (i.e. operation of the pulse motor 80) is proportional to a capacity of the piping. Thus, lengths of the piping interconnecting adjacent components are determined based on the capacity. If, for example, the piping between the flow cell 75 and nozzle 74 of a certain photometric unit 70 has a sectional area M2 (cm$^2$), its length L2 is determined so that L2 multiplied by M2 equals a predetermined quantity. Thus, when a plurality of apparatus are manufactured, operating amounts of the syringes 77 of the respective apparatus may be made uniform. The apparatus may then use a unified program of operating sequence of the control section 22 for controlling photometric operations as described hereinafter. This aspect contributes toward improved productivity of the apparatus. Two types of cleaning buffers are used, one of which is used in cleaning the flow cell 75 and the other in cleaning the nozzle 74. As shown in FIG. 11, the flow cell 75 includes a wound transparent tube 75a embedded in a fluororesin box 75b with a luminescent surface exposed therefrom, and a quartz plate 75c pressed on the luminescent surface to fix the tube 75a in place.

A photometric sequence of the photometric unit 70a having a simple structure as noted above will be described hereinafter. This photometric operation is controlled by the control section 22 described later.

(1) The pulse motor 80 is driven to pull the syringe 77 and suck the reaction mixture from a tip end of the nozzle 74. The pulse motor 80 is stopped when a predetermined quantity of reaction mixture has been drawn into the flow cell 75.

(2) The photodetecting element 76 detects light emitted from the reaction mixture drawn into the flow cell 75. Data of the light detected by the photodetecting element 76 are transmitted to the control section 22.

(3) Upon completion of photometry, the pulse motor 80 is driven to push the syringe 77 and discard the reaction mixture drawn, and to clean the flow cell 75, piping and nozzle 74 with the cleaning buffers.

The piping may be adjusted when incorporating the photometric unit 70a into the apparatus, whereby the photometry controller 71a and cleaning buffer containers 72 and 73 may be arranged freely. This realizes a space-saving arrangement and allows the apparatus to be compact.

In the first embodiment, each cartridge 30 has three reaction tubs 33, 34 and 35. Thus, three of the above photometric unit 70a having a simple structure may be provided for use as a multiple structure.

When incorporating such photometric units 70 into the photometric section 19, a plurality of nozzles 74 are arranged in positions suited to suck the reaction mixtures from the respective reaction tubs 33, 34 and 35 of the cartridges 30 transported thereto.

The photometric unit 70b having a multiple structure will be described next with reference to FIG. 10B.

The photometric unit 70b having a multiple structure includes a photometry controller 71a, cleaning buffer containers 72 and 73, nozzles 74a, 74b and 74c, flow cells 75a, 75b and 75c, and photodetecting elements 76a, 76b and 76c. The photometry controller 71b includes syringes 77a, 77b and 77c, a pulse motor 80 and three-way valves 78a, 79a, 78b, 79b, 78c and 79c.

In this photometric unit 70b, the respective flow cells 75a, 75b and 75c are connected to the associated nozzles 74a, 74b and 74c, cleaning buffer containers 72 and 73 and syringes 77a, 77b and 77c through the three-way valves 78a, 79a, 78b, 79b, 78c and 79c, as in the photometric unit 70a having a simple structure. The photodetecting elements 76a, 76b and 76c are provided for the flow cells 75a, 75b and 75c, respectively, each combination being sealed by a light shielding material. The cleaning buffer container 72 and 73 and pulse motor 80 are shared. The three-way valves 78a, 79a, 78b, 79b, 78c and 79c have the same construction as in the photometric unit 70a having a simple structure. Piping lengths are determined based on the pipe capacity as in the photometric unit 70a. This contributes toward simplification and improved productivity of the apparatus, and besides allows the reaction mixtures to be measured accurately by means of the single pulse motor 80.

In the above photometric unit 70b having a multiple structure, the photometric process is conducted in the same way as in the photometric unit 70a having a simple structure described earlier. That is, the three-way valves 78a, 79a, 78b, 79b, 78c and 79c are switched for the respective flow cells 75a, 75b and 75c.

The photometric unit 70b may be arranged in a way similar to the preceding photometric unit 70a having a simple structure, which allows the apparatus to be compact.

The construction including a plurality of photometric units 70a having a simple structure to correspond to the number of reaction tubs, and the photometric unit 70b having a multiple structure corresponding to the number of reaction tubs, both correspond to the multiple structure of the device (photometric unit) according to the present invention.

The cartridges discharge section 20 is where the cartridges 30 having undergone the photometric process in the photometric section 19 are discharged successively and left standing by.

The transport mechanism for transporting cartridges 30 through each of the foregoing sections will be described next.

The transport mechanism is provided in each of the cartridge standby section 11, first reagent dispensing section 12, first reaction path 13, second reagent dispensing section 14, second reaction path 15, unreacted component removing section 16, luminescent reagent dispensing section 17, hydrogen peroxide dispensing section 18, photometric section 19 and cartridge discharge section 20. These transport mechanisms transport the cartridges 30 in rectangular coordinate directions (X and Y directions) through the examination processes from the cartridge standby section 11 to the cartridge discharge section 20.

Figure 12:
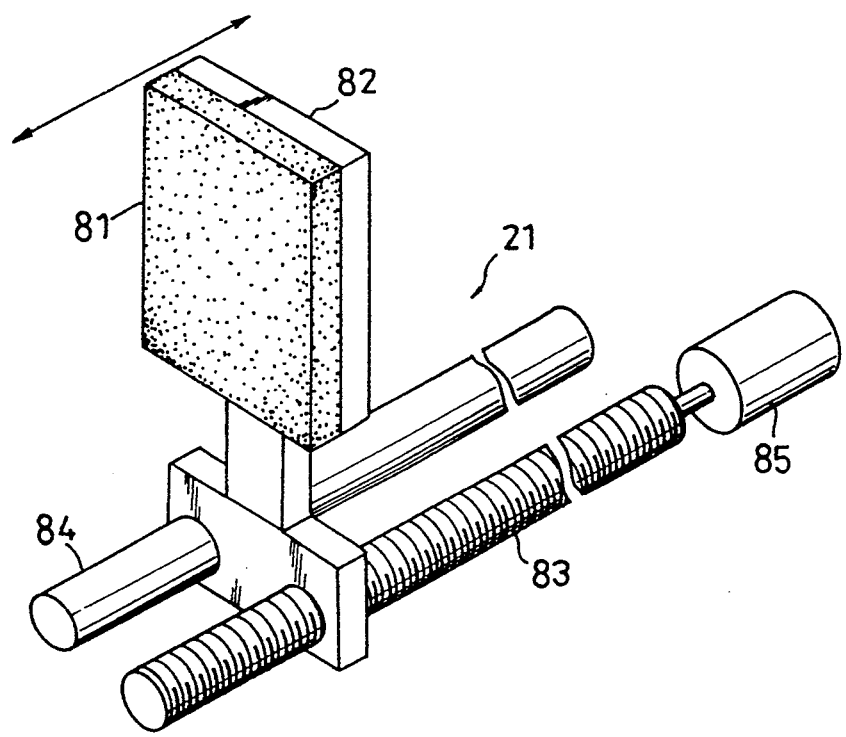
FIG. 12 is a perspective view showing an outline of a transport mechanism.
Figure 13:
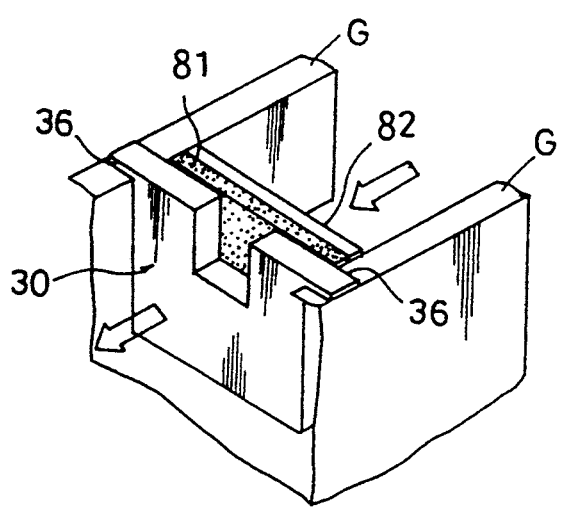
FIG. 13 is a view showing a cartridge transported in the X direction.

A construction of the transport mechanism will be described with reference to FIGS. 12 and 13. FIG. 12 is a perspective view showing an outline of the transport mechanism. FIG. 13 is a view showing a cartridge 30 transported in the X direction.

Referring to the drawings, a transport mechanism 21 includes a pusher 82 having a silicone rubber 81 bonded thereto. The pusher 82 is meshed with a screw shaft 83 and fitted on a guide shaft 84. The screw shaft 83 is rigidly connected to a rotary shaft of a motor 85. Thus, the screw shaft 83 is rotatable with opposite rotations of the motor 85 to drive the pusher 82 in directions indicated by arrows. Each cartridge 30 transported is pushed by the pusher 82.

How the transport mechanism 21 transports the cartridge 30 in the X direction will be described with reference to FIG. 13.

The cartridge 30 is transported in the X direction through the first reaction path 13, for example, after the first reagent is dispensed thereto in the first reagent dispensing section 12. During the transport the cartridge 30 is contacted and pushed by the silicone rubber 81 from behind.

As shown in FIG. 13, the cartridge 30 in transport has the flanges 36 at the opposite upper ends thereof resting on guides G provided in the first reaction path 13.

How the transport mechanism 21 transports the cartridge 30 in the Y direction will be described next.

The cartridge 30 is transported in the Y direction, for example, from the end of the first reaction path 13 to the second reagent dispensing section 14 as follows.

The guides G are not provided at the end of the first reaction path 13, and the cartridge 30 transported thereto becomes disengaged from the guides G. In this state, a transport mechanism 21 having a pusher 82 movable in the Y direction places a silicone rubber 81 in contact with a side of the cartridge 30. Then the pusher 82 is driven to push the cartridge 30 in the Y direction.

The cartridge 30 disengaged from the guides G and transported in the Y direction is fed so that the cartridge 30 will again be supported by guides G for subsequent transport in the X direction. For example, when the cartridge 30 is fed from the second reagent dispensing section 14 (where the cartridge 30 is not supported by guides G) to the second reaction path 15 (where the cartridge 30 is supported by guides G), the cartridge 30 mounts on the guides G by way of ramps formed at ends of the guides G.

Figure 14:
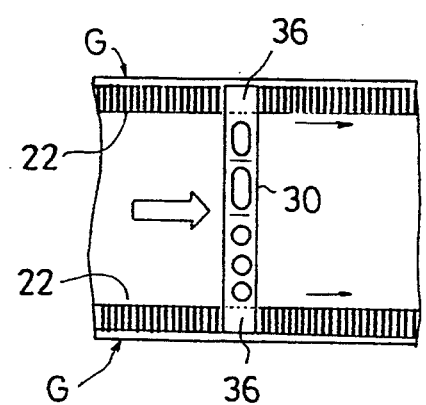
FIG. 14 is a view showing a modified transport mechanism.

The transport mechanism in the first reaction path 13 or second reaction path 15 may be modified as shown in FIG. 14, in which belt conveyors 22 are provided in place of the guides G. In this construction, the cartridge 30 is transported with the flanges 36 thereof resting on the belt conveyors 22.

A reaction period for each cartridge 30 elapses in the first reaction path 13 or second reaction path 15 as follows.

Where, for example, the transport mechanism 21 shown in FIGS. 12 and 13 is used, the cartridges 30 having received the first reagent are successively pushed out to and allowed to stand by in a predetermined position in the first reaction path 13. When a certain cartridge 30 is standing by in the predetermined position in the first reaction path 13, a next cartridge 30 is pushed out to that position to push the standing cartridge 30 one step forward, Thus, cartridges 30 successively fed into the first reaction path 13 push the standing cartridges 30 step by step to the end of the first reaction path 13. Then, unreacted components are removed from each cartridge 30 in the second reagent dispensing section 14. The above-mentioned predetermined position in the first reaction path 13 is adjustable so that the reaction period of the first reagent elapses precisely at the time of unreacted component removal. This method will particularly be described in the second embodiment herein.

Where the transport mechanism shown in FIG. 14 is used, the cartridges 30 fed into the first reaction path 13 are transported at a predetermined rate. The rate of transport by the transport mechanism (belt conveyors 22) is adjusted so that the reaction period of the first reagent elapses precisely at the time of unreacted component removal in the second reagent dispensing section 14. By adjusting the transport rate, the apparatus in this embodiment may be used in different examinations requiring different reaction periods. Where only the reaction period of the first reagent (standby period in the first reaction path 13) is varied, this reaction period may be adjusted without affecting transport periods through the reaction paths where the reaction periods of other reagents (e.g. the second reagent) are allowed to elapse. This feature affords versatility to the apparatus.

The push-back mechanism used for accepting a cartridge for an urgent examination has a construction similar to the above transport mechanism 21 (FIG. 12), for example. That is, a pusher 82 having a silicone rubber 81 bonded thereto is placed opposite the specimen dispensing unit 40 across the urgent cartridge receiver 41. When pushing back the cartridges 30, the motor 85 is rotated to drive the pusher 82 toward the specimen dispensing unit 40.

The control section 22 is connected to the dispensation controllers 51a or 51b of the respective reagent dispensing units 50, the unreacted component removing units 60, the photometry controller 71a or 71b of the photometric unit 70, the transport mechanisms 21, the display device 23, the output device 24 and the input device 25. The control section 22 controls the foregoing operations of the varied sections and units according to examination information inputted through the input device 25, causes results of photometry by the photometric unit 70 to be displayed on the display device 23, and outputs the results to the output device 24. Further, the control section 22 recognizes identities of the cartridges 30 used in the examination according to an order in which the examination information is input in relation to an order in which the cartridges 30 stand by in the cartridge standby section 11. If an emergency cut-in occurs, the control section 22 processes the sequence according to emergency cut-in information inputted by the operator. The examination information mentioned above is information including the type and number of examination items, for example. The specimens placed in the cartridges 30 are examined according to the examination information. For example, certain cartridges may be subjected to a three-item examination, while other cartridges are subjected to a two-item examination, and still other cartridges are subjected to a one-item examination. The emergency cut-in information, for example, indicates a place in which a cartridge requiring an urgent examination has been inserted, as counted from the foremost cartridge. This information is used for identification purposes. The cartridges 30 may be identified by means other than the above, such as by bar code labels applied to the cartridges 30.

The control section 22 includes a CPU (central processing unit), a memory and a ROM (read-only memory). The ROM stores a program for executing the above processing sequence. When the apparatus is started, the program is read from the ROM and stored in the memory for execution by the CPU. Alternatively, the program may be stored in a flexible disk (hereinafter "F/D"). Where an F/D is used, the program is read upon start of the apparatus from the F/D set to an F/D drive connected. This program is stored in the memory for execution by the CPU.

The display device 23 comprises a CRT, a liquid crystal display panel or the like. The output device 24 comprises a printer or the like. The input device 25 comprises a keyboard or the like.

Figure 15:
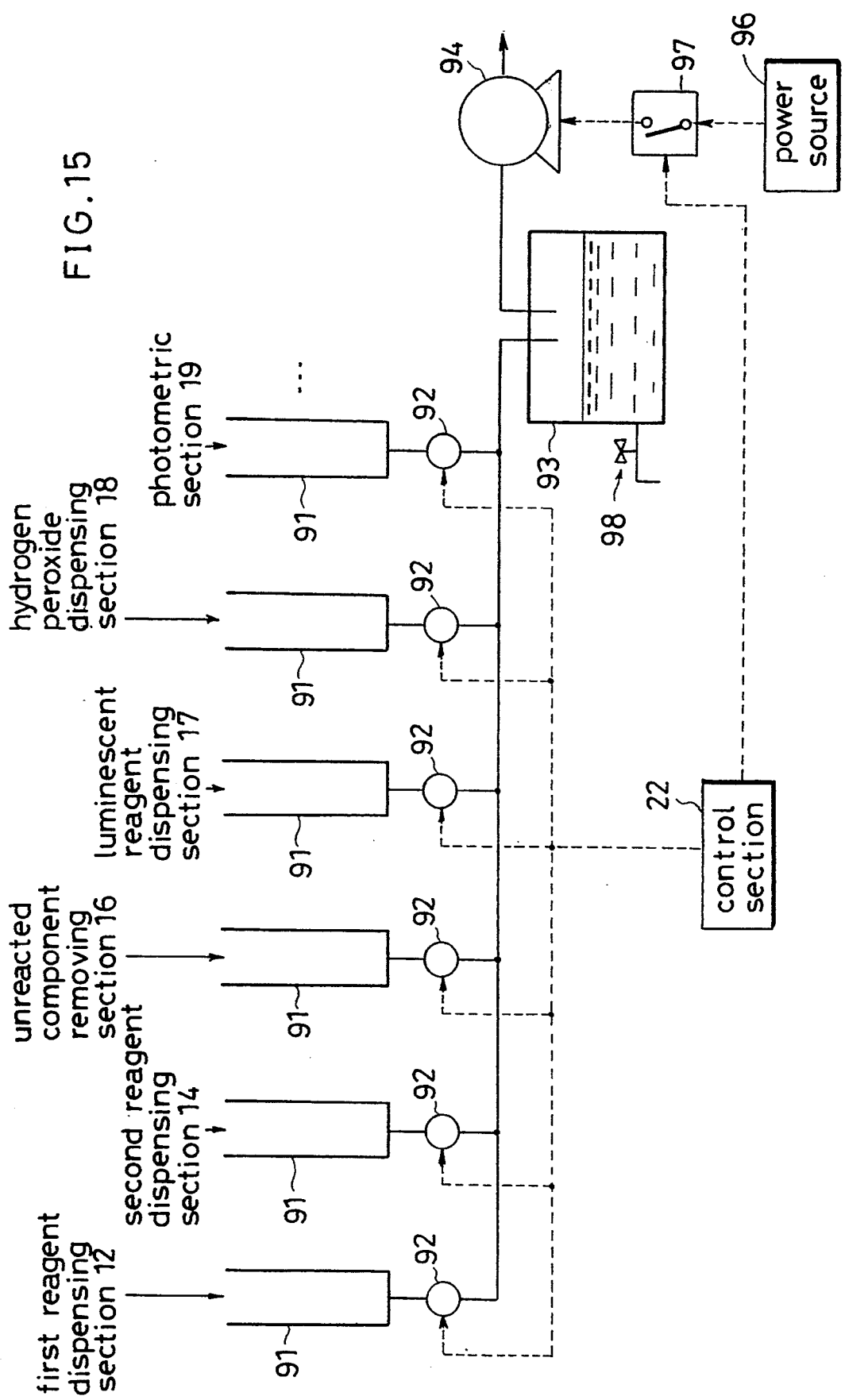
FIG. 15 is a view showing a waste disposal system.

As shown in FIG. 15, waste tubs 91 are provided for temporarily storing waste liquids such as the reaction mixtures drawn by reaction mixture suction units in the unreacted component removing units 60 included in the second reagent dispensing section 14, unreacted component removing section 16 and luminescent reagent dispensing section 17; the reagents discarded when the reagents are dispensed in the second reagent dispensing sequence by the reagent dispensing units 50 included in the first reagent dispensing section 12, second reagent dispensing section 14, luminescent reagent dispensing section 17 and hydrogen peroxide dispensing section 18; the reaction mixtures discarded after photometry by the photometric unit 70 included in the photometric section 19; and the cleaning buffers used in the respective units. The waste tubs 91 are connected at exhaust ends thereof through valves 92 to a waste tank 93.

The waste tank 93 is decompressible by a vacuum pump 94. The vacuum pump 94 is driven by a power source 96 which is controlled by ON/Off operations of a switch 97. The switch 97 and valves 92 are operated by the control section 22.

When the switch 97 is turned on with the valves 92 closed (to stop the waste liquids flowing from the waste tubs 91 to the waste tank 93), the vacuum pump 94 is driven to decompress the waste tank 93. Conversely, when the switch 97 is turned off with the valves 92 opened, the vacuum pump 94 is stopped to cancel the decompression. At this time, the waste tank 93 communicates with the ambient through the valves 92, whereby the interior of the waste tank 93 returns to atmospheric pressure.

With the above construction, for transferring the waste liquids stored in the waste tubs 91 to the waste tank 93, the control section 22 closes the valves 92 and turns on the switch 97 to decompress the waste tank 93. The valves 92 are opened as necessary when the waste liquids stored in the waste tubs 91 exceed a predetermined quantity. As a result, the waste liquids are drawn at high speed from the waste tubs 91 into the decompressed waste tank 93. When all the waste liquids have been transferred from the waste tubs 91 to the waste tank 93, the control section 22 closes the valves 92.

When draining the waste liquids stored in the waste tank 93, the control section 22 opens the valves 92 and turns off the switch 97 to return the waste tank 93 to atmospheric pressure. Then, the operator opens a cock 98 provided for the waste tank 93 to drain the waste liquids from the waste tank 93. Since the waste tank 93 has returned to atmospheric pressure through the valves 92 by this time, the waste liquids are drained more easily and quickly than when the interior of the waste tank 93 is at a lower pressure than atmospheric pressure.

As described hereinafter with reference to a flowchart (FIG. 17), when the operator inputs a command to start examination, the control section 22 closes the valves 92 and turns on the switch 97 to decompress the waste tank 93. The valves 92 are opened as appropriate during the examination processes to transfer the waste liquids collected in the waste tubs 91 to the waste tank 93. After the examination is completed, the valves 92 are opened and the switch 97 is turned off to allow the waste liquids to be exhausted from the waste tank 93 at high speed.

With the control section 22 operating the switch 97 on and off as above, preparations and the like may automatically be effected for the transfer of waste liquids from the respective waste tubs 91 to the waste tank 93, and for the high speed drainage of the waste liquids from the waste tank 93. The vacuum pump 94 is driven only when necessary, thereby diminishing noise of the vacuum pump 94. Particularly since the processes are automatically carried out from start to finish of the examination, the operator may leave the apparatus, thereby to be free from the noise of the vacuum pump 94.

Figure 16:
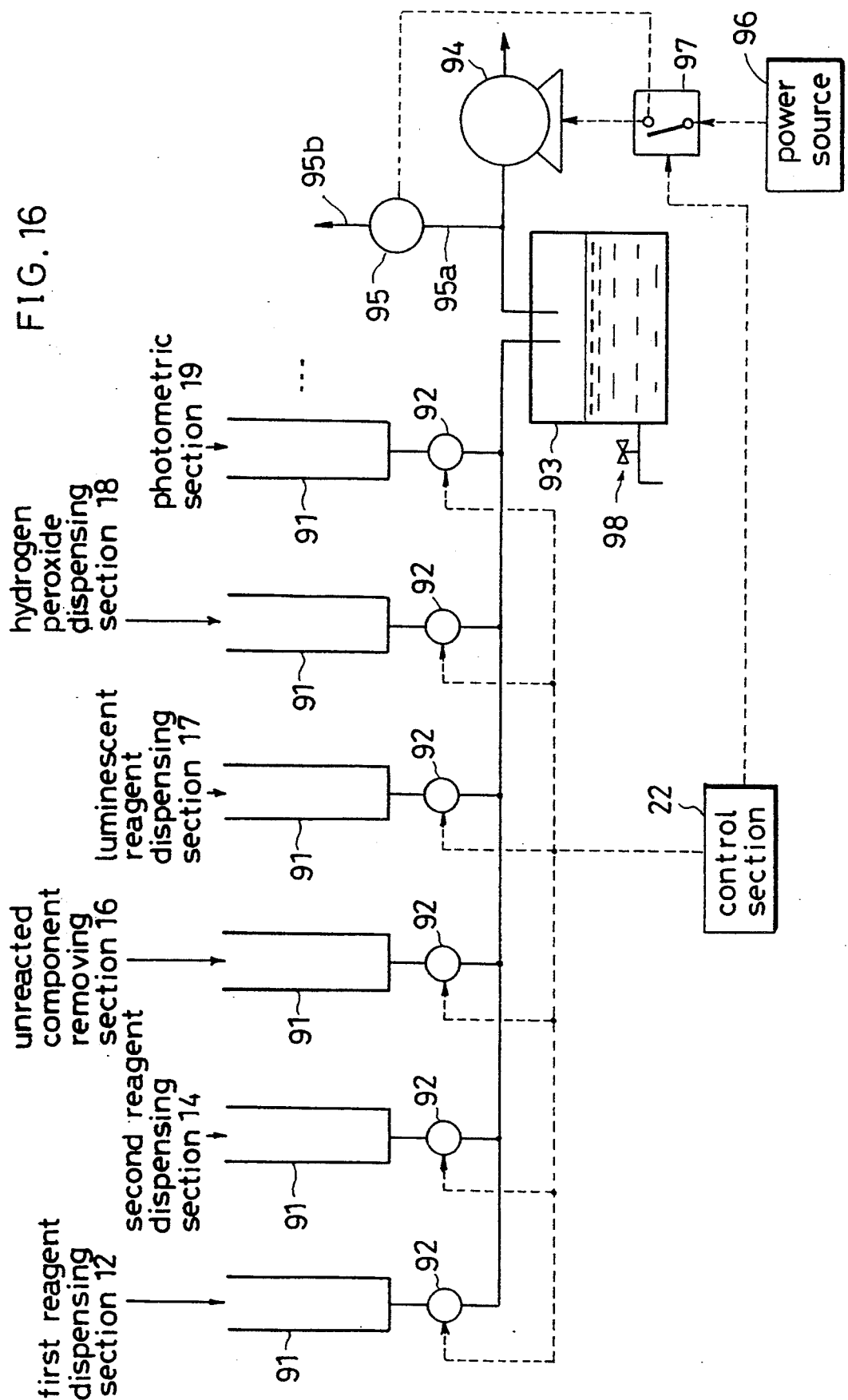
FIG. 16 is a view showing a modified waste disposal system.

The mechanism for disposing of the waste liquids from the respective units may be constructed as shown in FIG. 16 as distinct from the construction shown in FIG. 15.

Referring to FIG. 16, the waste liquids are temporarily stored in waste tubs 91 which are connected at exhaust ends thereof through valves 92 to a waste tank 93.

The waste tank 93 is decompressible by a vacuum pump 94. A pipe 95a branched off from a position between the waste tank 93 and vacuum pump 94 is connected to an electromagnetic valve 95 to which a pipe 95 having an open end is connected. The electromagnetic valve 95 is operable by ON/OFF operations of a switch 97 which also controls a power source 96 for driving the vacuum pump 94 (the pipes 95a and 95b being closed when the switch 97 is turned on).

When the switch 97 is turned on with the valves 92 closed, the electromagnetic valve 95 is closed and the vacuum pump 94 is driven to decompress the waste tank 93. Conversely, when the switch 97 is turned off, the vacuum pump 94 is stopped and the electromagnetic valve 95 is opened to cancel the decompression by the vacuum pump 94. At this time, the waste tank 93 communicates with the ambient through the electromagnetic valve 95, whereby the interior of the waste tank 93 returns to atmospheric pressure.

The valves 92 and switch 97 are operated by the control section 22.

With the above construction, for transferring the waste liquids stored in the waste tubs 91 to the waste tank 93, the control section 22 closes the valves 92 and turns on the switch 97 to decompress the waste tank 93. Subsequently, the valves 92 are opened. As a result, the waste liquids are drawn at high speed from the waste tubs 91 into the decompressed waste tank 93. When all the waste liquids have been transferred from the waste tubs 91 to the waste tank 93, the control section 22 closes the valves 92.

When draining the waste liquids stored in the waste tank 93, the control section 22 closes the valves 92 and turns off the switch 97 to return the waste tank 93 to atmospheric pressure. Then, the operator opens a cock 98 provided for the waste tank 93 to drain the waste liquids from the waste tank 93. Since the waste tank 93 has returned to atmospheric pressure through the electromagnetic valve 95 by this time, the waste liquids are drained more easily than when the interior of the waste tank 93 is at a lower pressure than atmospheric pressure. If the cock 98 were opened with the interior of the waste tank 93 remaining at a lower pressure than atmospheric, air would enter through a drain port and the waste liquids in the waste tank 93 would evaporate and flow into the vacuum pump 94. The vacuum pump 94 could thereby become rusted. With the above construction, however, the waste tank 93 returns to atmospheric pressure simultaneously with stoppage of the vacuum pump 94. In addition, dry ambient air may be allowed to directly enter the waste tank 93 and piping. Consequently, decompressed moist air is prevented from entering the vacuum pump 94, thereby avoiding deterioration of the vacuum pump 94.

As described hereinafter with reference to the flowchart (FIG. 17), when the operator inputs a command to start examination, the control section 22 closes the valves 92 and turns on the switch 97 to decompress the waste tank 93. The valves 92 are opened as appropriate during the examination processes to transfer the waste liquids collected in the waste tubs 91 to the waste tank 93. After the examination is completed, the valves 92 are closed and the switch 97 is turned off to allow the waste liquids to be exhausted from the waste tank 93. With the control section 22 operating the switch 97 on and off as above, the varied processes may be carried out automatically. The vacuum pump 94 is driven only when necessary, thereby diminishing noise of the vacuum pump 94. Particularly since the processes are automatically carried out from start to finish of the examination, the operator may leave the apparatus, thereby to be free from the noise of the vacuum pump 94.

Figure 17:
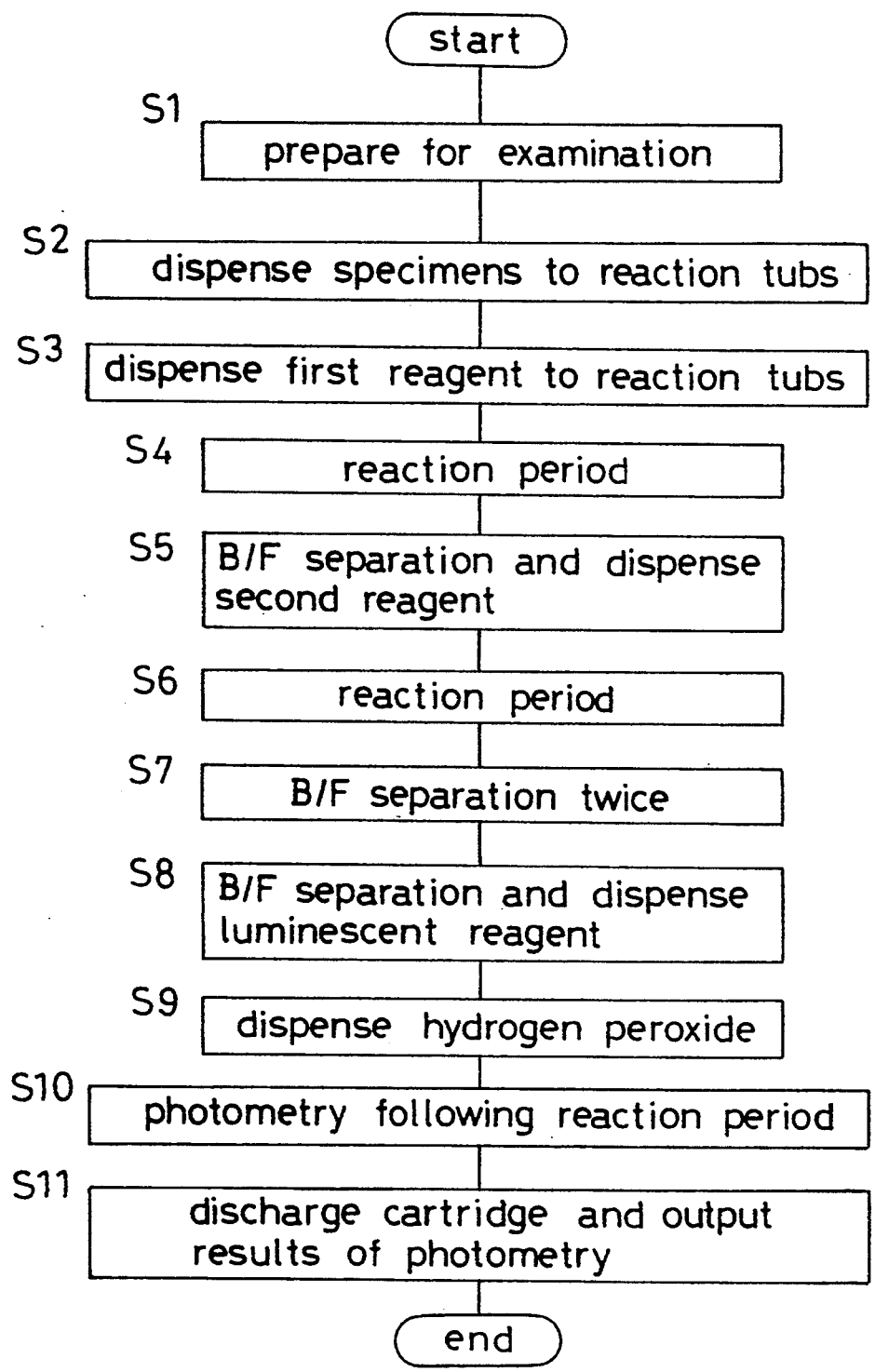
FIG. 17 is a flow chart showing the operations of the apparatus in the first embodiment to carry out examination processes.

Operations of the apparatus in the first embodiment to carry out the examination processes will be described with reference to the flowchart shown in FIG. 17.

First, at step S1, preparations are made for an examination. These preparations include placing cartridges 30 used in the examination in the rack 37, setting the cartridges 30 to the cartridge standby section 11, and inputting examination information on these cartridges 30 through the input device 25. After inputting the examination information, a command is given to start the examination.

For the cartridges 30 for which the examination has started, the specimen dispensing unit 40 distributes the specimen in a predetermined quantity from the specimen tub 31 to each of the reaction tubs 33, 34 and 35 (step S2).

A cartridge requiring urgent treatment may be accepted with priority over the cartridges 30 not having proceeded to the next step S3. The cartridges 30 including any cut-in cartridge transported to the first reagent dispensing section 12 undergo the following processes.

The first reagent is dispensed to the respective reaction tubs 33, 34 and 35 of each cartridge 30 transported to the first reagent dispensing section 12 (step S3). The first reagent is dispensed simultaneously by the reagent dispensing unit 50 having the multiple structure described hereinbefore.

Each cartridge 30 having received the first reagent is transported through the first reaction path 13, and after a predetermined reaction period, to the next, second reagent dispensing section 14 (step S4).

In the second reagent dispensing section 14, unreacted components are removed through the B/F separation from the reaction mixture in each of the reaction tubs 33, 34 and 35 of the cartridges 30. Thereafter the second reagent is dispensed to each of the reaction tubs 33, 34 and 35 (step S5).

Each cartridge 30 having received the second reagent is transported through the second reaction path 15, and after a predetermined reaction period, to the next, unreacted component removing section 16 (step S6).

In the unreacted component removing section 16, unreacted components are removed through the B/F separation from the reaction mixture in each of the reaction tubs 33, 34 and 35 of the cartridges 30 (step S7). The B/F separation is repeated twice in the unreacted component removing section 16, and is carried out one more time in the next, luminescent reagent dispensing section 17.

In the luminescent reagent dispensing section 17, unreacted components are removed through the B/F separation from the reaction mixture in each of the reaction tubs 33, 34 and 35 of the cartridges 30. Thereafter the luminescent reagent is dispensed to each of the reaction tubs 33, 34 and 35 (step S8).

The cartridges 30 having received the luminescent reagent are transported to the hydrogen peroxide dispensing section 18 to receive hydrogen peroxide (step S9).

The cartridges 30 having received hydrogen peroxide are placed in a standby for a predetermined period and then subjected to photometry in the photometric section 19 (step S10).

After the photometry, the cartridges 30 are successively transported to the cartridge discharge section 20. The control section 22 outputs results of the photometry obtained from the photometric section 19 to the display device 24 (step S11).

The apparatus in the first embodiment may be adapted to carry out an analytical curve correction as follows.

Figure 18:
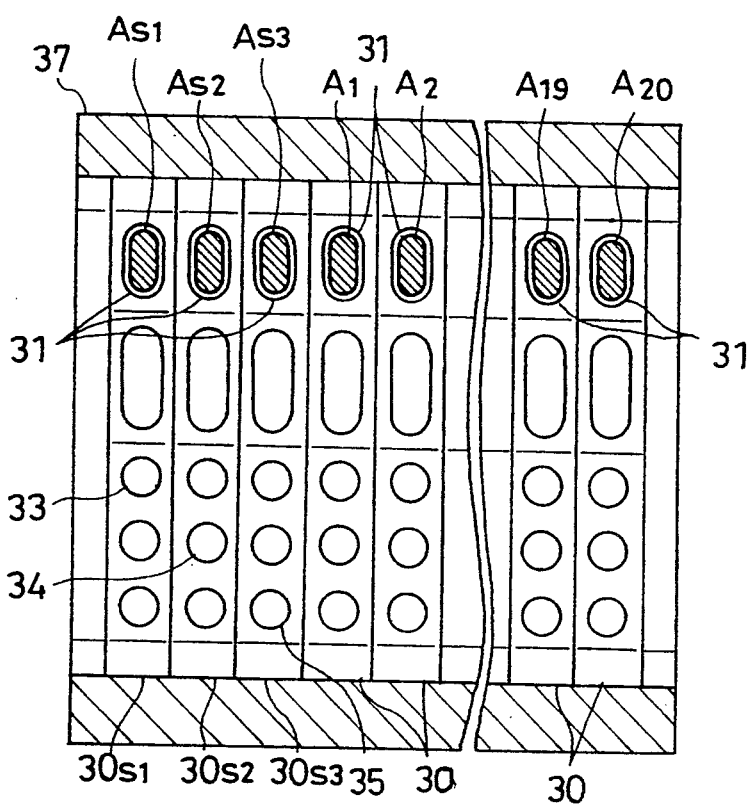
FIG. 18 is a view showing an arrangement of cartridges in the rack for carrying out an analytical curve correction.

For correcting an analytical curve, as shown in FIG. 18, sample specimens AS1–AS3 for analytical curve correction are placed in the first three cartridges (hereinafter called the sample cartridges) 30S1–30S3 of the twenty-three cartridges 30 in the rack 37 to be set to the cartridge standby section 11. Examination is conducted for these sample cartridges 30S1-30S3 prior to the twenty cartridges 30 really intended for the examination (specimens A1-A20 to be examined being placed in the specimen tubs 31 of the respective cartridges 30). Consequently, a new analytical curve obtained from an analytical curve correction following photometry of the sample cartridges 30S1-30S3 is used in the examination of the subsequent specimens.

Next, a construction adjacent the specimen dispensing unit 40 will be described with reference to FIG. 19. As shown in FIG. 19, a predetermined buffer area BA is provided between a dispensing position of the specimen dispensing unit 40 and the urgent cartridge receiver 41. Further, a push-back mechanism 21a is provided for pushing the cartridges 30 from the urgent cartridge receiver 41 back toward the rack 37 to allow the cartridges 30 to have the specimens distributed again by the specimen dispensing unit 40. This push-back mechanism 21a is the same push-back mechanism acting to push back the cartridge requiring an urgent examination as noted hereinbefore.

Figure 20:
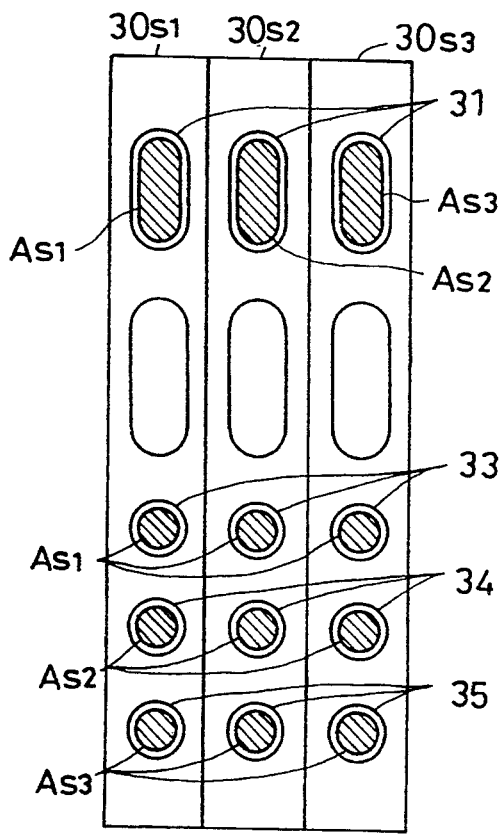
FIG. 20 is a view showing sample specimens placed in reaction tubs of sample cartridges.

With this construction, as shown in FIG. 20, the sample specimen AS1 for examination item KK1 may be dispensed to the reaction tubs 33 of the three sample cartridges 30S1-30S3. Similarly, the sample specimen AS2 for examination item KK2 may be dispensed to the reaction tubs 34, and the sample specimen AS3 for examination item KK3 to the reaction tubs 35. The examination item KK1 is examined with the reaction tubs 33, the examination item KK2 with the reaction tubs 34, and the examination item KK with the reaction tubs 35.

An example of a dispensing sequence will be described with reference to FIGS. 21A through 21I.

Figure 21A:
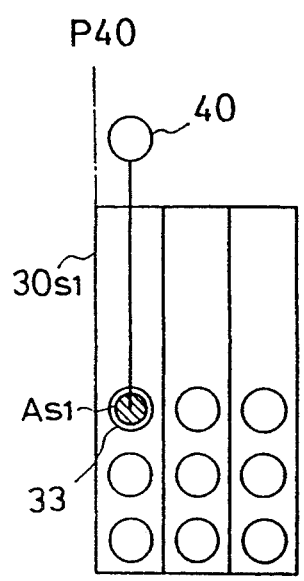
FIGS. 21A through 21I are explanatory views showing a sequence of distributing the sample specimens to the reaction tubs of the sample cartridges.
Figure 21B:
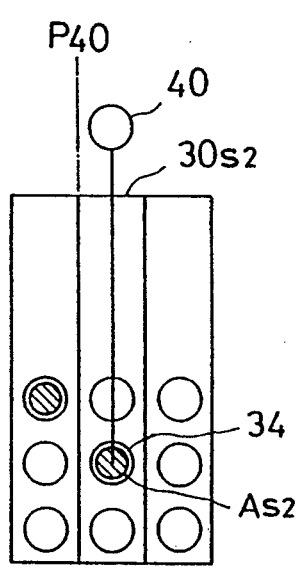
Figure 21C:
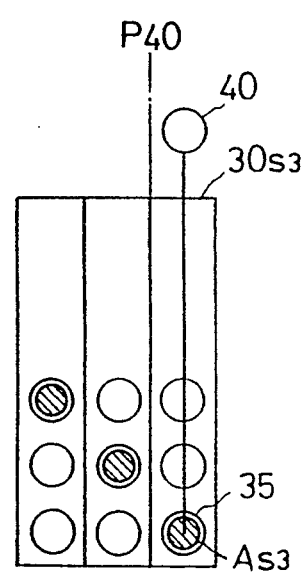
Figure 21D:
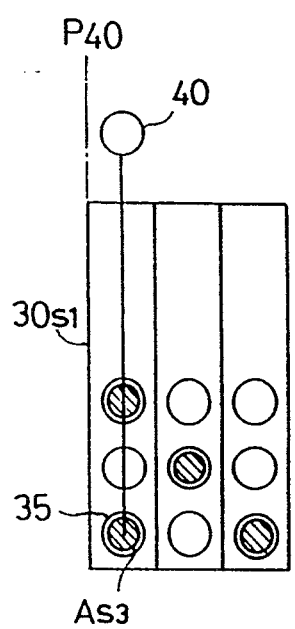
Figure 21E:
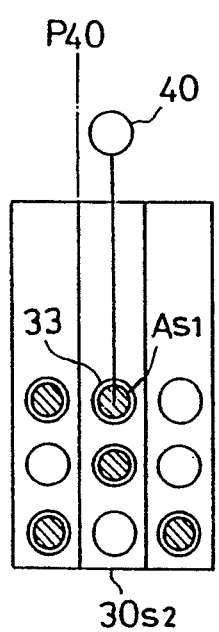
Figure 21F:
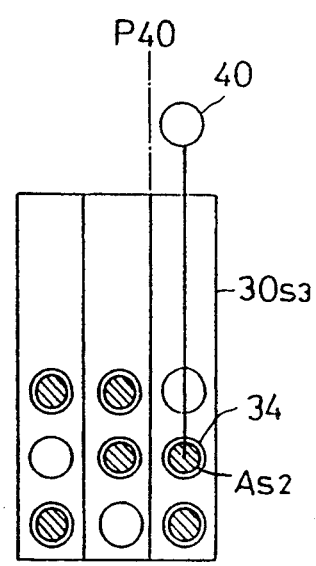
Figure 21G:
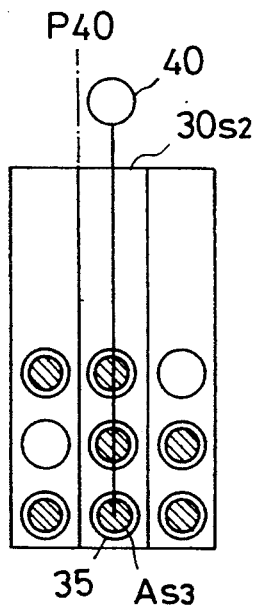
Figure 21H:
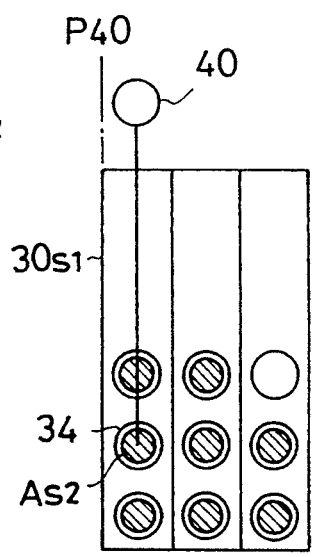
Figure 21I:
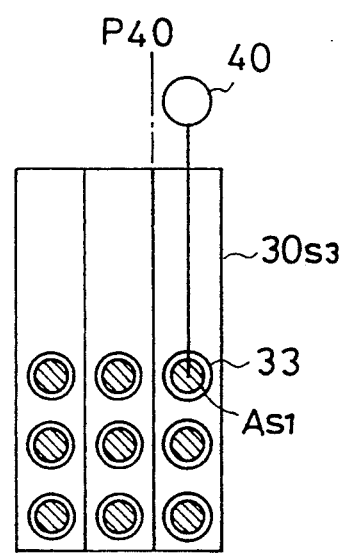

The first sample cartridge 30S1 is transported to a specimen dispensing position P40, and the sample specimen AS1 in this cartridge 30S1 is distributed to the reaction tub 33 thereof (FIG. 21A). Next, the second sample cartridge 30S2 is transported to the position P40, and the sample specimen AS2 in this cartridge 30S2 is distributed to the reaction tub 34 thereof (FIG. 21B). Then, the third sample cartridge 30S3 is transported to the position P40, and the sample specimen AS3 in this cartridge 30S3 is distributed to the reaction tub 35 thereof (FIG. 21C). Further, the sample specimen AS3 is sucked from the third sample cartridge 30S3, and the push-back mechanism 21a is operated to push the first sample cartridge 30S1 back to the position P40. The sample specimen AS3 sucked is dispensed to the reaction tub 35 of the first sample cartridge 30S1 (FIG. 21D). Next, the sample specimen AS1 is sucked from the first sample cartridge 30S1, and the second sample cartridge 30S2 is transported to the position P40. The sample specimen AS1 sucked in is dispensed to the reaction tub 33 of the second sample cartridge 30S2 (FIG. 21E). Similarly, the sample specimen AS2 of the second sample cartridge 30S2 is distributed to the reaction tub 34 of the third sample cartridge 30S3 (FIG. 21F). Subsequently, the sample specimen AS3 of the third sample cartridge 30S3 is distributed to the reaction tub 35 of the second sample cartridge 30S2 (FIG. 21G). The sample specimen AS2 of the second sample cartridge 30S2 is distributed to the reaction tub 34 of the first sample cartridge 30S1 (FIG. 21H). The sample specimen AS1 of the first sample cartridge 30S1 is distributed to the reaction tub 33 of the third sample cartridge 30S3 (FIG. 21I).

Instead of the above sequence, the sample specimen AS1 may be sucked in one stroke from the first sample cartridge 30S1 to be successively distributed to the reaction tub 33 of the first sample cartridge 30S1, the reaction tub 33 of the second sample cartridge 30S2, and the reaction tub 33 of the third sample cartridge 30S3. Similarly, the specimens AS1 and AS2 may be successively distributed to the reaction tubs 34 and 35.

Figure 22:
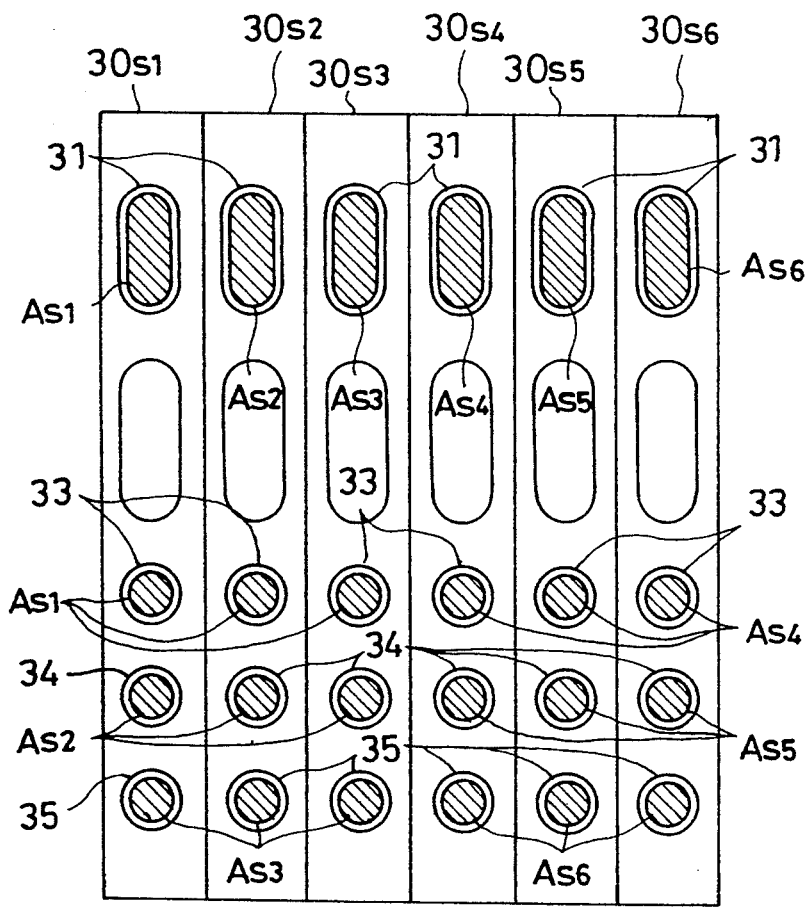
FIG. 22 is a view showing sample specimens placed in reaction tubs of sample cartridges.

By distributing the sample specimens as in FIG. 20, an analytical curve correction may be effected using many (three) sample data and a reduced number of (three) sample cartridges for each examination item. This is achieved since all of the reaction tubs 33, 34 and 35 of the sample cartridge 30S1-30S3 are used. Thus, where each cartridge 30 has four reaction tubs and examination is conducted on four items (with a dispensing unit 50 to allow the four-item examination to be carried out in parallel as described hereinafter), an analytical curve correction may be effected using four sample cartridges and four sample specimens.

Where the third embodiment described hereinafter is used, examination may be conducted on four or more items even if each cartridge 30 has only three reaction tubs. In this case, for example, where examination is conducted on six items (KK1-KK6), as shown in FIG. 22, sample specimen AS1 for examination item KK1 may be placed in the reaction tub 33 of each of the first three sample cartridges 30S1-30S3 of six sample cartridges 30S1-30S6 used. Sample specimens AS2 and AS3 for examination items KK2 and KK3 may be placed in the reaction tubs 34 and 35 of these sample cartridges 30S1-30S3, respectively. Sample specimen AS4 for examination item KK4 may be placed in the reaction tub 33 of each of the fourth to sixth sample cartridges 30S4-30S6. Sample specimens AS5 and AS6 for examination items KK5 and KK6 may be placed in the reaction tubs 34 and 35 of these sample cartridges 30S4-30S6, respectively. Then, an analytical curve correction may be effected for each examination item, using three sample specimens. In this case, however, it is necessary for the buffer area BA (see FIG. 19) between the dispensing position of the specimen dispensing unit 40 and the urgent cartridge receiver 41 to have a length to allow movement of six sample cartridges 30.

For distributing the sample specimens to the reaction tubs 33, 34 and 35 of each sample cartridge as in FIG. 20 or 22, the specimen dispensing unit 40 may be moved between the urgent cartridge receiver 41 and rack 37 instead of pushing back the sample cartridges 30. In this construction, the sample specimens may be distributed to the respective reaction tubs 33, 34 and 35 in a sequence as shown in FIGS. 21A through 21I, by moving the specimen dispensing unit 40 with the sample cartridges fixed in juxtaposition.

The sample cartridges having received the sample specimens as in FIG. 20 or 22 undergo the examination processes from the first reagent dispensing section 12 to the photometric section 19 before the cartridges 30 having the objective specimens as described hereinbefore.

Figure 2:
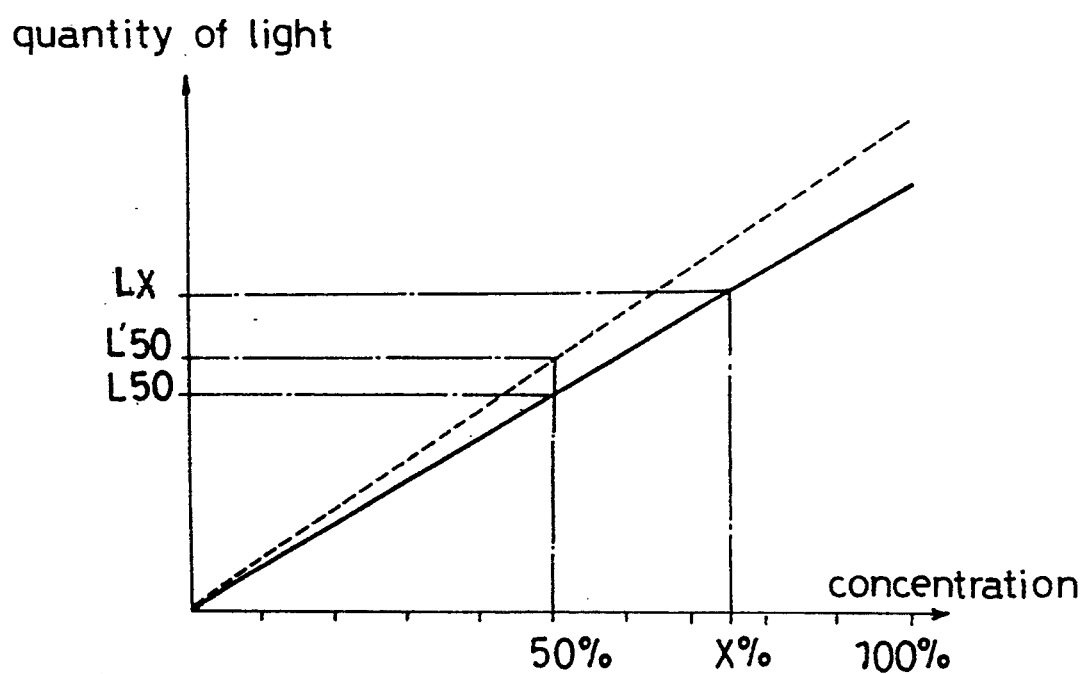
FIG. 2 is an explanatory view showing a sequence of collecting an analytical curve.

An analytical curve correction is carried out by the control section 22 based on results of photometry. At this time, three measurement results (referenced L′50S1, L′50S2 and L50S3) are obtained from sample specimen AS1 (of, say, 50% concentration), for example. An average of these measurement results is calculated (referenced L′50 which is a sum of L′50S1, L′50S2 and L50S3 divided by 3). This average is used to multiply a known analytical curve by L′50/L50 to obtain a new analytical curve as described in relation to the prior art (FIG. 2), in which "L50" represents light emission of the known analytical curve for the concentration of 50%. A similar analytical curve correction is made for each of the sample specimens AS2 and AS3.

Figure 1:
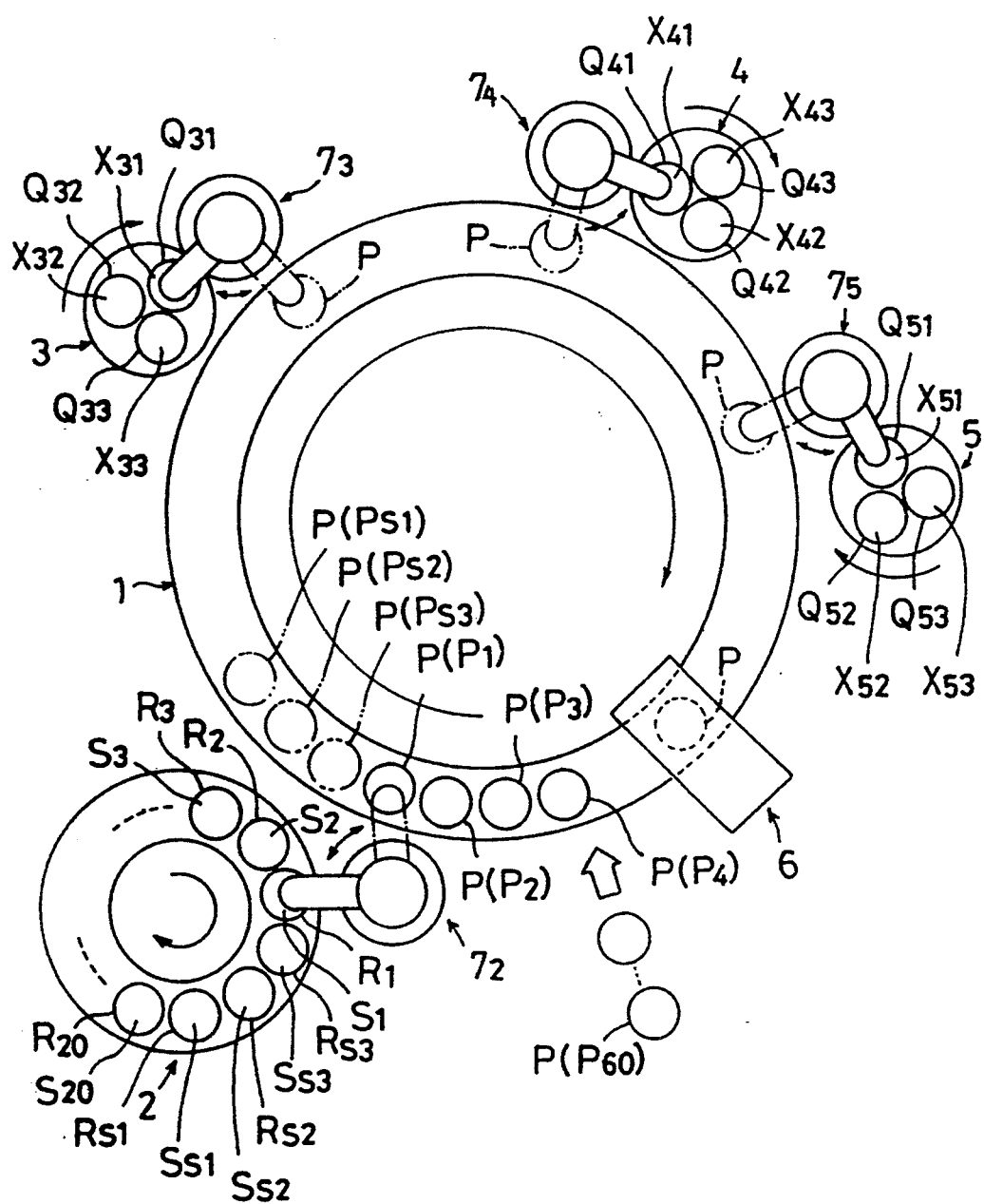
FIG. 1 is a view schematically showing a construction of a conventional automatic analyzing apparatus.

With the sample specimens AS1-AS3 distributed as in FIG. 20 and an analytical curve correction effected as described above, the analytical curve correction for each examination item may be carried out using three sample specimens. This assures an accurate analytical curve correction. Moreover, in this embodiment, the examination processes for the three reaction tubs are carried out simultaneously, and therefore three cartridges 30 are used. By contrast, in the conventional apparatus which transports one reaction vessel after another (see FIG. 1), nine reaction vessels must be transported successively to effect an analytical curve correction with the same degree of accuracy as the above analytical curve correction. This embodiment can carry out an analytical curve correction in about one third of the time taken with the conventional apparatus.

SECOND EMBODIMENT

The apparatus in the first embodiment transports cartridges 30 only two-dimensionally in the X and Y directions. The present invention is not limited to such a transport mode but includes an apparatus for transporting cartridges 30 in X, Y and Z directions. The apparatus for transporting cartridges 30 in the X, Y and Z directions will be described hereinafter as a second embodiment.

As noted above, the apparatus in the second embodiment is constructed to transport cartridges 30 three-dimensionally in the X, Y and Z directions. Its specific construction will be described with reference to FIGS. 23 and 24.

Figure 23:
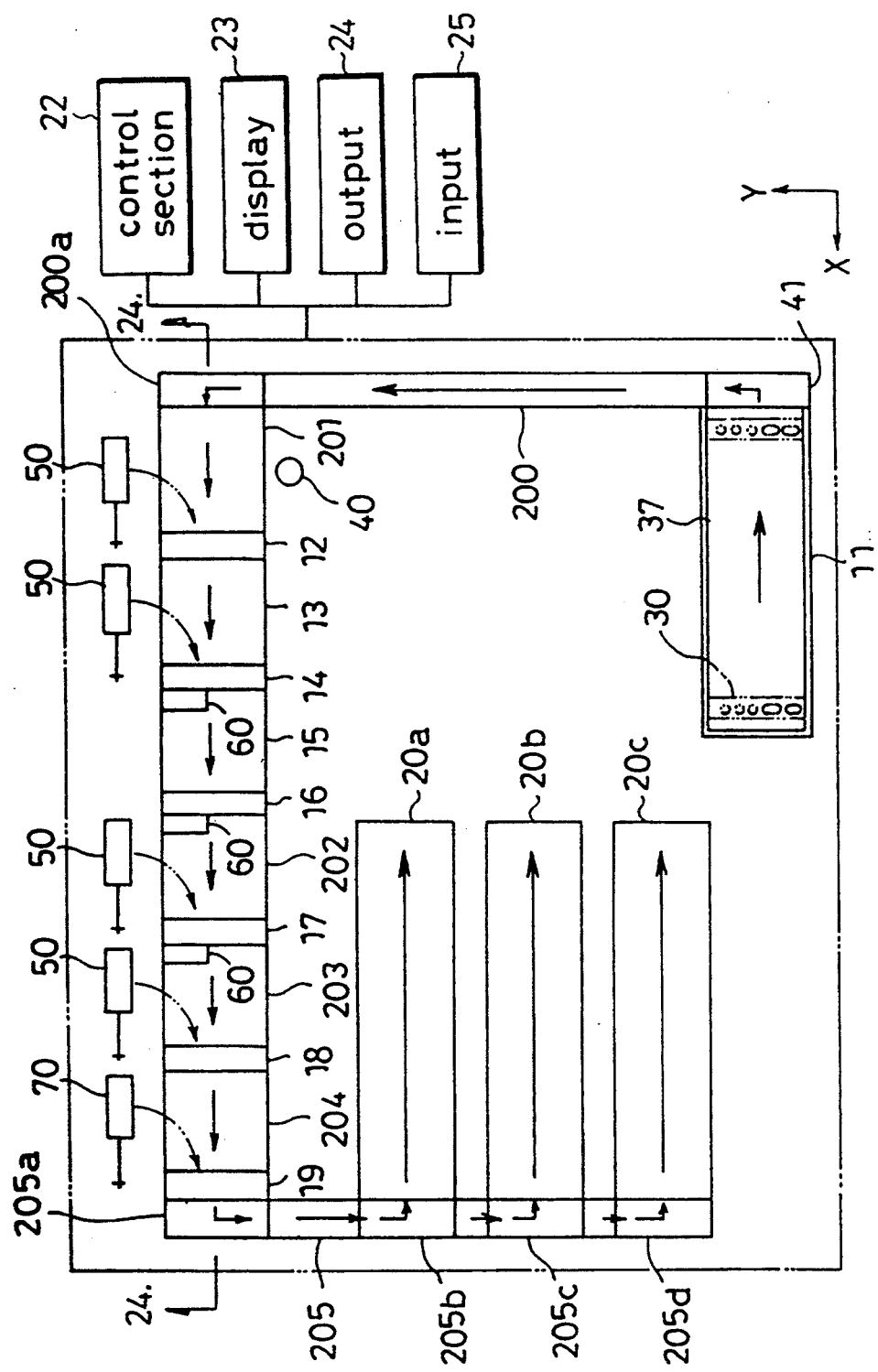
FIG. 23 is an overall plan view of an automatic analyzing apparatus in a second embodiment of the invention.
Figure 24:
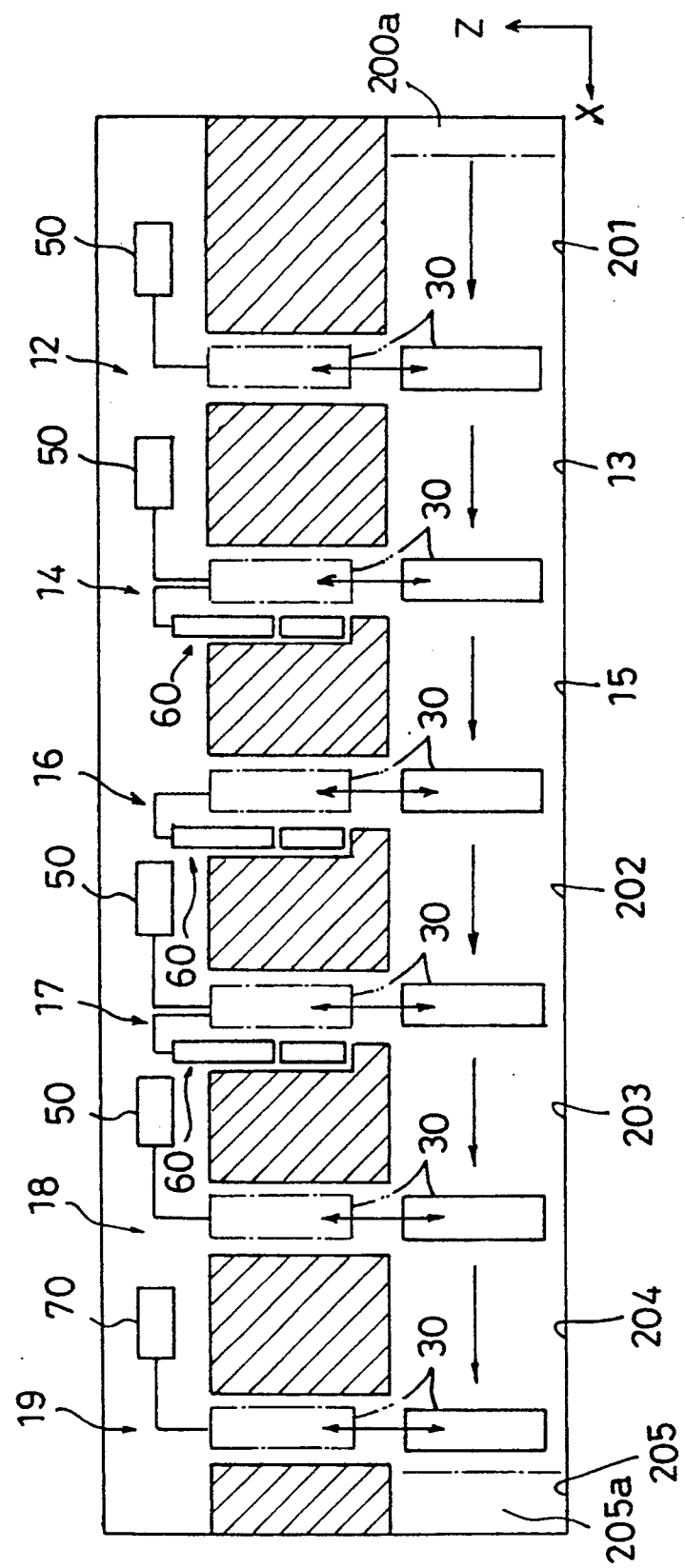
FIG. 24 is a section taken on line 24—24 of FIG. 23.

FIG. 23 is an overall plan view of the apparatus in the second embodiment. FIG. 24 is a section taken on line 24—24 of FIG. 23. In the drawings, like reference numerals are used to identify like parts in the first embodiment which will not be described again.

Cartridges 30 are successively pushed out of the rack 37 mounted in a cartridge standby section 11 to an urgent cartridge receiver 41 (in the X direction). Then the cartridges 30 are transported in the Y direction along a transport line 200 as indicated by an arrow, and to a specimen dispensing unit 40 (in the X direction).

Figure 25:
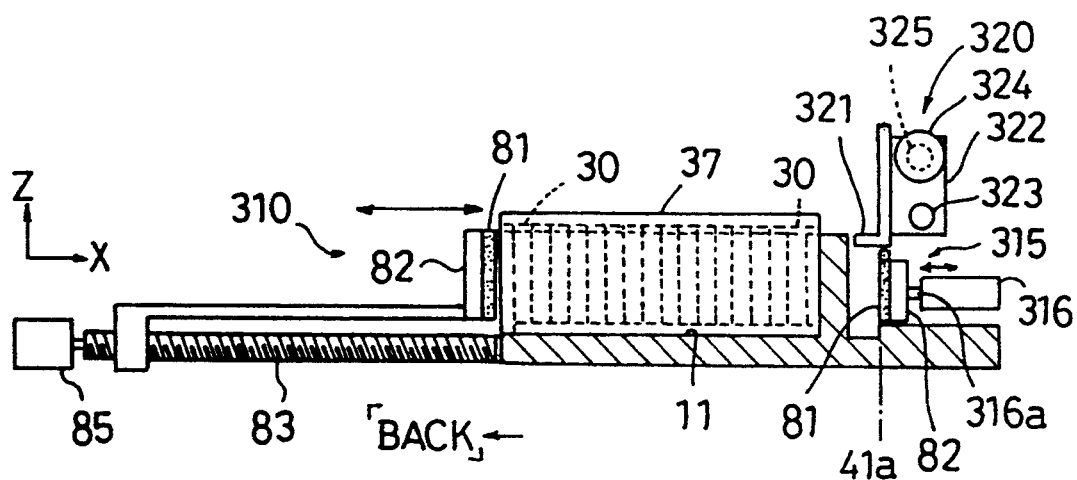
FIG. 25 is a side view showing operation of transport mechanisms in a cartridge standby section and a transport line.
Figure 26:
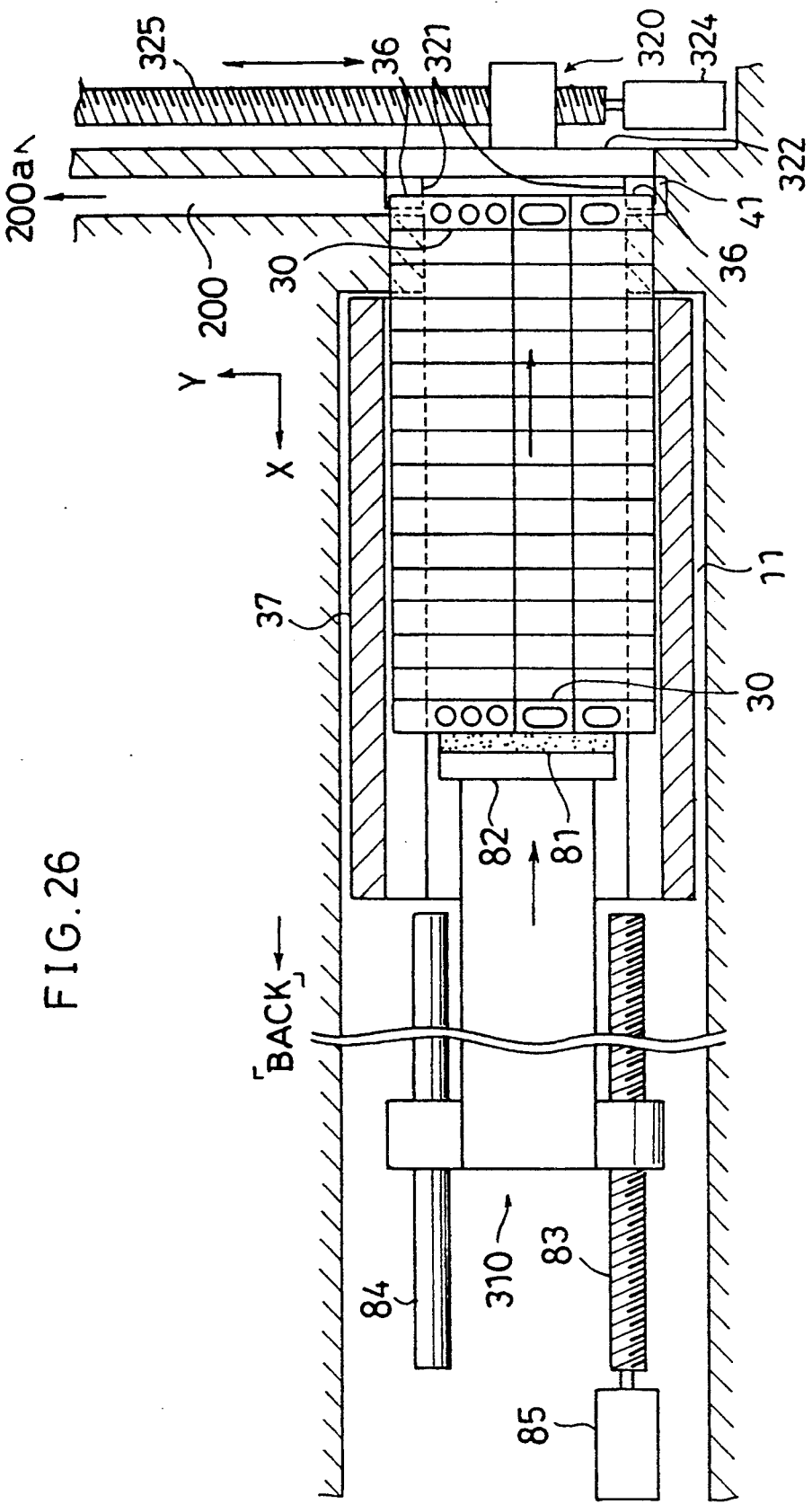
FIG. 26 is a plan view showing the operation of the transport mechanisms in the cartridge standby section and the transport line.

Specifically, as shown in FIGS. 25 and 26, a transport mechanism 310 having a construction similar to the transport mechanism 21 described with reference to FIGS. 12 and 13 has a pusher 82 standing by in a rearward "BACK" position. When the rack 37 is set to the cartridge standby section 11 and a command is given to start an examination, the transport mechanism 310 pushes the cartridges 30 all together toward the urgent cartridge receiver 41, with the pusher 82 pressing on the cartridge 30 adjacent a "BACK" end of the rack 37 toward the urgent cartridge receiver 41 (in the X direction).

At this time, the urgent cartridge receiver 41 has flange supports 321 of a transport mechanism 320 standing by for transporting the cartridges 30 along the transport line 200. When the flanges 36 of the first cartridge 30 pushed out of the rack 37 mount on the flange supports 321, the transport mechanism 310 in the cartridge standby section 11 stops pushing and stands by again.

The cartridge 30 with the flanges 36 mounted on the flange supports 321 of the transport mechanism 320 is transported to a terminal end 200a of the transport line 200. As shown in FIGS. 25 and 26, the transport mechanism 320 has the flange supports 321 interconnected at ends thereof through a connecting portion 322. The connecting portion 322 is meshed with a screw shaft 325 extending parallel to the transport line 200 and connected to a motor 324. Further, the connecting portion 322 is fitted on a guide rod 323 extending parallel to the screw shaft 325. Thus, with opposite rotations of the motor 324, the flange supports 321 are movable between the urgent cartridge receiver 41 and the terminal end 200a of the transport line 200 (see FIG. 23). The flange supports 321 have a sensor such as a limit switch, not shown, attached thereto for detecting the flanges 36 of the cartridges 30 mounted on the flange supports 321. The sensor is used to determine timing for causing the transport mechanism 310 to stop pushing the cartridges 30 and stand by as noted above.

Figure 27:
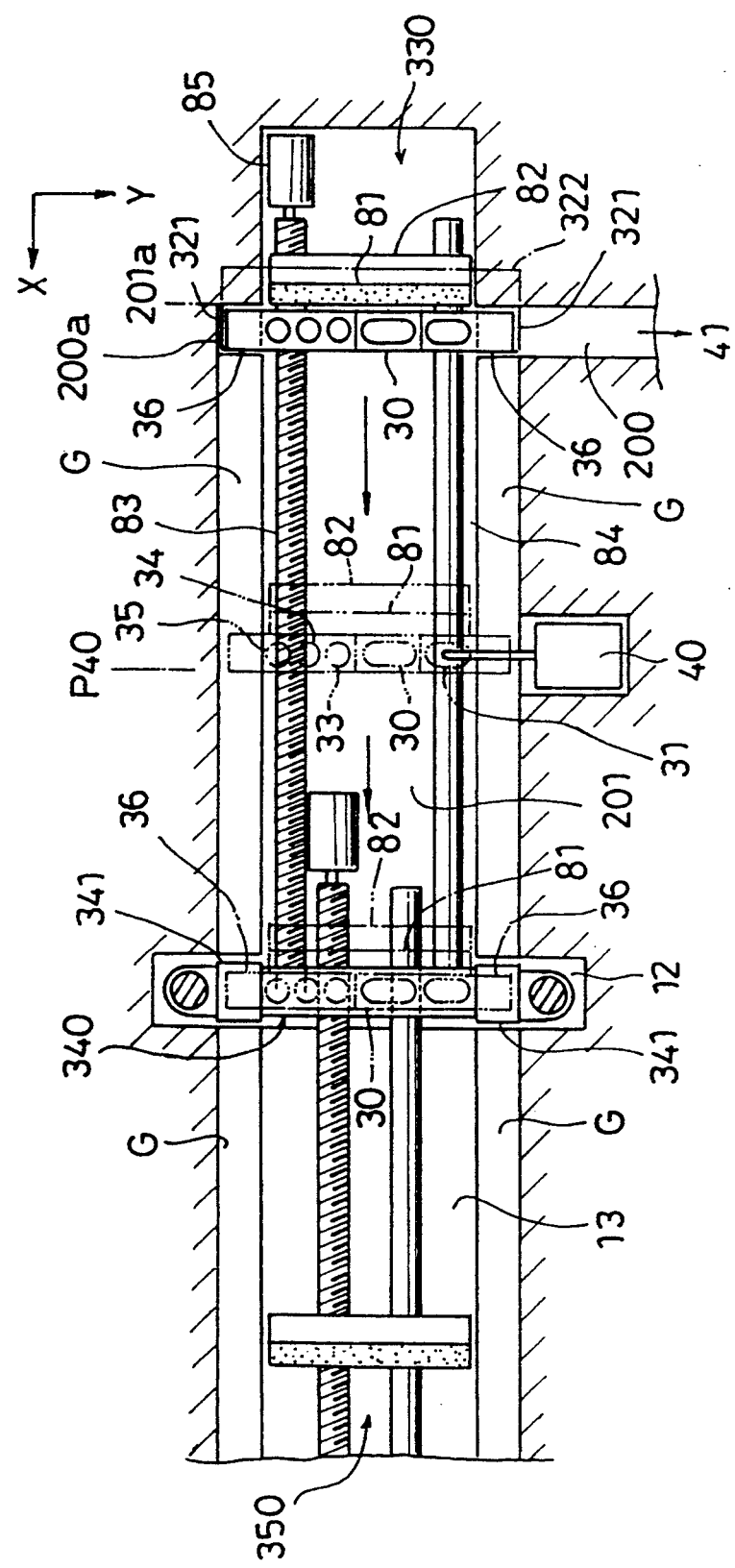
FIG. 27 is a plan view showing the operation of a transport mechanism in a transport line including a specimen dispensing unit and a transport mechanism in a first reagent dispensing section.

When the cartridge 30 is transported to the terminal end 200a of the transport line 200, a transport mechanism 330 in a transport line 201 (having a construction similar to the transport mechanism 21 described with reference to FIGS. 12 and 13) has a pusher 82 standing by in a standby position 201a as shown in FIG. 27. The transport mechanism 330 pushes out the cartridge 30 transported to the terminal end 200a of the transport line 200, to transfer the flanges 36 of the cartridge 30 from the flange supports 321 of the transport mechanism 320 to guides G provided in the transport line 201. Further, the transport mechanism 330 pushes the cartridge 30 a predetermined amount to a position opposed to a specimen dispensing unit 40 (i.e. a specimen dispensing position P40 of the specimen dispensing unit 40). The transport mechanism 330 stands by in this state. The specimen dispensing unit 40 distributes a specimen from the specimen tub 31 to the reaction tubs 33, 34 and 35 as necessary. After the specimen distribution, the transport mechanism 330 pushes the cartridge 30 again to pass the cartridge 30 on to a transport mechanism 340 described hereinafter. Thereafter the pusher 82 returns to the standby position 201a.

Figure 28:
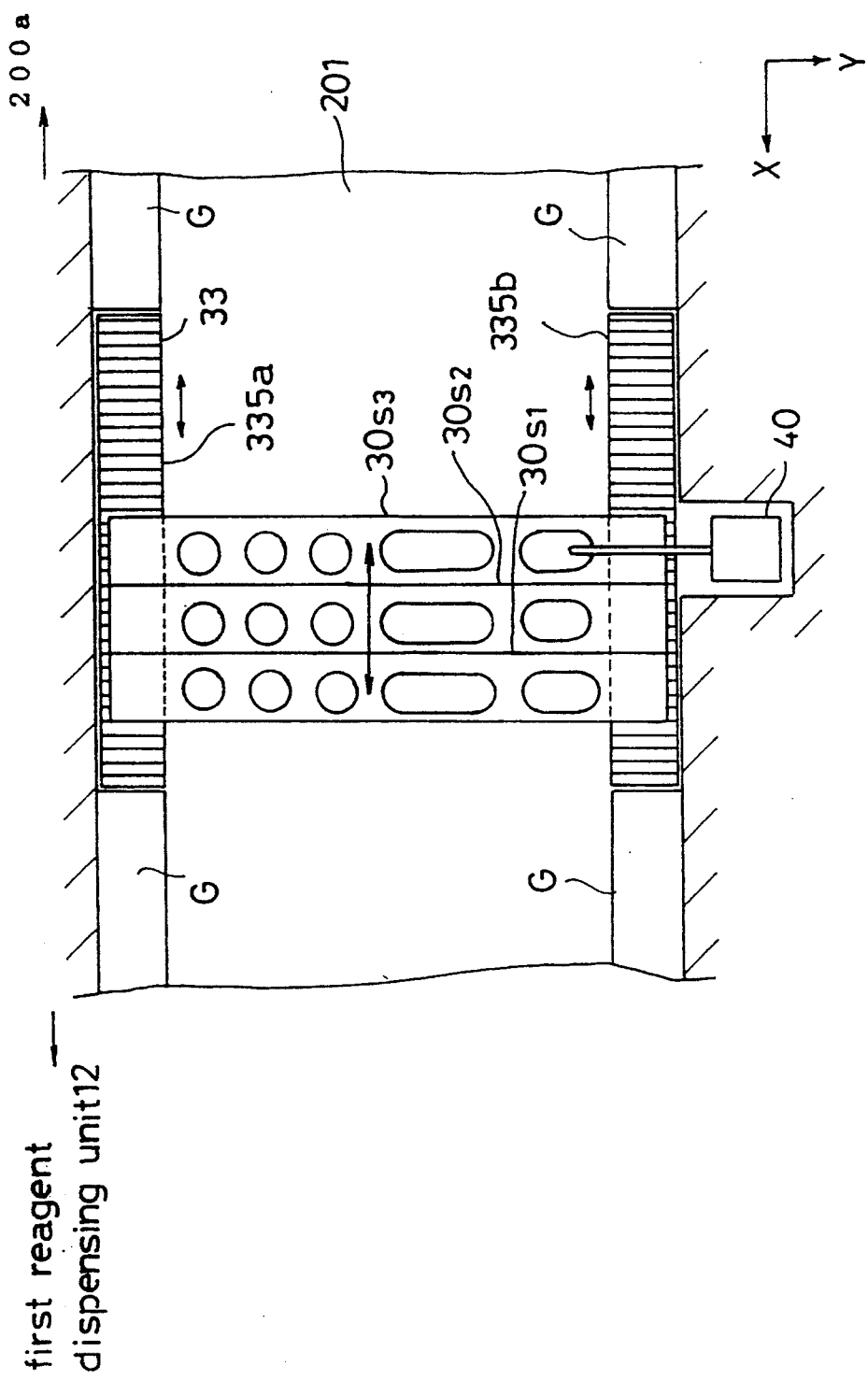
FIG. 28 is a view showing a construction adjacent the specimen dispensing unit in the second embodiment where an analytical curve correction is effected by efficiently using sample cartridges.

On the other hand, when the cartridge 30 has been transferred from the flange supports 321 of the transport mechanism 320 to the guides G of the transport line 201, the transport mechanism 320 returns the flange supports 321 to the urgent cartridge receiver 41. When the flange supports 321 of the transport mechanism 320 return to the urgent cartridge receiver 41, the transport mechanism 310 pushes out the cartridges 30 again. Consequently, a next cartridge 30 is set to the flange supports 321 of the transport mechanism 320. The transport mechanism 320 transports this cartridge 30 to the terminal end 200a of the transport line 200 as above. In transporting the second and subsequent cartridges 30, if the pusher 82 of the transport mechanism 330 has not returned to the standby position 201a, the transport mechanism 320 stands by in the urgent cartridge receiver 41, in a condition ready to transport the cartridge 30. When the pusher 82 of the transport mechanism 330 has returned to the standby position 201a, the transport mechanism 320 begins transporting the cartridge 30 to the terminal end 200a of the transport line 200.

Where the apparatus in the second embodiment is adapted to carry out an analytical curve correction as described in the first embodiment, the guides G may include belt conveyors 335a and 335b opposed to the specimen dispensing unit 40 as shown in FIG. 28. These belt conveyors 335a and 335b are synchronously driven by a motor not shown. With this construction, the cartridge 30 transported by the transport mechanism 330 to the belt conveyors 335a and 335b may be transported toward a first reagent dispensing section 12, or may be returned toward the terminal end 200a of the transport line 200. Alternatively, the specimen dispensing unit 40 may be adapted movable as described in the first embodiment.

In this case, sample cartridges (e.g. three cartridges) 30S1–30S3 for use in the analytical curve correction are transported differently from the cartridges 30 for an ordinary examination. The belt conveyors 335a and 335b are driven after all of the sample cartridges 30S1–30S3 are transported thereto. Then, sample specimens AS1–AS3 are distributed to predetermined reaction tubs 33, 34 and 35 of the sample cartridges 30S1–30S3.

When the operator gives an instruction to accept a cartridge for an urgent examination, the transport mechanisms 310 and 320 operate as follows.

When the flanges 36 of a cartridge 30 pushed out of the rack 37 have been set to the flange supports 321 of the transport mechanism 320 in the urgent cartridge receiver 41, the transport mechanism 310 draws the pusher 82 in the "BACK" direction of the rack 37 by an amount corresponding to one cartridge 30. As shown in FIG. 25, the pusher 82 of a push-back mechanism 315 standing by in a standby position 41a opposed to the rack 37 across the urgent cartridge receiver 41 is operated to push the cartridge 30 from the urgent cartridge receiver 41 back toward the rack 37. This push-back mechanism 315 includes an air cylinder 316 having a rod 316a extendible and contractible to cause the pusher 82 with silicone rubber 81 bonded thereto to push the cartridge 30 back to the rack 37 and to return to the standby position 41a. The operator places a cartridge 30 for use in the urgent examination into the urgent cartridge receiver 41 from above, setting the flanges thereof to the flange supports 321 of the transport mechanism 320 standing by and ready to accept a cartridge 30 in the urgent cartridge receiver 41. Then the operator gives an indication through the input device 25 that the cartridge for use in the urgent examination has been placed in position. With this indication, the transport mechanism 320 transports this cartridge 30 to the terminal end of the transport line 200 after waiting for the pusher 82 of the transport mechanism 330 to return to the standby position 201a. Upon completion of transport of the cartridge 30 for the urgent examination, an ordinary operation is resumed to transport the cartridges 30 having been pushed back to the rack 37 to the terminal end 200a of the transport line 200.

The situation can be different from the above. For example, the transport mechanism 320 may be transporting a cartridge 30 halfway through the transport line 201, or a cartridge 30 may be standing by at the forward end of the rack 37, waiting for the flange supports 321 of the transport mechanism 320 to return to the urgent cartridge receiver 41. In such a case, the transport mechanism 310 does not push the cartridge 30 out of the rack 37 even after the flange supports 321 return to the urgent cartridge receiver 41, but waits for the operator to place a cartridge for an urgent examination in position. After the cartridge for an urgent examination cuts in, the transport mechanism 310 pushes the cartridge 30 out of the rack 37.

The above transport mechanisms 310, 320 and 330 all correspond to the transport mechanism of the present invention. The operations of the transport mechanisms 310, 320 and 330 and push-back mechanism 315 (and belt conveyors 335) are controlled by the control section 22. Transport mechanisms 340, 350, 360 and 370 provided for the respective examination processes as described later also correspond to the transport mechanism of the present invention. The operations of these transport mechanisms 340, 350, 360 and 370 also are controlled by the control section 22. The CPU of the control section 22 may be the multitasking type to operate these transport mechanisms simultaneously. In this case, the respective tasks are programmed to operate the transport mechanism 310 and the like.

Next, the cartridge 30 having the specimen distributed by the specimen dispensing unit 40 is pushed out by the transport mechanism 330 toward the first reagent dispensing section 12 as noted hereinbefore. The cartridge 30 is transported in the Z direction to the first reagent dispensing section 12. After receiving the first reagent in the first reagent dispensing section 12, the cartridge 30 is transported in the X direction along a first reaction path 13.

Figure 29:
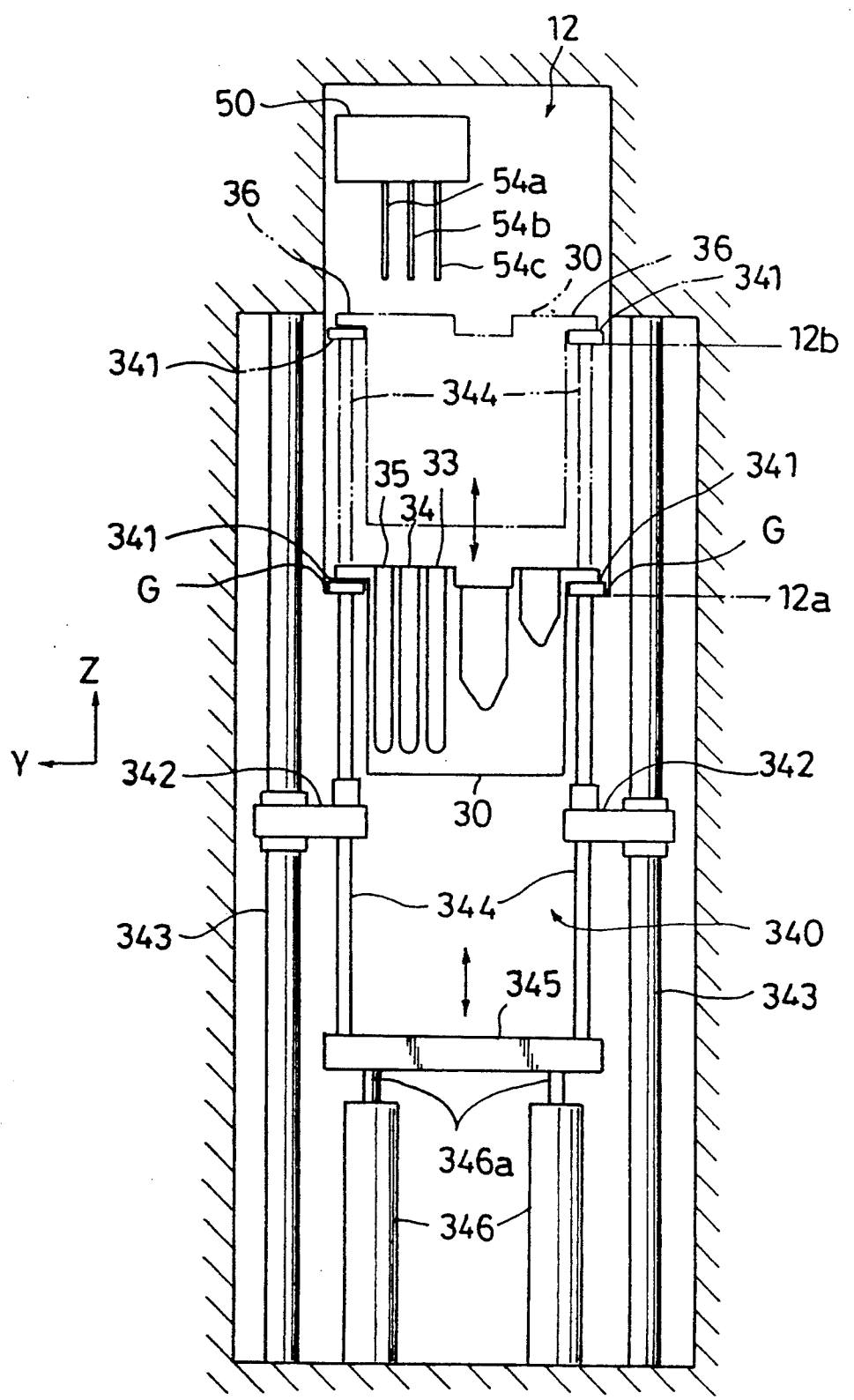
FIG. 29 is a front view showing a construction and operation of the transport mechanism in the first reagent dispensing section.

Specifically, as shown in FIG. 27, the transport mechanism 330 transports the cartridge 30 and passes it on to flange supports 341 of the transport mechanism 340 standing by in a standby position 12a of the first reagent dispensing section 12 (see FIG. 29). The flange supports 341 of the transport mechanism 340 are flush with the guides G of the transport line 201. Thus, the flanges 36 of the cartridge 30 pushed by the transport mechanism 330 are transferred from the guides G of the transport line 201 to the flange supports 341 of the transport mechanism 340. When the cartridge 30 is mounted on the flange supports 341 of the transport mechanism 340, the transport mechanism 330 completes its cartridge transporting operation and the pusher 82 is retracted to the standby position 201a.

The cartridge 30 having the flanges 36 supported by the flange supports 341 of the transport mechanism 340 is raised in the Z direction by the transport mechanism 340 to reach a dispensing position 12b of the first reagent dispensing section 12 (see FIG. 29). As shown in FIG. 29, the transport mechanism 340 has the flange supports 341 connected to distal ends of shafts 344 supported through guides 342 by guide rods 343 to be free from chattering during transport. The shafts 344 have proximal ends thereof connected to a stay 345 which is in turn connected to distal ends of rods 346a of air cylinders 346. The rods 346a of the air cylinders 346 are extendible and contractible to transport the cartridge 30 in the Z direction as supported by the flange supports 341. The drive mechanism for moving the cartridge 30 vertically in the Z direction may comprise a motor-driven pinion engaged with a rack extending in the Z direction, instead of using the air cylinders 346. Thus, the transport mechanism 340 may have a drive mechanism including a motor, rack and pinion.

Figure 30:
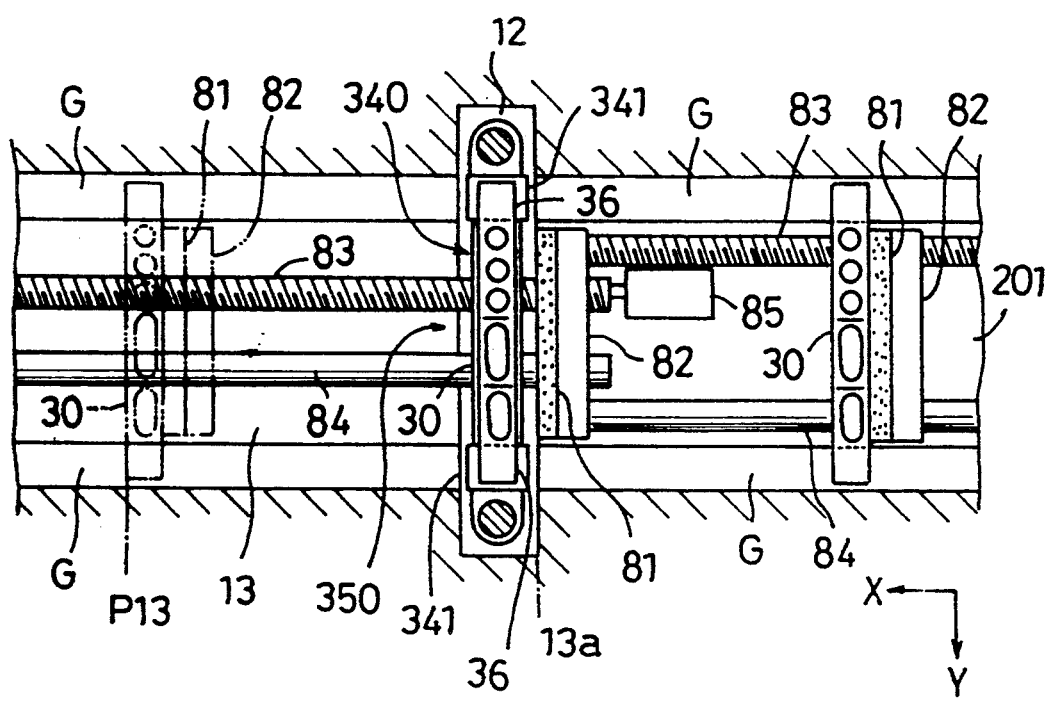
FIG. 30 is a plan view showing operations of the transport mechanisms in the first reagent dispensing section and first reaction path.

The first reagent dispensing section 12 includes a reagent dispensing unit 50 for dispensing a predetermined first reagent to the reaction tubs 33, 34 and 35 of the cartridge 30 transported thereto. After dispensation of the first reagent, the transport mechanism 340 lowers the cartridge 30 in the Z direction to the standby position 12a. On the other hand, as shown in FIG. 30, the transport mechanism 350 (having a construction similar to the transport mechanism 21 shown in FIGS. 12 and 13) in the first reaction path 13 returns a pusher 82 thereof to a standby position 13a of the first reaction path 13 and maintains it standing by therein after the transport mechanism 340 transports the cartridge 30 to the dispensing position 12b and the first reagent is dispensed thereto and before the cartridge 30 is returned to the standby position 12a. The pusher 82 moves to the standby position 13a of the first reaction path 13, passing through a space between the bottom of the cartridge 30 raised in the Z direction by the transport mechanism 340 and the top of the stay 345.

The pusher 82 of the transport mechanism 350 standing by in the standby position 13a of the first reaction path 13 pushes the cartridge 30 returned to the standby position 12a by the transport mechanism 340 after the first reagent is dispensed thereto. The flanges 36 of the cartridge 30 are transferred from the flange supports 341 of the transport mechanism 340 to guides G provided in the first reaction path 13. The transport mechanism 350 transports the cartridge 30 to a predetermined position P13 in the first reaction path 13 and stands by in this state. That is, the transport mechanism 350 stands by in the predetermined position P13 to which it has transported the cartridge 30, before returning the pusher 82 to the standby position 13a for transporting the next cartridge 30 to the first reaction path 13 after the first reagent is dispensed to the next cartridge 30 in the first reagent dispensing section 12. The transport mechanism 350 in the first reaction path 13 includes a screw shaft 83 and a guide rod 84 extending past the first reagent dispensing section 12 into part of the transport line 201. Thus, the pusher 82 of the transport mechanism 350 is movable to the standby position 13a located adjacent the transport line 201 (see FIG. 30).

As shown in FIG. 30, the cartridge 30 (i.e. the cartridge having the specimen distributed by the specimen dispensing unit 40) transported by the transport mechanism 330, following the cartridge 30 transported to the first reaction path 13, stands by in the position opposed to the specimen dispensing unit 40, waiting for the preceding cartridge 30 to proceed to the first reaction path 13. That is, the transport mechanism 340 is unloaded, and the flange supports 341 thereof stand by in the standby position 12a. The transport mechanism 350 pushes the preceding cartridge 30 out to the first reaction path 13, with the pusher 82 of the transport mechanism 350 moving out of the standby position 13a. Then, the transport mechanism 330 transfers the succeeding cartridge 30 to the transport mechanism 340.

The cartridge 30 transported to the first reaction path 13 waits in the first reaction path 13 until the elapse of a predetermined reaction period for the first reagent dispensed thereto. After the predetermined reaction period, the cartridge 30 is pushed toward a second reagent dispensing section 14. Then, the cartridge 30 is transported in the Z direction to the second reagent dispensing section 14. After receiving a second reagent in the second reagent dispensing section 14, the cartridge 30 is transported in the X direction to a second reaction path 15.

Figure 31A:
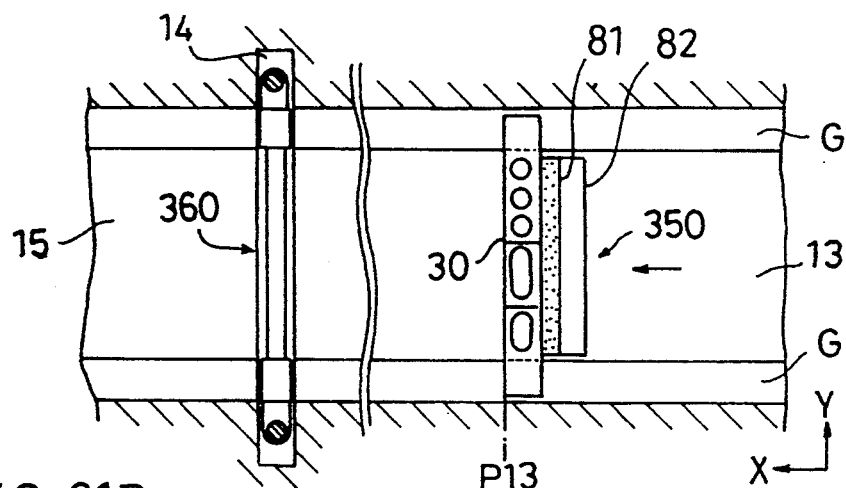
FIGS. 31A, 31B and 31C are views for explaining the elapse of a reaction period in the first reaction path.
Figure 31B:
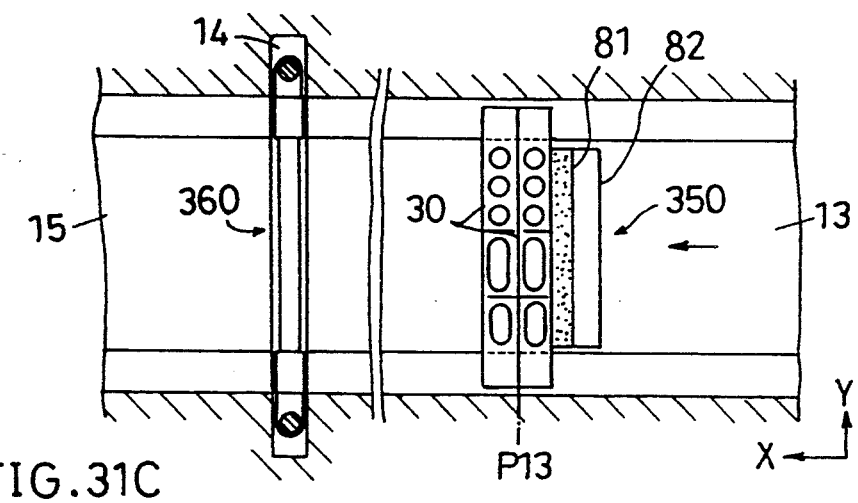
Figure 31C:
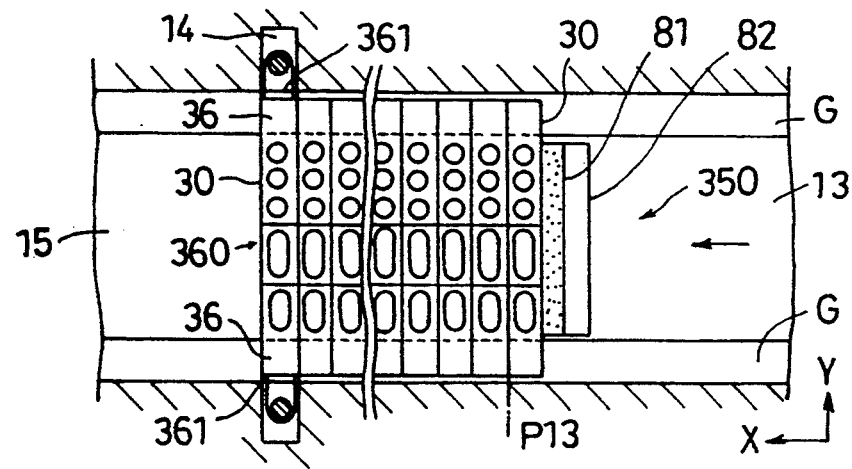

Specifically, as shown in FIG. 31A, the first cartridge 30 transported to the first reaction path 13 is caused to stand by in the position P13. As shown in FIG. 31B, the next cartridge 30 transported to the first reaction path 13 is advanced also to the position P13. The first cartridge 30 is pushed by the next cartridge 30 toward the second reagent dispensing section 14 by an amount corresponding to one cartridge. Subsequently, as shown in FIG. 31C, cartridges 30 transported to the first reaction path 13 push the cartridges 30 standing by in the first reaction path 13 successively toward the second reagent dispensing section 14. Thus, the first cartridge 30 reaches the second reagent dispensing section 14 (at which time, the transport mechanism 370 of the second reaction path 15 stands by in the second reaction path 15). Then, the flanges of this cartridge 30 are transferred from the guides G of the first reaction path 13 to flange supports 361 of the transport mechanism 360 (having a similar construction to the above transport mechanism 340) standing by in a standby position of the second reagent dispensing section 14. The cartridge 30 is raised in the Z direction by the transport mechanism 360 to a dispensing position of the second reagent dispensing section 14.

Figure 32A:
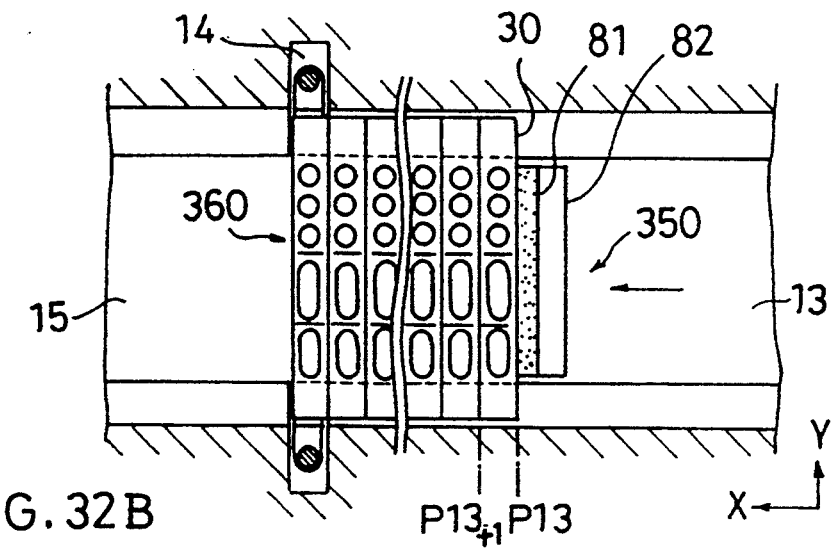
FIGS. 32A, 32B and 32C are views for explaining an operation to adjust a reaction period for the last cartridge transported to the first reaction path.
Figure 32B:
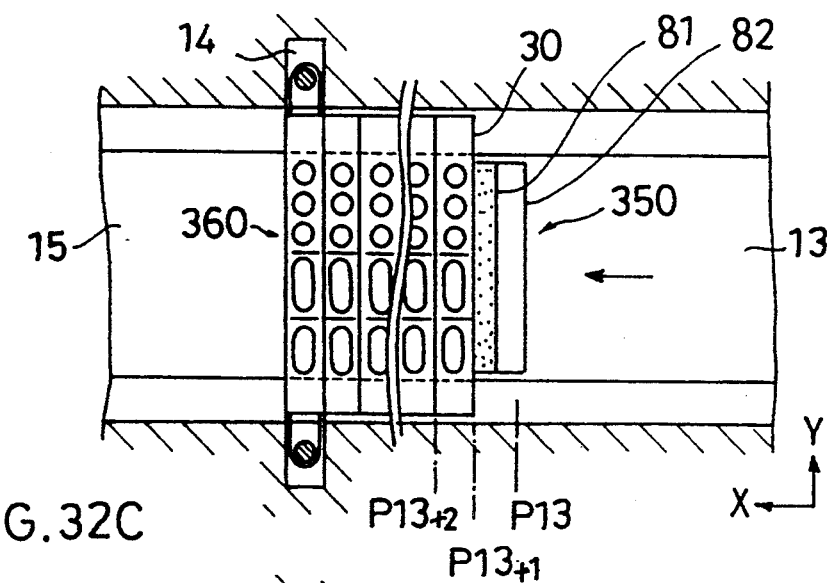
Figure 32C:
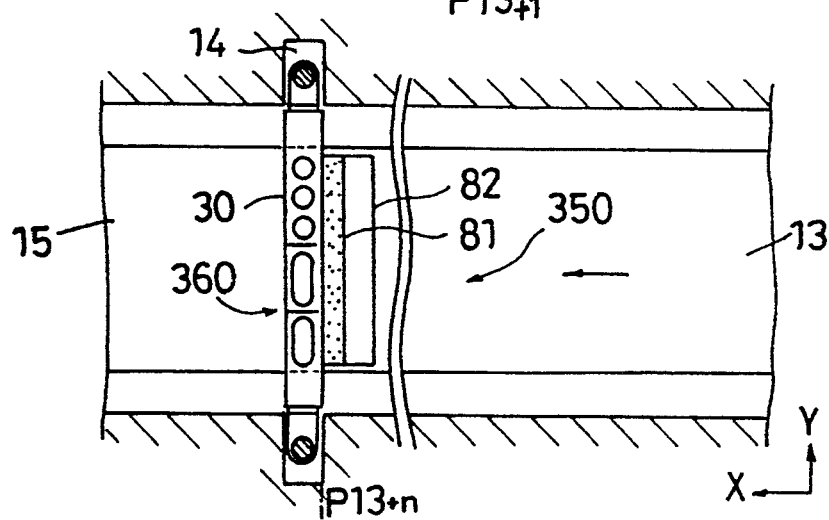

The predetermined position P13 is selected so that the first reagent has a reaction period from the time the first reagent is dispensed in the first reagent dispensing section 12 to the time the cartridge 30 is transported to the predetermined position P13 in the first reaction path 13 and to the dispensing position in the second reagent dispensing section 14 to have unreacted components removed. Consequently, by adjusting the position P13, the apparatus in this embodiment may be adapted for use in different examinations requiring varied reaction periods. This adjustment may be made also where only the reaction period of the first reagent (the waiting time in the first reaction path 13) is varied, without affecting a period of transport along the reaction path to allow reaction of other reagents (e.g. the second reagent). Thus, this apparatus has excellent versatility. The last cartridge 30 has no cartridge pushing it from behind. After the last cartridge 30 is transported to the position P13, as shown in FIGS. 32A through 32C, the transport mechanism 350 pushes the cartridges 30, with timing to transport cartridges 30 to the position P13, through position P13+1, position P13+2 and position P13+n to the second reagent dispensing section 14, taking the reaction period for the last cartridge 30 into account.

The second reagent dispensing section 14 includes an unreacted component removing unit 60 for removing unreacted components, and a reagent dispensing unit 50 for dispensing a predetermined second reagent after removal of the unreacted components. After dispensation of the second reagent, the transport mechanism 360 lowers the cartridge 30 in the Z direction to the standby position of the second reagent dispensing section 14. On the other hand, the transport mechanism 370 (having a construction similar to the transport mechanism 21 shown in FIGS. 12 and 13) in the second reaction path 15 returns to and stands by in a standby position 15a after the transport mechanism 360 transports the cartridge 30 to the dispensing position and the second reagent is dispensed thereto and before the cartridge 30 is returned to the standby position 14a (see FIG. 33A).

The pusher 82 of the transport mechanism 370 standing by in the standby position 15a of the second reaction path 15 pushes the cartridge 30 returned to the standby position by the transport mechanism 360 after the second reagent is dispensed thereto. The flanges 36 of the cartridge 30 are transferred from the flange supports 361 of the transport mechanism 360 to guides G provided in the second reaction path 15. The transport mechanism 370 transports the cartridge 30 to a predetermined position in the second reaction path 15 (i.e. the position similar to the above-mentioned position P13 and corresponding to a reaction period of the second reagent) and stands by in this state. That is, the transport mechanism 370 stands by in the predetermined position in the second reaction path 15 to which it has transported the cartridge 30, before returning the pusher 82 to the standby position 15a for transporting the next cartridge 30 to the second reaction path 15 after the second reagent is dispensed to the next cartridge 30 in the second reagent dispensing section 14.

Figure 33A:
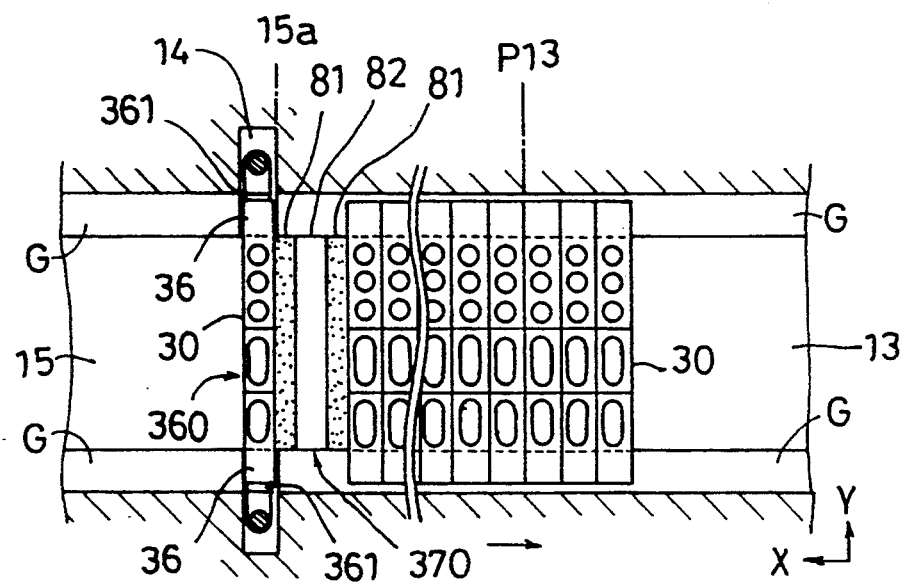
FIGS. 33A and 33B are views showing cartridges standing by in the first reaction path and pushed back by a transport mechanism in a second reaction path, and thereafter pushed forward to a proper position by the transport mechanism in the first reaction path.
Figure 33B:
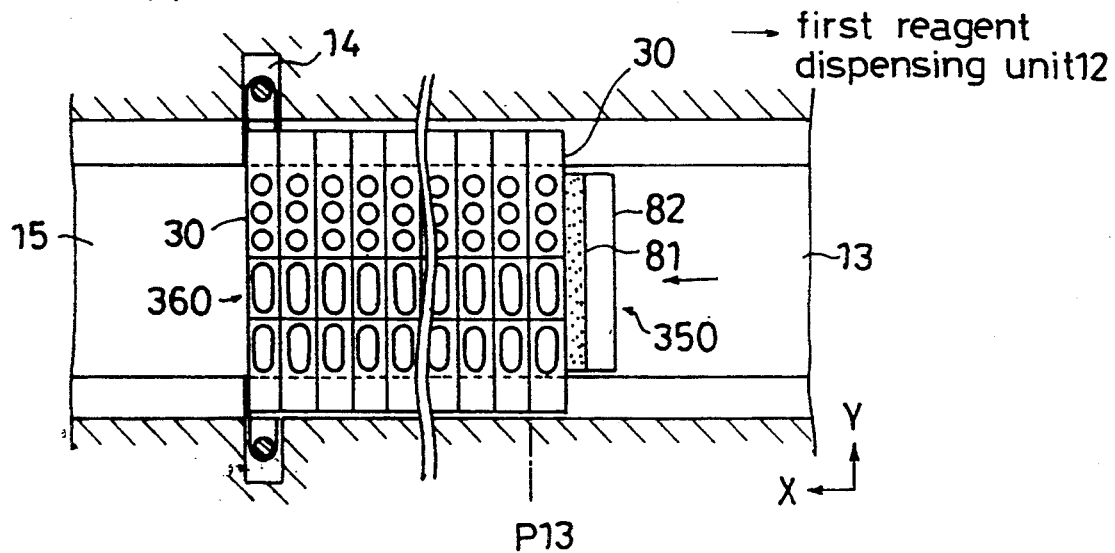

The pusher 82 of the transport mechanism 370 is retractable to the standby position 15a of the second reaction path 15 located at the terminal end of the first reaction path 13. Consequently, the cartridges 30 standing by in the first reaction path 13 are pushed all together back toward the first reagent dispensing section 12 (see FIG. 33A). This presents no problem since a cartridge 30 subsequently transported to the position P13 in the first reaction path 13 pushes these cartridges 30 forward to a proper position (see FIG. 33B). As shown in FIG. 33A, the pusher 82 of the transport mechanism 370 in the second reaction path 15 has silicone rubber 81 bonded to the rear surface as well as the front surface thereof. The silicone rubber 81 on the rear surface mitigates a shock occurring when the pusher 82 is retracted to the standby position 15a as noted above, thereby contacting the leading cartridge 30 standing by in the first reaction path 13.

The cartridge 30 transported to the second reaction path 15 waits in the second reaction path 15, as in the first reaction path 13, until the elapse of a predetermined reaction period for the second reagent dispensed thereto. Thereafter the cartridge 30 is pushed toward an unreacted component removing section 16.

A transport mechanism similar to the transport mechanism 340 for the first reagent dispensing section 12 is provided at a terminal end of the second reaction path 15. This transport mechanism receives a cartridge 30 in a standby position of the unreacted component removing section 16, and raises this cartridge 30 in the Z direction to a treating position of the unreacted component removing section 16 (where unreacted components are removed). After the unreacted components are removed by an unreacted component removing unit 60 included in this section 16, the cartridge 30 is lowered in the Z direction. Thereafter a transport mechanism similar to the transport mechanism 370 and standing by in a standby position (at the terminal end of the second reaction path 15) of a transport line 202 pushes the cartridge 30 through the transport line 202 to a luminescent reagent dispensing section 17.

A transport mechanism similar to the transport mechanism 340 is provided here to receive the cartridge 30 in a standby position of the luminescent reagent dispensing section 17, and raise the cartridge 30 in Z direction to a dispensing position of the luminescent reagent dispensing section 17. After unreacted components are removed by an unreacted component removing unit 60 included in this section 17, a reagent dispensing unit 50 dispenses a luminescent reagent. Then the cartridge 30 is lowered in the Z direction. A transport mechanism similar to the transport mechanism 370 and standing by in a standby position (at the terminal end of the transport line 202) of a transport line 203 pushes the cartridge 30 through the transport line 203 to a hydrogen peroxide dispensing section 18.

A transport mechanism similar to the transport mechanism 340 is provided here too to receive the cartridge 30 in a standby position of the hydrogen peroxide dispensing section 18, and raise the cartridge 30 in Z direction to a dispensing position of the hydrogen peroxide dispensing section 18. A reagent dispensing unit 50 dispenses hydrogen peroxide in this section 18, and thereafter the cartridge 30 is lowered in Z direction. A transport mechanism similar to the transport mechanism 370 and standing by in a standby position (at the terminal end of the transport line 203) of a transport line 204 pushes the cartridge 30 to a predetermined position (corresponding to a reaction period of hydrogen peroxide) in the transport line 204. Upon lapse of the predetermined reaction period the cartridge 30 is pushed to a photometric section 19.

A transport mechanism similar to the transport mechanism 340 is provided here to receive the cartridge 30 in a standby position of the photometric section 19, and raise the cartridge 30 in the Z direction to a photometric position of the photometric section 19 (where photometry is carried out). A photometric unit 70 included in this section 19 carries out photometry. Thereafter the cartridge 30 is lowered in the Z direction to stand by in the standby position of the photometric section 19. This cartridge 30 is pushed to a standby position 205a of a transport line 205 (see FIGS. 23 and 24) by a cartridge 30 subsequently pushed from the transport line 204 to the photometric section 19.

The flange supports of a transport mechanism 370 similar to the transport mechanism 320 stand by in the standby position 205a of the transport line 205 where the cartridge 30 having undergone photometry is pushed out. The flanges 36 of the cartridge 30 pushed out to the standby position 205a are transferred from the flange supports of the transport mechanism of the photometric section 19 to the flange supports of the transport mechanism of the transport line 205. The latter transport mechanism transports the cartridge 30 through the transport line 205 to a discharge position 205b (205c or 205d). A transport mechanism similar to the transport mechanism 21 stands by in a position opposed to a cartridge discharge section 20a (20b or 20c) across the cartridge discharge position 205b (205c or 205d). This transport mechanism discharges the cartridge 30 having completed the examination procedure to the cartridge discharge section 20a (20b or 20c). The cartridge discharge sections 20a, 20b and 20c are used in the stated order under control by the control section 22.

In the second embodiment described above, each of the transport mechanism 310, 320, 330 and 370 for transporting cartridges 30 on an X-Y plane pushes the cartridges 30 to a predetermined position with the pusher 82, or transports the cartridges 30 as supported by the flange supports 321 to a predetermined position. However, belt conveyors may be employed to act as similar transport mechanisms.

Further, in the second embodiment, the cartridges 30 are transported in a three-dimensional space, in rectangular coordinate directions (X, Y and Z directions). To transport the cartridges in a three-dimensional space, the cartridges 30 may be transported along an axis not perpendicular to the X-Y plane, for example.

THIRD EMBODIMENT

A third embodiment will be described next.

Figure 34:
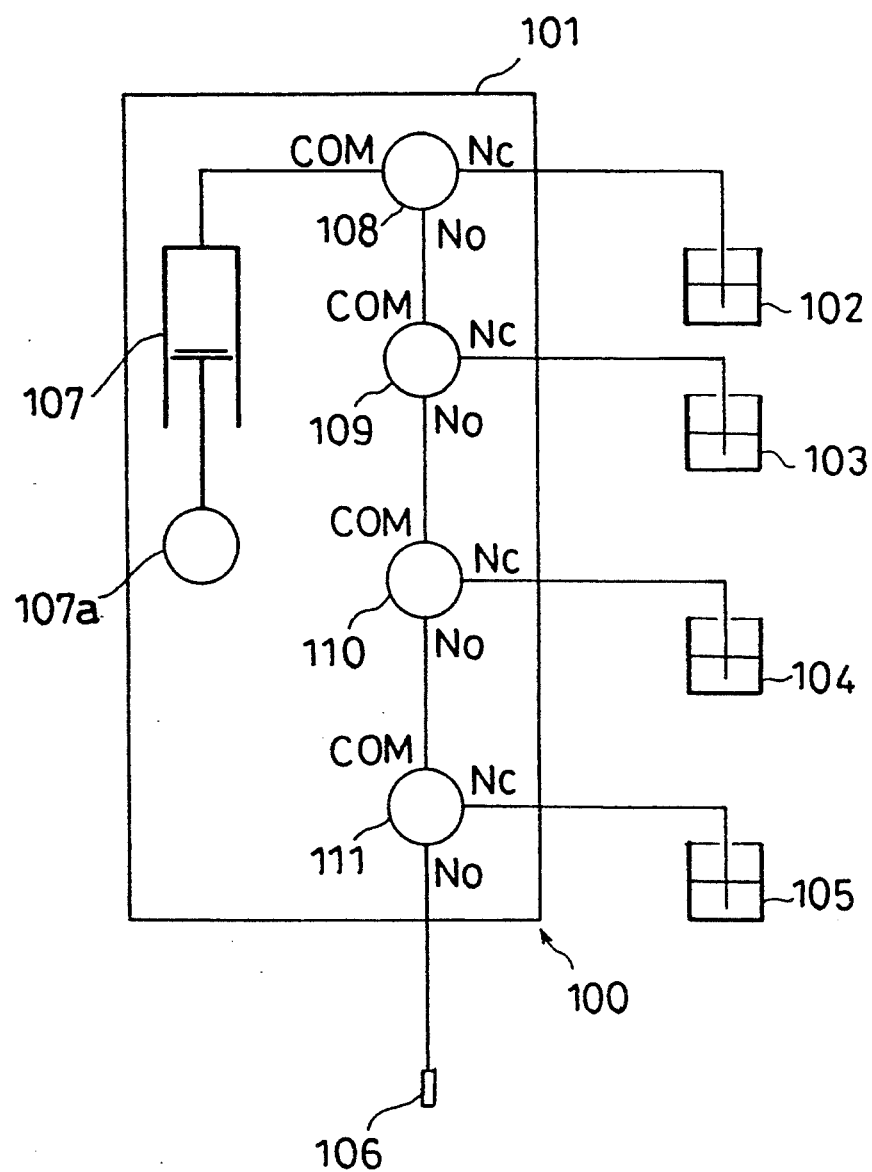
FIG. 34 is a view showing an outline of a reagent dispensing unit in a third embodiment.

The third embodiment employs a reagent dispensing unit 100 as shown in FIG. 34, in place of the reagent dispensing unit 50 used in the first and second embodiments.

Referring to FIG. 34, the reagent dispensing unit 100 includes three reagent containers 103, 104 and 105 connected through three-way valves 109, 110 and 111 to dispense three types of reagents through a single dispensing nozzle 106. In FIG. 34, numeral 101 denotes a dispensation controller, numeral 102 denotes a cleaning buffer container, and numeral 108 denotes a further three-way valve.

Figure 35A:
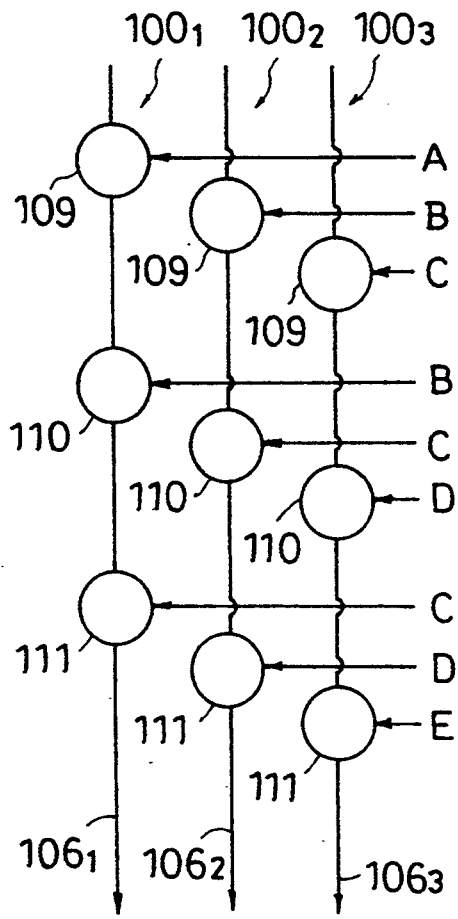
FIGS. 35A and 35B are views for explaining how examination is conducted on a plurality of items with the reagent dispensing unit in the third embodiment.
Figure 35B:
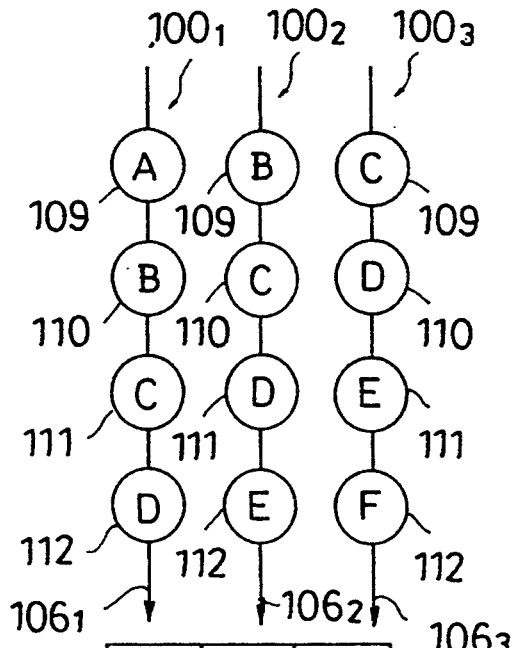

In a basic dispensing operation of this reagent dispensing unit 100, as in the described reagent dispensing unit 50, a desired reagent is dispensed by switching the associated three-way valve, without switching the valves connected to the other reagent containers. Examination on a plurality of items may be conducted in a plurality of combinations as shown in FIGS. 35A and 35B, by connecting a plurality of reagent containers to the single dispensing nozzle 106, and the reagent dispensing unit 100 is formed into a multiple structure corresponding to the number of reaction tubs 33, 34 and 35 of the cartridges 30 (in FIGS. 35A and 35B, three reagent dispensing units 1001, 1002 and 1003 are juxtaposed in a multiple structure). As shown in FIG. 35A, for example, five types of reagents A–E may be assigned to three dispensing nozzles 1061, 1062 and 1063 (of the respective reagent dispensing units 1001, 1002 and 1003) to enable 10 combinations of examinations (as in the table shown in a lower portion of FIG. 35A). For the combination of reagents A, B and C in the top row in the table, for example, reagent A connected to the three-way valve 109 of the reagent dispensing unit 1001 is dispensed to the reaction tub 33, reagent B connected to the three-way valve 109 of the reagent dispensing unit 1002 is dispensed to the reaction tub 34, and reagent C connected to the three-way valve 109 of the reagent dispensing unit 1003 is dispensed to the reaction tub 35. For the combination of reagents A, C and E in the middle row (5th from top) in the table, reagent A connected to the three-way valve 109 of the reagent dispensing unit 1001 is dispensed to the reaction tub 33, reagent C connected to the three-way valve 110 of the reagent dispensing unit 1002 is dispensed to the reaction tub 34, and reagent E connected to the three-way valve 111 of the reagent dispensing unit 1003 is dispensed to the reaction tub 35.

As shown in FIG. 35B (which is a simplified version of FIG. 35A), six types of reagents A–F may be connected to the dispensing units 1001, 1002 and 1003 in the multiple structure (each of the dispensing units 1001, 1002 and 1003 having four reagent containers connected to three-way valves 109, 110, 111 and 112) to enable 20 combinations of examinations. With the reagent containers connected to the respective dispensing nozzles, the number of reagent containers connected to one dispensing nozzle may be minimized to dispense the reagents in all combinations. In this embodiment, three or four reagent containers are connected to one dispensing nozzle. However, this is not limitative, but five or more reagent containers may be connected in the same way through respective three-way valves. While FIG. 34 shows a simple structure type (corresponding to the reagent dispensing unit 50a in the first embodiment), a multiple structure (corresponding to the reagent dispensing unit 50b in the first embodiment) may be employed instead.

Figure 36:
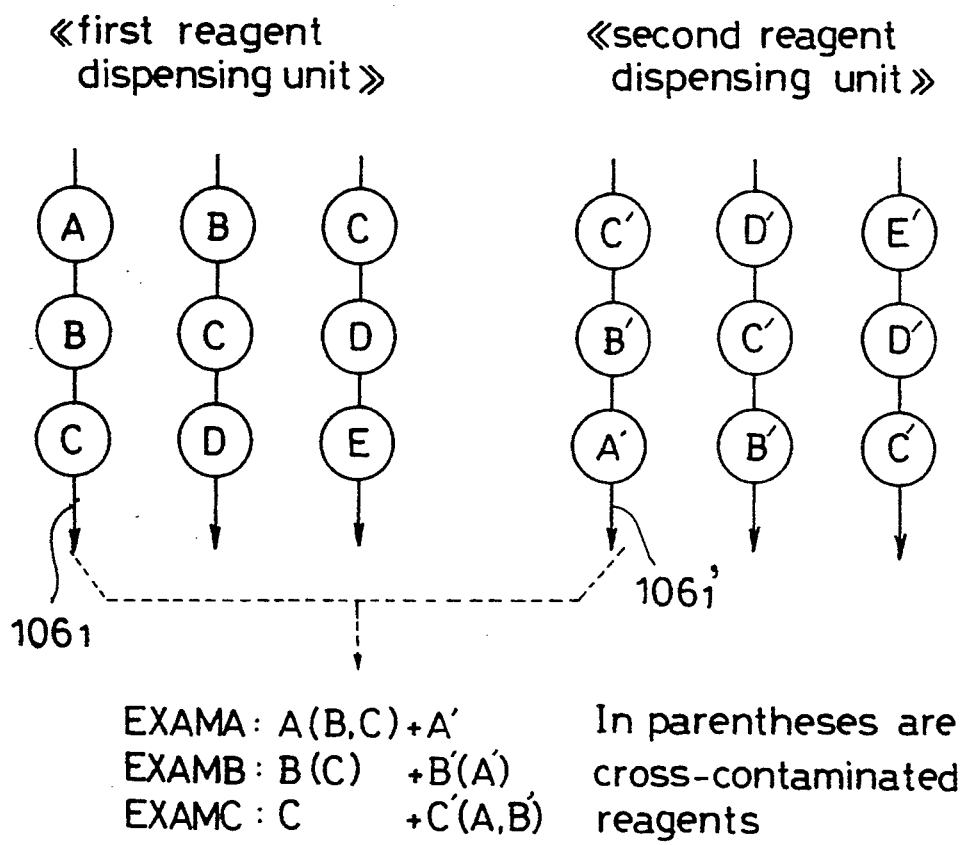
FIG. 36 is a view for explaining how contamination is avoided with the reagent dispensing unit in the third embodiment.

When plural types of reagents are dispensed through the single dispensing nozzle of the reagent dispensing unit 100, what is known as cross contamination (intermingling of the reagents) could take place. In such a case, as shown in FIG. 36, combinations of the reagents may be varied for installation to the reagent dispensing units 100 which dispense first reagents and second reagents. The piping and dispensing nozzles are cleaned with a cleaning buffer after reagent dispensation, and therefore cross contamination may occur in passage switching portions inside the three-way valves. As for a first nozzle 106a for dispensing the first reagents, for example, as shown in FIG. 36, reagent A in the most upstream position may be cross-contaminated with reagent B or reagent C, and reagent B may be cross-contaminated with reagent C. Reagent C in the most downstream position is considered free from cross contamination. Thus, reagents A', B' and C' are arranged in the order shown in FIG. 36 for the first nozzle 1061 which dispenses the second reagents. With regard to the first nozzle 1061' for dispensing the second reagents, reagent A' in the most downstream position has no possibility of cross contamination. Thus, even reagent B or C is mixed into reagent A when dispensing the first reagents, there is no possibility of reagent B' or C' mixing into reagent A' when dispensing the second reagents. Consequently, an examination using reagent A may be conducted without being influenced by reagents B and C.

The apparatus in the third embodiment carries out examinations in basically the same way as the apparatus in the first and second embodiments. As described above, this single apparatus enables examinations to be conducted in a plurality of combinations. For example, different combinations of examinations may be carried out for each specimen. Further, six types of examinations may be effected for one specimen, using two cartridges 30, for example.

Next, a comparison in examination time will be made between the apparatus in the first to third embodiments and prior art apparatus.

This comparison is made by using the apparatus of this invention and prior art apparatus in an examination requiring processes 1–4 and reactions 1–3 for 20 specimens and on three items. It is assumed that processes 1–4 and reactions 1–3 require the following periods of time:

| process 1 | 1 min. |
| reaction 1 | 10 min. |
| process 2 | 3 min. |
| reaction 2 | 20 min. |
| process 3 | 2 min. |
| reaction 3 | 5 min. |
| process 4 | 2 min. |

In the apparatus of this invention, cartridges are successively transported at intervals of three minutes. The total time consumed may be derived from the following equation (1):

examination time for one cartridge + (1)

total time taken by cartridge transport at intervals =

$$(1 + 10 + 3 + 20 + 2 + 5 + 2) + (20 - 1) \times 3 = 100$$

Thus, 100 min./60 examinations.

In the prior art apparatus, it is assumed that the reaction table intermittently rotates at constant speed to transport the reaction vessels at intervals of three minutes. The total time consumed may be derived from the following equation (2):

examination time for one reaction vessel + (2)

total time taken by reaction vessel transport at intervals =

-continued $$(1 + 10 + 3 + 20 + 2 + 5 + 2) + (60 - 1) \times 3 = 220$$

Thus, 220 min./60 examinations.

As seen from the above, the examination time has been reduced to about a half according to the present invention.

The present invention may be embodied in other specific forms without departing from the spirit or essential attributes thereof and, accordingly, reference should be made to the appended claims, rather than to the foregoing specification, as indicating the scope of the invention.

What is claimed is:

1. An automatic analyzing apparatus used for carrying out, in a predetermined order, a plurality of analytic processes including dispensation processes for dispensing selected reagents to reaction tubs each containing a specimen according to predetermined test parameters, and unreacted component removal processes for removing unreacted components from reaction mixtures in said reaction tubs after lapse of predetermined reaction periods following said dispensation processes, and subsequently carrying out photometry of the reaction mixture in said reaction tubs to analyze characteristics of said specimens, said apparatus comprising:

a plurality of cartridges each comprising at least one specimen tub for holding a specimen and a plurality of reaction tubs;

a cartridge standby area for accommodating said plurality of cartridges;

a first transport mechanism for successively transporting said cartridges from said cartridge standby area to a specimen dispensing position;

a specimen dispensing device for distributing said specimen in said specimen tub of each cartridge to each of said reaction tubs in said cartridge;

a plurality of analytical devices for carrying out analytic processes in a pre-determined order wherein said analytical devices comprise a plurality of dispensing devices, for carrying out said dispensation processes to dispense said selected reagents into said reaction tubs of said cartridges wherein each of said dispensing devices dispenses said reagents to all of the reaction tubs of each cartridge in parallel, and unreacted component removing devices, for carrying out said unreacted component removal processes to remove said unreacted components from said reaction tubs wherein each of said unreacted component removing devices removes said unreacted components from all of said reaction tubs of each cartridge in parallel;

an optical device for carrying out photometry of reaction mixtures formed in each of said reaction tubs of said cartridges after said analytic processes are carried out, wherein said optical device comprises multiple optical structures for carrying out photometry in parallel in all of said plurality of reaction tubs in each cartridge;

a plurality of analytic process transport mechanisms drivable independently of one another for successively transporting said cartridges according to said predetermined order of analytic processes between said specimen dispensing device and a first one of said analytical devices, between the respective analytical devices and between one of said analytical devices and said optical device, wherein said specimen dispensing device, said analytical devices and said optical device are all arranged in a three-dimensional space; and transport control means for controlling independent driving of said analytic process transport mechanisms and for controlling driving of each of said analytic process transport mechanisms to transport said cartridges between the specimen dispensing devices, the analytical devices and the optical device in a predetermined variable transport time;

wherein each of the dispensing devices has a construction for dispensing a reagent to one of said reaction tubs of each cartridge, comprising:

a syringe;

a cleaning buffer container;

a plurality of (n) th reagent containers each containing different reagents according to test parameters, wherein (n) is a natural number from 1 to (n) wherein said (n)th reagent container when (n) is equal to 1 is a first reagent container;

a dispensing nozzle;

a first three-way valve an a plurality of (i)th three-way valves, each with a common port, a normally closed port and normally open port, wherein (i) is a natural number from 2 to (n+1) wherein an (i−1)th three-way valve when (i) is equal to 2 is said first three-way valve and wherein said (i)th three-way valve when (i) is equal to 2 is a second three way valve;

said (n)th reagent container and said normally closed port of said (i)th three-way valve being connected to each other by piping;

said common port of the (i)th three-way valve and said normally open port of the (i−1)th three-way valve being connected to each other by piping for each (i);

said cleaning buffer container and said normally closed port of said first three-way valve being connected to each other by piping;

said syringe and said common port of said first three-way value being connected to each other by piping;

said dispensing nozzle and a normally open port of said (i)th three-way valve, when (i) is equal to (n+1), being connected to each other by piping; and dispensation control means operable, prior to reagent dispensation, for effecting controls to fill the piping between said first to (n)th reagent containers and said second to (i)th three-way valves with reagents sucked from the respective reagent containers, while filling said syringe and said piping connecting said syringe and said first three-way valve with a cleaning buffer sucked from said cleaning buffer container; when dispensing one of said reagents contained in said first to (n)th reagent containers through said dispensing nozzle, for effecting controls to pull said syringe to suck air through said dispensing nozzle, to switch said (i)th three-way valve from a position in which a common port and a normally open port thereof communicate with each other to a position in which the common port and a normally closed port thereof communicate with each other when the air has advanced a predetermined amount past the common port of said (i)th three-way valve, to pull said syringe further to suck a predetermined quantity to be dispensed of the reagent toward the common port of said (i)

three-way valve, thereafter to switch said (i)th three-way valve to the position in which the common port and the normally open port thereof communicate with each other, and to push said syringe to dispense the reagent sucked toward the common port of said (i)th three-way valve, through said dispensing nozzle to one of the reaction tubs of a cartridge transported by one of said analytic process transport mechanisms; and when cleaning said dispensing nozzle with said cleaning buffer, for effecting controls to push said syringe to drain said cleaning buffer from said piping through said dispensing nozzle.

2. An apparatus as defined in claim 1, wherein said dispensation control means is operable, when pulling said syringe to suck the predetermined quantity ($\alpha$) to be dispensed of the reagent toward the common port of said (i)th three-way valve during the control for dispensing said reagent through said dispensing nozzle, to cause said syringe to suck an additional quantity ($\beta+\tau$) of the reagent, wherein $\beta$ is a quantity a leading part to be discarded, and $\tau$ is a quantity of a trailing part to be discarded, along with said predetermined quantity ($\alpha$) toward the common port of said (i)th three-way valve; to push said syringe by an amount to discard the reagent in the leading part quantity ($\beta$) in a way to prohibit the same from entering said one of the reaction tubs prior to pushing said syringe to dispense the reagent in said predetermined quantity ($\alpha$) sucked toward the common port of said (i)th three-way valve, through said dispensing nozzle to said one of the reaction tubs; thereafter to push said syringe by an amount to dispense the reagent in said predetermined quantity ($\alpha$) through said dispensing nozzle to said one of the reaction tubs; and subsequently to push said syringe by an amount to discard the reagent in the trailing part quantity ($\tau$) in a way to prohibit the same from entering one of the reaction tubs.

3. An apparatus as defined in claim 1, wherein said syringe, said cleaning buffer container, said first to (n)th reagent containers, said first to (i)th three-way valves and said dispensing nozzle are interconnected through piping each having such a length that a capacity of each piping derived from the length multiplied by a cross-sectional area thereof agrees with a predetermined reference value.

4. An automatic analyzing apparatus used for carrying out, in a predetermined order, a plurality of analytic processes including dispensation processes for dispensing selected reagents to reaction tubs each containing a specimen according to predetermined test parameters, and unreacted component removal processes for removing unreacted components from reaction mixtures in said reaction tubs after lapse of predetermined reaction periods following said dispensation processes, and subsequently carrying out photometry of the reaction mixture in said reaction tubs to analyze characteristics of said specimens, said apparatus comprising:

a plurality of cartridges each comprising at least one specimen tub for holding a specimen and a plurality of reaction tubs;

a cartridge standby area for accommodating said plurality of cartridges;

a first transport mechanism for successively transporting said cartridges from said cartridge standby area to a specimen dispensing position;

a specimen dispensing device for distributing said specimen in said specimen tub of each cartridge to each of said reaction tubs in said cartridge;

a plurality of analytical devices for carrying out analytic processes in a pre-determined order wherein said analytical devices comprise a plurality of dispensing devices, for carrying out said dispensation processes to dispense said selected reagents into said reaction tubs of said cartridges wherein each of said dispensing devices dispenses said reagents to all of the reaction tubs of each cartridge in parallel, and unreacted component removing devices, for carrying out said unreacted component removal processes to remove said unreacted components from said reaction tubs wherein each of said unreacted component removing devices removes said unreacted components from all of said reaction tubs of each cartridge in parallel;

an optical device for carrying out photometry of reaction mixtures formed in each of said reaction tubs of said cartridges after said analytic processes are carried out, wherein said optical device comprises multiple optical structures for carrying out photometry in parallel in all of said plurality of reaction tubs in each cartridge;

a plurality of analytic process transport mechanisms drivable independently of one another for successively transporting said cartridges according to said predetermined order of analytic processes between said specimen dispensing device and a first one of said analytical devices, between the respective analytical devices and between one of said analytical devices and said optical device, wherein said specimen dispensing device, said analytical devices and said optical device are all arranged in a three-dimensional space; and transport control means for controlling independent driving of said analytic process transport mechanisms and for controlling driving of each of said analytic process transport mechanisms to transport said cartridges between the specimen dispensing devices, the analytical devices and the optical device in a predetermined variable transport time;

wherein each of the dispensing devices has a construction for dispensing a reagent to one of said reaction tubs of each cartridge, said construction comprising:

a syringe;

a cleaning buffer container;

a reagent container;

a dispensing nozzle;

a first three-way valve with a common port, a normally closed port and a normally open port;

a second three-way valve with a common port, a normally closed port and a normally open port;

a first piping connecting said syringe with said common port of said first three-way valve;

a second piping connecting said cleaning buffer container with said normally closed port of said first three-way valve;

a third piping connecting said common port of said second three-way valve with said normally open port of said first three-way valve;

a fourth piping connecting said reagent container with said normally closed port of said second three-way valve;

a fifth piping connecting said dispensing nozzle with said normally open port of said second three-way valve; and dispensation control means operable, prior to reagent dispensation, for effecting controls to fill said fourth piping between said reagent container and said second three-way valve with a reagent sucked from said reagent container and filling said second and first piping including said syringe with a cleaning buffer sucked from said cleaning buffer container; when dispensing said reagent through said dispensing nozzle, for effecting controls to pull said syringe to suck air through said dispensing nozzle, to switch said second three-way valve from a position in which the common port and the normally open port thereof communicate with each other to a position in which the common port and the normally closed port thereof communicate with each other when the air has advanced a predetermined amount past the common port of said second three-way valve, to pull said syringe further to suck a predetermined quantity to be dispensed of the reagent toward the common port of said second three-way valve, thereafter to switch said second three-way valve to the position in which the common port and the normally open port thereof communicate with each other, and to push said syringe to dispense the reagent sucked toward the common port of said second three-way valve, through said dispensing nozzle to one of the reaction tubs of a cartridge transported by one of said analytic process transport mechanisms; and when cleaning said dispensing nozzle with said cleaning buffer, for effecting controls to push said syringe to drain said cleaning buffer from said fifth piping through said dispensing nozzle;

wherein said dispensation control means is operable, when pulling said syringe to suck a predetermined quantity ($\alpha$) to be dispensed of the reagent toward the common port of said second three-way valve during the control for dispensing said reagent through said dispensing nozzle, to cause said syringe to suck and additional quantity ($\beta+\tau$) of the reagent, wherein ($\beta$) is a quantity of a leading part to be discarded, and ($\tau$) is a quantity of a trailing part to be discarded, along with said predetermined quantity ($\alpha$) toward the common port of said second three-way valve; to push said syringe by an amount to discard the reagent in the leading part quantity ($\beta$) in a way to prohibit the same from entering said one of the reaction tubs prior to pushing said syringe to dispense the reagent in said predetermined quantity ($\alpha$) sucked toward the common port of said second three-way valve, through said dispensing nozzle to said one of the reaction tubs; thereafter to push said syringe by an amount to dispense the reagent in said predetermined quantity ($\alpha$) through said dispensing nozzle to said one of the reaction tubs; and subsequently to push said syringe by an amount to discard the reagent in the trailing part quantity ($\tau$) in a way to prohibit the same from entering said one of the reaction tubs.

5. An automatic analyzing apparatus used for carrying out, in a predetermined order, a plurality of analytic processes including dispensation processes for dispensing selected reagents to reaction tubs each containing a specimen according to predetermined test parameters, and unreacted component removal processes for removing unreacted components from reaction mixtures in said reaction tubs after lapse of predetermined reaction periods following said dispensation processes, and subsequently carrying out photometry of the reaction mixture in said reaction tubs to analyze characteristics of said specimens, said apparatus comprising:

a plurality of cartridges each comprising at least one specimen tub for holding a specimen and a plurality of reaction tubs;

a cartridge standby area for accommodating said plurality of cartridges;

a first transport mechanism for successively transporting said cartridges from said cartridge standby area to a specimen dispensing position;

a specimen dispensing device for distributing said specimen in said specimen tub of each cartridge to each of said reaction tubs in said cartridge;

a plurality of analytical devices for carrying out analytic processes in a pre-determined order wherein said analytical devices comprise a plurality of dispensing devices, for carrying out said dispensation processes to dispense said selected reagents into said reaction tubs of said cartridges wherein each of said dispensing devices dispenses said reagents to all of the reaction tubs of each cartridge in parallel, and unreacted component removing devices, for carrying out said unreacted component removal processes to remove said unreacted components from said reaction tubs wherein each of said unreacted component removing devices removes said unreacted components from all of said reaction tubs of each cartridge in parallel;

an optical device for carrying out photometry of reaction mixtures formed in each of said reaction tubs of said cartridges after said analytic processes are carried out, wherein said optical device comprises multiple optical structures for carrying out photometry in parallel in all of said plurality of reaction tubs in each cartridge;

a plurality of analytic process transport mechanisms drivable independently of one another for successively transporting said cartridges according to said predetermined order of analytic processes between said specimen dispensing device and a first one of said analytical devices, between the respective analytical devices and between one of said analytical devices and said optical device, wherein said specimen dispensing device, said analytical devices and said optical device are all arranged in a three-dimensional space; and transport control means for controlling independent driving of said analytic process transport mechanisms and for controlling driving of each of said analytical process transport mechanisms to transport said cartridges between the specimen dispensing devices, the analytical devices and the optical device in a predetermined variable transport time;

wherein the optical device has a construction for carrying out photometry of a reaction mixture formed in one of said reaction tubs of each cartridge, comprising:

reaction mixture takeout means having a flow cell, with first and second ends, for detaining a reaction mixture capable of emitting light, said flow cell being penetrable by light emitted from said reaction mixture;

photodetecting means for detecting the light emitted from said reaction mixture detained in said flow cell and outputting information on a quantity of light;

light shielding means for shutting off said flow cell and said photodetecting means from ambient light;

a syringe;

a nozzle;

a first cleaning buffer container containing a cleaning buffer for cleaning said nozzle;

a second cleaning buffer container containing a cleaning buffer for cleaning said flow cell;

a first three-way valve with a common port, a normally closed port and a normally open port;

a second three-way valve with a common port, a normally closed port and a normally open port;

said syringe and said common port of said first three-way valve being connected to each other by piping;

said first cleaning buffer container and said normally closed port of said first three-way valve being connected to each other by piping;

a common port of said second three-way valve and said normally open port of said first three-way valve being connected to each other by piping;

said second cleaning buffer container and said normally closed port of said second three-way valve being connected to each other by piping;

said first end of said flow cell of said reaction mixture takeout means and said normally open port of said second three-way valve being connected to each other by piping;

said second end of said flow cell and said nozzle being connected to each other by piping; and photometry control means operable, when carrying out photometry, for effecting controls to pull said syringe to suck said reaction mixture into said flow cell from said one of the reaction tubs of the cartridge transported by the analytic process transport mechanisms, to stop said syringe to allow said flow cell to detain said reaction mixture, to cause said photodetecting means to detect quantity of the light emitted from said reaction mixture, and thereafter to push said syringe to drain said reaction mixture through said nozzle; and when cleaning one of said flow cell and said nozzle, to switch one of the first and second three-way valves from a position in which the common port and the normally open port thereof communicate with each other to a position in which the common port and the normally closed port thereof communicate with each other, and to drain one of said cleaning buffers through one of said flow cell and said nozzle.

6. An apparatus as defined in claim 5, wherein said reaction mixture takeout means, said syringe, said nozzle, said first and second cleaning buffer containers, and said first and second three-way valves are interconnected through said piping wherein each of said piping having such a length that a capacity of each piping derived from the length multiplied by a cross-sectional area thereof agrees with a predetermined reference value.

* * * * *